(12) United States Patent
Basu et al.

(10) Patent No.: US 10,047,373 B2
(45) Date of Patent: Aug. 14, 2018

(54) GENETIC MARKERS ASSOCIATED WITH DROUGHT TOLERANCE IN MAIZE

(71) Applicant: Syngenta Participations AG, Basel (CH)

(72) Inventors: Shib Sankar Basu, Research Triangle Park, NC (US); Michael Mahlon Magwire, Research Triangle Park, NC (US)

(73) Assignee: Syngenta Participations AG, Basel (CH)

( * ) Notice: Subject to any disclaimer, the term of this patent is extended or adjusted under 35 U.S.C. 154(b) by 125 days.

(21) Appl. No.: 14/967,593

(22) Filed: Dec. 14, 2015

(65) Prior Publication Data

US 2017/0166916 A1 Jun. 15, 2017

(51) Int. Cl.
  *C12N 15/82* (2006.01)
  *C12Q 1/68* (2018.01)
  *A01H 5/10* (2018.01)
  *C12Q 1/6895* (2018.01)
  *A01H 1/04* (2006.01)

(52) U.S. Cl.
  CPC ........... *C12N 15/8273* (2013.01); *A01H 1/04* (2013.01); *A01H 5/10* (2013.01); *C12Q 1/6895* (2013.01); *C12Q 2600/13* (2013.01); *C12Q 2600/156* (2013.01)

(58) Field of Classification Search
  None
  See application file for complete search history.

(56) References Cited

U.S. PATENT DOCUMENTS

| 2011/0191892 | A1 | 8/2011 | Kishore et al. |
| 2016/0355835 | A1 | 12/2016 | Frommer |

OTHER PUBLICATIONS

*Zea mays* cultivar B73 chromosome 5 clone CH201-257F15, GenBank accession No. AC208973, published Sep. 23, 2013.*

* cited by examiner

*Primary Examiner* — Matthew R Keogh
*Assistant Examiner* — Bratislav Stankovic
(74) *Attorney, Agent, or Firm* — Kevin Markham

(57) ABSTRACT

The present invention relates to methods and compositions for identifying, selecting and/or producing a maize plant or maize plant part having increased yield under non-drought conditions, increased yield stability under drought conditions, and/or increased drought tolerance. A maize plant or maize plant part, including any progeny and/or seeds derived from a maize plant or germplasm identified, selected and/or produced by any of the methods of the present invention is also provided.

4 Claims, 1 Drawing Sheet

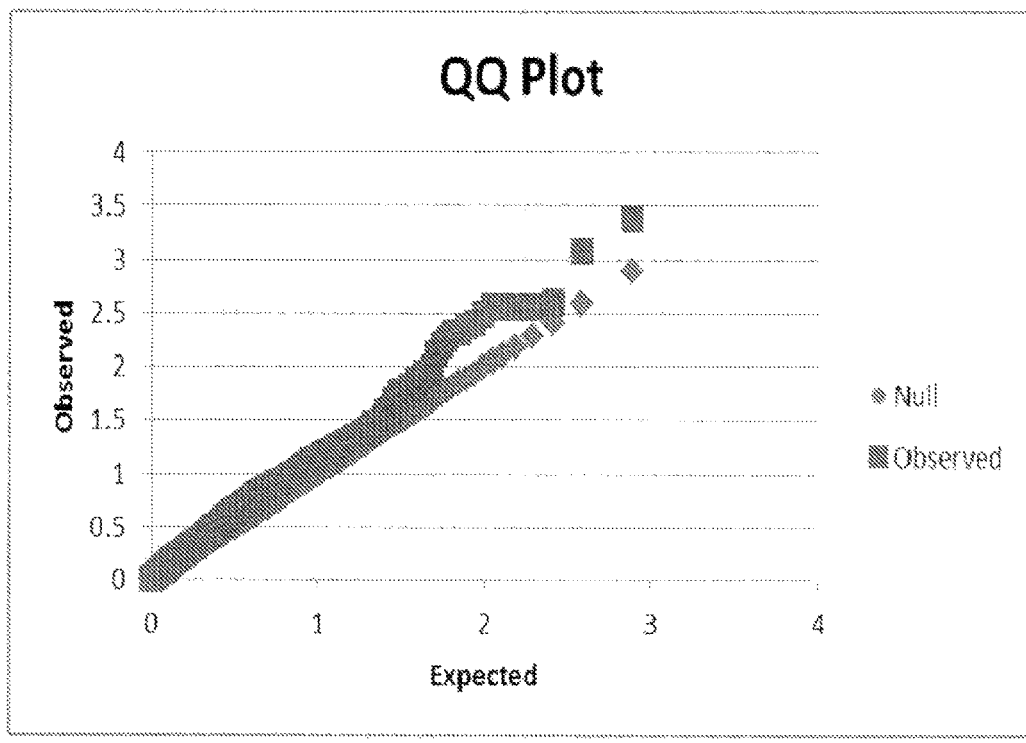

SEQUENCE LISTING

<160> NUMBER OF SEQ ID NOS: 19

<210> SEQ ID NO 1
<211> LENGTH: 2656
<212> TYPE: DNA
<213> ORGANISM: Zea mays

<400> SEQUENCE: 1
gcctatataa agccacccac agccctgcct atcattgcaa gagtttgagc caacacacac      60
agagagagga caactcctca caactctccc ttccctcctg tagggggccaa aagggttaga    120 gagtaggaga agtagttccc tagcccaaca caagaaaaac aagctcgatc tcctcatcac    180

```
cctaatccaa gcaactgctt tgtgtgttgg gaaattcttg tgacccctgt tatattatta      240
tccgtgtagc tactagcttc attccccct  ttgtacccat caaatggctg gcatgtctct      300
gcaacacccc tgggcgtttg ctttcggtct actaggtaca tactcaccct tcactaatag      360
ctaaacaagc gcccgccgca aagctatgaa ttaagggcag gcatgtttgg tttgctacct      420
attttaccat actttgtcta actttttctgt ctaaggttat agttcttcaa ttcgaacgat     480
taatcttagc caaagtgtga catggttagc cacgaactaa gcaggccctt aattattgcg      540
catgtatata ttatatattt atcttttctat tctgtttaat ttgttttctc tttacatata    600
tatactacta tgtaagtata tattatatgc acaacaagca ggcctccttc gtgcacatat     660
gcatagaatc aatctatacc cttcatagaa gccactttga gatataccct ccaaaacaat    720
cccaaaaaca agacgctcga tcttgcgctc acaatcactt agttttgcac cagattaagc    780
atgcaccact agattttatg tactgtatta cctctgccat ccatggtcga tcctttagtt    840
tatcctattc atttccgtca tgaactacct gtcgagctag caatcggtcc tttatttaga    900
gtgttcagat aggcatctgt ctttatacaa acaataaagc ctcacgaatc tttagtcaca    960
aaacaaggca aattagacag gccacggagg tgtaaagtgt cagctctgct tatcacaact   1020
tatctctgct ttatttgggc acacttttgc catacaaatg gctgatcttg gcgcctttt   1080 tttctccttg ctttgcaggt aacgtcatct ccttcatgac cttcctggcc ccgatgtaag   1140
tgacatatat atatatatat attgcttaat taattatcac tgcttcttca gatatatatt   1200
catcggttat tttaattaat tatgtggata tgtatgcatc gtataacaga ccgacgttct   1260
accgcatcta caagagcaag tcgacggaag gcttccagtc ggttccctac gtggttgccc   1320
tgttcagcgc catgctgtgg atcttctacg cactgatcaa gtccaacgag accttcctca   1380
tcaccatcaa cgccgccggc tgcgtcatcg agaccatcta cgtcgtcatg tacttcgtct   1440
acgcgcccaa gaaagccaag ctgttcacgg ccaagatcat ggtcctcctc aatggcggcg   1500
tctttggggt catcctcctg ctcaccctttc tcctcttcaa gggcagtaag cgcgttgtgc   1560
tgcttggctg gatctgcgtc ggcttctccg tcagtgtctt cgtcgcgcca ctcagcatca   1620
tggtgagccc tgagcacgcg tataaaactg tgccaagatg catggacgac agatcgatca   1680
acccaatcag ttttgatcca tgtgtatcgt ttctaatgca ccgtgtttat atatgtgtgc   1740
agagacgagt gatccagacg aagagcgtgg agtacatgcc cttctccctc tccctctcgc   1800
tcaccctcag cgccgtcgtc tggttcctct acggcctcct catcaaggac aaatacgtcg   1860
cggtaattgt ttcatctaat ctgctgcaac cgccatggta ttggtatctc tcactggtct   1920
ttactgataa actacatacg atctctgtac gtatgcagct tccaaacatc tgggggttca   1980
ccttcggcgt ggtccagatg gtgctctacg tgttgtacat gaacaagacg ccggtggcgg   2040
cgactgccga gggcaaggat gccggcaagc tttcctcagc tgcagacgag cacgtcctcg   2100
tcaacatcgc caagctcagc ccagccctcc cggagaggag ctccggggtg cacccagtca   2160
cccagatggc gggcgttcct gtcaggagct gcgctgctga agcaaccgcg ccggcgatgc   2220
tgcccaacag ggacgtggtc gacgtcttcg tcagccgaca cagccccgcc gtccacgtgg   2280
catagattct cgatcgatcg cgtgcatggc ccatgcatgc gcccgccaca cgtacgctag   2340
cttttatata ttcgaaggac gacttgctgc tggtcgtgag catatatatg atggagaaaa   2400
tgattaagta gtatatatat aagtaattaa ctgccatgca tggaagctag ctaatggatg   2460
gaggcagagg ccagaacgat gaaggggggaa gctatacata tatgtgtgta attaatatag   2520
```

```
atatatgggc tttgtgttca tctttgcagc tatgtattaa tttgcatgga tatctgttat    2580 tccttttat gtgtaacgtc ttctaataaa atgtaattga acccacacta ctgttgttag    2640
ctaccacaag tttccc                                                    2656

<210> SEQ ID NO 2
<211> LENGTH: 3653
<212> TYPE: DNA
<213> ORGANISM: Zea mays

<400> SEQUENCE: 2
ggctctcttc tccaccggtc ctacccctta cctcccaaga tcacaatcct ctgctcctta      60
tatattagcc acaccgctcg ttccctgctg caccgggtga cacacaggca caaagacacc     120
gcccgtacac aggctcgttg gcttggctgc tgtgtgttgc gctcagccat tcagacttga     180
gagctactag ctaactgctc gttgggtgtg ggtgcgctcc cggcctagac cgtggaggaa     240
aggagtccag tccactcact acccctctg ctccgttcgg gttccaggcc agcacagccg     300
agggttccgc acagcgataa gcgcgaagcg gaagagatgg agcatatcgc caggttcttc     360
ttcggagttt ctggtcagta tcaccatgcc attcctgcct ctgctgcatg cctacctgat     420
ggtcttcttc ttgcctcgcc taatctctgt tagatctgtc tccccaggga atgtcattgc     480
gctcttcctc ttcctgtcgc ctgtgtaagt ttttgattcc acgtacctga atccttctgt     540
tcctcactgc ccgcgtccat gctttaaaaa aaaaatcgaa aacagagaag caatgatata     600
gtacttactt ctactatatg acaaagacta gaacatgggg agaatcagtg tggagagaaa     660
ggctatagca tcttttaggt tcaatccttt ccagcgaaac actgaaattt catacatata     720
taattttttt ctaaaaaaag caagtagctt ttccccatcc gaaatgcttc ttcttcccaa     780
ccacgccgca cctttttttct tgcgtcttgc ctcagcagcc ttcaggggca gcagcgcagt     840
gcgtgtgttc ctctgacggg tgagaaatct ctttgcagtg tcaccttctg gagggtcatc     900
aggaagcggt cgacggagga cttctccggc gtgccctaca acatgacgct gctcaactgc     960
ctcctatcgg cttggtaacg aaccgctctc tctctctctc tctccctgag agacacggcc    1020
ttttgatgag cactccacac catttctgtt tctgtctctt cagaaaatta atcgcatcg    1080 cagatttatg gagtggccgt aaagcagtaa accggcgtg gtggtgtagt ttgtttact    1140 tagatttcgg aaatgctgca tggtttgctg gcctgggtga agcaaacgct tggctcctag    1200
cgtagcctct gcccaacccg gcctgtcctg tagatagagt actaccgtg gacccactcg    1260 ctagacgcta gcactgtaag tctgtgacaa cgactgcaat gaaggggaa aagcttattg    1320 cactgcacca ctgcccgtgg gagcagagcc tacctgttgg cattgccagg acggagatga    1380
cgacctgtgg gcctcgcggc ccttgagccc gcacatgcag cgtcacgttc aagtgttcgt    1440
acctccaaac aaaaaaagtc ttgacgcttt ttttttttctt tttggttatt atgatgacgg    1500
acgattctgg tcagggcatc cacataaata tcttaaaagg tattaacgac gtaagtgcaa    1560
aaaaaaagac agtctctagc actaccacgg ttttatccat acaactcacg tacatgaatc    1620
atatcatgag atcttctagt ggaataagat ataaaactta aatatattgg gctatatgaa    1680
agagtttttt agatgtattt agtgcttaaa gaactgaaac gtagtatcta gattgtacat    1740
gtctttatga ctatatggat gagttggtgt cccgtttgat ttttcacgcg cctttgaatc    1800
catgtgaaga tcgatgtgct agctagctag ctcgctcttc atgcgttcgt ctggattttg    1860
tttgaaattc acgcagcata tatgtgtgga atataatctg tatgcacata caggtacggc    1920
ctgccgttcg tgtccccgaa caacatcctg gtgtcgacga tcaacgggac ggggtcggtg    1980
```

```
atcgaggcca tctacgtggt gatcttcctc atcttcgcgg tggaccggcg ggccaggctc    2040
agcatgctgg gcctcctggg catcgtcgcc tccatcttca ccaccgtggt gctcgtctcg    2100
ctgctggccc tccacggcaa cgcccgcaag gtcttctgcg gcctcgccgc caccatcttc    2160
tccatctgca tgtacgcctc gccgctctcc atcatggtac gtgagcgatg atgattggtt    2220
gttgctgcct tgctgggtag ctagctccag cgggtcccct tctgggcgtg tacgtgcgtc    2280
cttgctgtca acgtacggca tcagttaaca agctaagcgt gtgcttggtg tgtgcagagg    2340
ctggtgatca agacgaagag cgtggagttc atgccgttcc tgctctccct ggccgtgttc    2400
ctgtgcggca cctcctggtt catctacggc ctcctcggcc gcgacccctt cattattgta    2460
cgcacacggt tctctctcta gtctagatcc tgagccgcac tcaccgcccg ccgtacgca     2520 cgtgctatcc gcgcatgttg tccgattggc actcggaaac cactgtagca gcactgtatc    2580
actagctgtt gggactggac gtaactgcat ctgatctggc cagcacagta cccccgggct    2640
gggcgtcggt tgccctttcg atgtcccgcc caagcccaac caggcgcaca tgcctgccgc    2700
tgccgcagcc gatgcacggg catgggcgcc ggtagcgtct agcagcgtgg gcgtggccac    2760
ccacaggcag cgcacgccgg tgctagctgc cgatgggccg ccgtgcccat gtccatgcag    2820
ctggattgga cccggcacag gcagaagcaa cagcgcccgc gctcttcctt gtcgcaatgc    2880
tagttagcaa actgcacggt gcactccact tcagtacaca ccaacgcgac agactgcgat    2940
gaaatatcta aggccgagtt ttttttttt gcaaatctca tcatgtcgga atgattcatg     3000
cggtccaaac ttcagcacac ccccactgtc gctaaacccg cgctgtctgt gcatgcgtgc    3060
agatcccgaa cgggtgcggg agcttcctgg gcctgatgca gctcatcctg tacgccatct    3120
accggaaaaa caagggcccc gccgcgccgg ccggcaaggg agaggccgcc gccgccgccg    3180
cggaggtgga ggacaccaag aaggtggccg ctgccgtgga gctggccgat gccacgacca    3240
acaaggcagc ggacgccgtc ggcggcgacg gcaaggtcgc cagccaggtg taggcgggca    3300
aggcttattt gctgtctggg actgggagga acatcctaaa cgaggctgcc ttagtttgtc    3360
ggtggagcag attggtgttg gtttctgtgg gcttttacgg ttgttgttac tctcatctcc    3420
atctctccca ggaggctacc ccaagcatgt agtagcttcc attctgattc tgggacggtg    3480
ttgcacgtta cagtgctctc aagctgtctc tgcaaagtgt gttttttat tccatttccc     3540 tcctgctctt gttctccaac tgcgcttacc tgccccgat ttctaaaa aatgtattaa       3600 actatctgag aaattcatcc aactgcgagt actgtgctgt gcgtgagcaa tgc           3653
```

<210> SEQ ID NO 3
<211> LENGTH: 2911
<212> TYPE: DNA
<213> ORGANISM: Zea mays

<400> SEQUENCE: 3

```
acacacaaac acatcagcat tcagcaatag ctaatcgagc atcgtcgcct tagctcctct      60
cctctcctct ccgtcgtcgt ggaacttctc tccgccggct gtcatatata taaggagaa     120 gaagagaaca gcaactctag ctagccggcc ggcctccgtc gtcgccggcg tcgtcgacta    180
gctagctaac tctcgatctc cagttcctgc ccccgcgccc cacgcccggc cgtcgtcgtc    240
agcaatggca ggaggcttct tctccatggc tcacccggcc gtcaccctct ccggcatcgc    300
aggtacgtac gcgccaatga acaacaacg tcgtctcgag ctagatcgat ccatgcatga    360
cgccggccgg gaccggccgg atagataggc ggagatcgac ttgcataatg cttcgcgtgt    420
```

```
ttggccttttt cctggtgctt cttttttttt ttaaaaaaaa tcttatggga ccttgatgac    480
atgcttttca tgtggttttc attcattctg ttgccgtact acgttcttct agattttgtt    540
tattccgaca tgacgactgt cttgtccatc cttgtatcat cgatccgtcc tttgcatgca    600
tgcatccacc agtcgtcagc cttccttttt gccgtttgtg ccattgcact gtagagcacg    660
cacgcactct ctagctgtag agaggcgcgg cagtaggcat gcatgcagca gctagtcaca    720
ctggacaacc aactgtcttg tccatcatct atcaacaata cttgcatatc agaatacgta    780
gtatgtagct ttagcatttt ttttcttca cctatactac tgctagctgc atcttcttga    840
actttctctg atgctcccg cggcccattg agacgacgat gcactctttc tccaattcgt    900
tagctgcgat catggcacag gccttaatt tgttgctagc tagaacacac atgcatgcat    960
cgccgaggta tagcaacttt tccactcaag aataatggta ataagcagtg cagatcagat   1020
ccacatattg ggcattagat cacgaaatac agttgcaaat agctgctcac aacgtaacgc   1080
actatctaag aatcatttct atatacgtgt attttttgct ggaatggtta tgatcgatcg   1140
gttgggcatg cagcagggaa ggcgtgtgcg tgtgcatgca gctacctagc ttttttgccat  1200
atcagcgttt ccttaaccta atcaccacgc ttctctctgt tagtggacgc acacgcattg   1260
tacatatata tgtgtatagt attgtactcc taccactttt actgaaaatg acgacactga   1320
cgcgtagtta ccctcttctc tcttgtttct tcgatttgga ttgtgcagga aacatcatct   1380
ccttcctggt gttccttgca ccagtgtaag tagctagcta tagccacctt tcttcgttcc   1440
cttactgtct caatttcaga ccgactcgga ttcatgcgtg aatcgatgga tgatccaaga   1500
ctgacatggc atgcctcttg tacgcaccgt accaaaaaca gggcgacgtt cctgcaggtg   1560
taccggaaga agtcgacggg cgggttcagc tcggtgccgt acgtggtggc gctcttcagc   1620
tcggtgctgt ggatcttcta cgcgctggtg aagaccaact cgaggccgct gctgaccatc   1680
aacgccttcg gctgcggcgt ggaggcggcc tacatagtcc tctacctggc gtacgcgccg   1740
cggcgggcgc gcctgcggac tctggcctac ttcttcctgc tggacgtggc ggccttcgcg   1800
ctcgtcgtcg ccgtcacgct cttcgccgtc cgcgagcccc accgcgtcaa gttcctcggc   1860
agcgtctgcc tcgccttctc catggccgtc ttcgtcgcgc cgctcagcat catcgtcaag   1920
gtggtcaaga ccaagagcgt cgagttcctg cccatcagcc tctccttctg cctcacgctc   1980
agcgccgtcg cctggttctg ctacggcctc ttcaccaagg accccttgt catggtaacg   2040
actgatcaat aatgtaatat atggttaact gatccatata tatatataaa atggtaactg   2100
aataatgctg gggatgtttc tcgattatat atatctattc agtaccccaa cgtcggcggc   2160
ttcttcttca gctgcgtcca gatgggcctc tacttctggt accgcaagcc ccgcccggcg   2220
gccaagaaca acgccgtgct gccgacgacc acggacggcg ccaacgcggt gcaggtgcag   2280
gggcaggtca tcgagctggc gcccaacacg gtggccatcc tgtcggtgag ccccatcccc   2340
atcgtgggcg tgcacaagat cgaggtggtg gagcagcagc acaaggaggc cgccgtggcc   2400
gccgagaccc gccggatggc cgccgcaaac ccggacggcg ccatgccgga ggtcatcgag   2460
atcgtccccg ccgccgccgc ggtgtgaccc aacgccaatc accatgcacc gtacacaccc   2520
tgctagcttc ttattagcta gctcggatga cgtacgacag tttggtggca agtggctggc   2580
agctcaagca tgcagatgca ggcatcgtcg tctgctagtt gatcgtttag ttggttaatt   2640
gttggattat tattgcgtgt ctctctcgtg tgcgtagtct tgtcagttca gttcagttca   2700
gtgtcgaatc aagtagtagt agctgttgtt tgcattggat ctgacaatgc atgctaataa   2760
ttatggtggt gtgatggtct tggtcggtac gtgcgtagtc gtctacgtac gccgtgtcaa   2820
```

```
cgtcgtagat ctctacggga agatgataag actgtaacat gcagggcatg catctattta    2880
tacttaacat attctttgtg tgcttaattt t                                   2911

<210> SEQ ID NO 4
<211> LENGTH: 5438
<212> TYPE: DNA
<213> ORGANISM: Zea mays

<400> SEQUENCE: 4
ctgagctgac tgtggatctc atccgtatcg tatatacgtc gtcctgtttg gatccaccgc      60
gttttgctaa ttcccttcga accggccggt ggccttcgtt ctcccaccag gcctgtctgt     120
ctgctgtatc cgccagagct tccatggatt ccaccctctt catcatcggc gtcataggta     180
agcttgtgta tcattctgaa ctgctttgtt attattatta gtcttcattc gtccagcttt     240
ccttatcttc ttcttctaca ttgaaatagg caacatcatc tcagttctcg tcttcatatc     300
gcctatgtaa gtgtctttct ccatatatat ggtttccctg tcgtcgctgt tgctagctag     360 cttttctttct gaacaccacc acgggcacca atccatgcat ggatacagca agacgttctg     420
gaggatcgtg cggggcggga cgacggagga gttcgagccg gcgccgtacg tgttgacgct     480
gctcaacgcg ctgctgtggc tctactacgg cctcaccaag cctgacggct cctcgtcgc     540 caccgtcaat ggctttgggg ctgtcatgga ggccatctac gtcgtcctct tcatcgtcta     600
cgccgccaac catgccacaa gggtgagggg tcggagcagc tggggccagt atatatagtt     660
cactcacaca atccgttgct taattctgca taattctttc ttcaagcact tgagtcttag     720
gaattacgga gtatatagtt aaagaaaagc acaaccacca ttcgtttatt aaagaaaagc     780
atgtgttgcc ttatattata gtttgttcct ttatcgcaat tatgattatg caggttaaga     840
ccgcgaagct ggcagcagcg ttggacatcg gtggcttcgg agtcgtgttt gcggccacca     900
cattcgccat cagtgaattt gaattgagaa ttatggtgat aggaatgata tgtgcctgcc     960
tcaatgtgct catgtacggg tcaccccttg cttctatggt aagttttttt tcctcacatg    1020
catatttata cactattcct cttttctttc cttttttggt tattttagaa acttaaatcc    1080
cctctggtat taattcccga gaatttcact taattcccaa gaatcccaaa aaaaattaag    1140
tttctaaact agcccttagt gagacttaat ttatttgttc gccgtaagtc gattttgaga    1200
tgcacatttc tccttaattt tccttttata gctgaccgtg cacggccttg aaacatcacg    1260
atcttttcag ttaaatttaa ttagcacggg ctaaattttt acattgcaaa agaaaataaa    1320
ctaatttcac acacacatat atagtatata gctagcaaac tgctaatggg ccagcaaaac    1380
ttatggatga taacattgag caatgaaatt attgtcatgt aacggtaact atattataat    1440
agtgagtttc gatccatgat ctaatatata ccatataata atattgatgc cacttggccc    1500
cacagacaaa gtagagtata gttcaagttt ggagatatat aaatgataat aataataata    1560
aagctgctca agatattttc attctggcga tccatgtctg tccacgatgg atcgacgata    1620
aaatactcgg tgtttattat aatggacagg gcgctttgtg gggcgattat tttatgttgt    1680
gttgtccctt tcatgattat ttattaaata taggacagaa gtccaagca aaacacatgt    1740 gccccaagca ataggggatat atagtgacat attgtgaaa tagttatata ttttggggga    1800
gaatcatgtg tcaggggatat tgtacaatag aaaaacattt cttagtatgt aggtcctcaa    1860
ctgcccctgt ttttttctctt attttttagca gatgttcgat ccacttccac aattccactt    1920
gcaggaataa tataataaat atagatatat atggtacata agctgtatgt aaaatccata    1980
```

```
taataatatt aatattacat tatataccto aacgaatcat ttctaaagct tttattaggt    2040
ataataaaaa gtaaatttat attttggtgc ttgtagctag gtgtggccgt gtggggcacg    2100
tgcaagcaac cttactcgtt ccacctccta tcttttgctc cactttgtaa ataatacata    2160
ttacagcgta aaactgtgta gaaagtatga ttttacggct atatacacgg tgtgctacga    2220
ctaaaagtta gggacgacct cacgccgata attggatgac agatttttt cctttgatat    2280
cttttcttct tggcatgcca aatcgaattc ctccctctgc ctttaatttc tatttgttag    2340
gattatatga aactatttcc acaagtatag ttagagactc aaattcagat actagaaatt    2400
aatgatggtt tacaagccat aaataaataa attaaaaata aacatattta gattttaatt    2460
tgaatgaaaa gagaacattg cttcggtttg atgcagatta acttatacag aaatcatata    2520
ttatgtcatg agagacaagc aaagattggt caacttatta ccatttcttg caaaatcaag    2580
tttgccgtat tattattttg tccttttctt ttttaaaaga ttattagctg gttattggtt    2640
ctctgggcag ttaacggggt agagtattcc acagaattaa ataatcacca tgcaaggaac    2700
acgcgttgtc ctctacatac gattctttat ttacttaatt ctacatcaca cattttgtgc    2760
aagaacagta gctattagaa aaaaatgtg agcatcggtt cacaaccggc tatagtactg    2820
gattatcaac tgatattaga caatcgaaat taaagacctt attttgaag gaccggtgaa    2880
atgaccagaa ggggtgaatt agagccaatc aaattttatt gttaaaaact taaatttaga    2940
ccttatttgt gaaggaccag aagaggtgaa tgagagccaa tcaaatttta ttacaaaaaa    3000
ctaaaattta gcacttaact tcaattgaga tgaagaaatc gttcaaacca gaagcacatc    3060
ggccaaatag taatcttacg atttcaaaat ggtacccta gatacatttg gttttttgtt    3120
tagaataccg gtattctttg gctaagttca tttggtttat tggttttgt ttagaatatg    3180
ggtattctaa acaaaaacca aatgaatttt gccaaagag atggatgtca ataaaagccc    3240
acatatctat ttatagaggt gatggataca tcatatccac ttagccgggg caaaatggat    3300
caactcctag gattttgatc agacgaccac gcgctctaca caaagttgct cgcctcgac    3360
acacccttttg tgatgatgtc atgtgccacc tctgattcct gccgaaaccg ccaccgtcaa    3420
gttttgaggc ccaaactcag caaaaccagc agatgggtgg ttttgaggct caaccacaaa    3480
accaccgcga gtagtgcatc gcatgcgcgt ccccacgtcc tggacacatg tcccattagt    3540
ccttgaccgc atcggcgaca gtgcgacaca agccactctg tcatgtcctc gcgctagtgc    3600
gtgtcctagg tgtgagccac cacaacttgt caaccggctc ctccgacccc ttggtcaagt    3660
cctagtgctc gtcttttcatc actctccgtc tatcggcata aaccctcgtg tgaccttcac    3720
attcgccatt gaacaacata catgtacttc acacctgcac accataagcc gagagacatg    3780
gttgcacaat acataactca tactctggtc agtccaccga ctacatcaaa atactatccg    3840
ttgacaatca cttatcatca actcgaacca caagggacaa atcaacttgt gttcacaatt    3900
gtttgccata gagagaaaga aagcgtactc cgtgtgttgc ttgggtttac cgagaagcac    3960
gtgtgtaaaa tgggtagcat actctagtag tactacgagt gcacgacgtg actcctacag    4020
attccaaact cttggcaaaa ttaatatcgc gacatgtcat catgtccatg ccattacctt    4080
agctgtattg acaggccgga cctgctattt gtgtcggccg tacgtgttct tgcggtcctc    4140
gtcgggtggg gtttcgctct ctgaatttc tgattggttc catcgatatt ttctgattgg    4200
ttccatcgaa agcgaaacca ggaccgtacg tggcgccaaa ttcaaccaga ccacccatcc    4260
cttcccgggg tcatgtcaca tccctgttgc ttcacgtttt cttacaaaat tacccgctcc    4320
gtccgtgaag caaatataac tatgatatcc ctatctgtca gagtagttta aatttaacta    4380
```

```
aatttataat aaacaatact cgctttggtc ctaaatctag acacatatat atatatatat    4440
atatatataa cacatacatc aagtattgta taaattcaca aaataccact atatgaacgc    4500
ccttaaattt taaattaaaa aattatctaa gaaaacataa gcaataatta acccatgcca    4560
atgcaagttg aatacttgaa ttgaaaaaag ttgattccag ctcagggaac ctataaccat    4620
ggcttcgcat gagttggcga ttgcctgaac aggcccatgc agagcaacta accatagaat    4680
agaacaatac gcgatgaaat tcaccgtacc ctgcaacgta atggatgtgt gattagtatc    4740
accggcacct cattttacc cgtcatctcg ttgtacctac attttcagaa acggtgatc      4800
acgacaaaga gcgtggagtt catgccattc ttcctgtcct tcttcctctt cctcaacgga    4860
ggcgtctggg caacgtacgc ggtgcttgac cgcgacatct tcctcggggt aatgtttaaa    4920
gcctctctgt tcttctcgat cttcttcccc aacctctgtc ttttccgcta cccatactaa    4980
acagaacctc tcgatcgctc tctgcatgca gatccccaat gggataggct tcgtgcttgg    5040
caccatccag ctgatcgtct acgcgatcta catgaacagc aaggcctccc aatgcagcaa    5100
agaaacagcg tcctcgcctc ttctggcctc cgaccgggga gaagcatcta gccatgtctg    5160
atgatgagct tcgatcagtg cgcgcgctgg agtatagcat agaagtctct tgctgtcaaa    5220
aacttccaag accaacggta cctaccagca tgcatgcatg caagaggtta ccaatttta    5280
ttgtttgaaa attcatgtaa acttgtgacc tccatggatt gtttctttct ttggtataag    5340
cttcgaagat gttagattgt tagcacggta gttttgccag agaagggtgt tgtcaatata    5400
atgaagaaat ggtgaaaatc catacatttg attatcga                            5438
```

<210> SEQ ID NO 5
<211> LENGTH: 3189
<212> TYPE: DNA
<213> ORGANISM: Zea mays

<400> SEQUENCE: 5

```
ctcaggagct aatgactcac ctctccgtgc tcacctcctc ttcttgaggc ttgagctctc      60
tcttcctctc tcccctcagc tcatctccac cgtctcccta tatataggat gctctgccgg     120
ctccaaggtt cccaagcgcc caaggcagcg gagagagcta gctccctcct cctcctcagg     180
tagcgagcga gcgagctcct ctgcccctct gcacacctgg cctccccttc tccgctgcag     240
gaccgccgtt gacgactgct ccaccagtac tgcgcgcgcc cgcgctgcct acccttacct     300
agccagagcg cggcgcgcga gagggagaac gaccaggagg ggaggagatc gatcgatcga     360
tcgatcgaga tagatggctt tcctcaacat ggagcagcag acctgggcct tcaccttcgg     420
tatcctaggt acatatatac tgtcagtctg tcactcgtag ctactaatta accgcatcaa     480
cggagccgcc ctgccgtctt cgtcctcgtc agtgtttctg cattgttttc cttccttgtc     540
ccaagtcctt tgagacgcac gcatacatga tacatgcatg gcatcatcgt ctcccaagtc     600
ctaggtacag tttcatcacc gcgcgcctct ctcagatatg tgtcgtcgta caggacaaca     660
caacacgtcc tcgtcaatct actagctata tgcgctaata accacctctt cctttccgag     720
ccacggcaca gtatagcctg ccatccgaac gaacggaacc gcccaaaacc caactttttt     780
tgggcctaac taatgcggtg gttagcccaa acaaagaaac cagggcagtc atacatttta     840
catgtagtac ctgcttgacg acgggaacca acacaacggc gcgccgcgag gagagtttgt     900
tccatttcct ccgcctgcag gctagctgca gctaataacc ccggccgccg gatgttctcc     960
ttctcgcatg ctttttttttt gggggggttct ttctccgcct cctgctcttc gtctgttcta   1020
```

| | |
|---|---|
| ccatcgtcga tcacacagca atttgactga ccgcgtctgt ccttccgacc ttgccgtttt | 1080 |
| gctttgcagg taacataatc tcgctgatgg tgttcctttc gccgctgtaa gtaactctct | 1140 |
| gctttaattt atttaaccta gccgtgaact tttcatattt acgtttacag tatccagtac | 1200 |
| catgcataat atactaccaa tatgtttcta tgtatattca gtaaagggaa gcgtccaaaa | 1260 |
| tatatactgc catcaggtat gatgagaaca tatatataaa gaacatggca cgcacgcatg | 1320 |
| cgtatctcac tgttgaatga atgacgtgcc atcatcgtcc atgctcttct agatccttt | 1380 |
| cctttaattt atgcgtggtt ctagatcccc ctatatatat atatatatat atatatatat | 1440 |
| atatatatat acgtacacct gaagacaaca tagctagcta ggaaataaac tcgttgggaa | 1500 |
| ttgaattgtc gcattaataa cgtcacttta atcagttgcg agccagtacg tgtcactgtt | 1560 |
| cggtggttgc gttgcacatg cttttagtat ggaacagcgc acgcaatcta gtaataatta | 1620 |
| atctaaaaaa tcacacggta aaaatattc gttcccgctg atcccgcgca ggccgacgtt | 1680 |
| ctaccgcgtg taccgcaaga agtcgacgga ggggttccag tcgacccgt acgtggtgac | 1740 |
| gctgttcagc tgcatgctgt ggatcttcta cgcgctgctc aagtccggcg ccgagctgct | 1800 |
| ggtgaccatc aacggcgtcg ggtgcgtgat cgaggcggcg tacctggccg cgtacctggt | 1860 |
| gtacgcgccc aaggccgcca gggcgctgac ggccaagatg ctgctggggc tcaacgtcgg | 1920 |
| cgtctttgga ctcgccgcgc tcgccaccat ggtggtctcc agcgccggcc tccgcgtgcg | 1980 |
| cgtgctcggc tggatctgcg tcagcgtcgc gctcagcgta ttcgccgcgc cgctcagcat | 2040 |
| catggcacgt atctaattta atctctctct ctctctctct ctctctctct ctctctctct | 2100 |
| ctctgaagag ggatgtgaat tgttggaacc gccattaatt cgctgactgc cctatctaca | 2160 |
| tctactttcc tgcagcggca ggtggtccgg accaagagcg tggagttcat gcccatctcg | 2220 |
| ctctccttct tcctggtgct gagcgccgtg atctggttcg cgtacggcgc gctgaagagg | 2280 |
| gacgtgttcg tggcgttccc caacgtgctg ggcttcgtct tcggcgtcgc gcagatagcg | 2340 |
| ctgtacatgg cgtacaggaa caaggagccc gcggcggtga cggtggagga ggcgaagctg | 2400 |
| ccggagcacg ccaaggaggt ggtggtggcc gcggcggcgg ccgaggccag ggcgagctgc | 2460 |
| ggtgctgagg tgcaccccat cgacatcgac atcgaagcta cgccgacgcc ggtggaggag | 2520 |
| gtgcacgagc cgcaggtggt cgtggtcgtc gacgtggacg tggagcctgt cacctgcgcc | 2580 |
| ggcgccgccg aggcagctgc gggagcaggg gcagatgcgt ccggcgtggc cgacggcggc | 2640 |
| gtccctggac ccatggcgcc gccggagcag ctggcgatca gcccgacat ggccatttcc | 2700 |
| gtggaggcgt aggttggtta aagtgtaata gcagagtgag tcgatatcga tcagtagtag | 2760 |
| atttgtcgag tcaaggaagg ggcctgctgc tgctgctacg cgacagcagc ggccagatgt | 2820 |
| actgcctgca tgcatgcagt ccctcccgtt gactcgaccc gtagagaagg gatgggatgg | 2880 |
| aagtagccgg gtccttgggc gagtagcggc gccttggcac ccacgggcca gccgtactgg | 2940 |
| cctgtgtgat gaaccggcga gagagatgag ataatgtgcg agcgagagag ggttggttgg | 3000 |
| gttgtggtag ttgaagaaga cggctagcta gctgctgctg ctgggctctc tatctgtctc | 3060 |
| tagatctgtg tatgtctgtg taatcgagga ttccctcacc ttgcatgccg cctcccttt | 3120 |
| gtgtccttct agtctgatga ttgttttcat tccatccatg ccggcgtcgc agtaataaaa | 3180 |
| ttttttggg | 3189 |

<210> SEQ ID NO 6
<211> LENGTH: 801
<212> TYPE: DNA
<213> ORGANISM: Zea mays

<400> SEQUENCE: 6

```
wttaytkrtm arcyamrtac kwtctmtgta cgyaygcagc ttccaaacat cctkgggttc      60
accttcggcg tggtccagat ggtgctctac gtgttgtaca tgaacaagac gccggtggcg     120
gcgactgccr agggyaagga tgccggcaag ctttcctcag ctgcagacga gcacgtcctc     180
gtcaacatcr ccaagctcag cccagccctc ccggagagga gctccggggt gyacccagtc     240
acccagatgg cgggmgttcc ygtyaggagc tgcgctgctg aagcaaccgc gccggckatg     300
ctgcccaaca gggacgtggt cgacgtcttc gtcasccgac acagccccgc cgtccacgtg     360
gcatagattc tcgatcgatc gsgtgcatgg cccatgcatg ygcccgcyac acgtacgcta     420
gmttttatat attcgaagga ckacttgctg ctggtcgtga gcatatatat gatggasraa     480
atrattaagt agtatatatr taagtaattr actrccatgs atggaagcta gstaatggat     540
ggaggcagag gycagarcga tgaaggggga agctatacat atatrtgygt aattaatata     600
gatatatggg mtttgtgtwc wtmtttgcwg ctatgtatta atttgcatgg rtatctgtta     660
ttccttttta tgtgtaacgt cttctaataa aatgtaattg aaccsacact acyrttgtta     720
gctaccacaa gtttcscraa aatggcttct rtgtgttcgg gcsggaaagc cctgrcccaa     780
agttgtcatc cggttcaryc a                                               801
```

<210> SEQ ID NO 7
<211> LENGTH: 801
<212> TYPE: DNA
<213> ORGANISM: Zea mays

<400> SEQUENCE: 7

```
gatggtgctc tacgtgttgt acatgaacaa gacgccggtg gcggcgactg ccragggyaa      60
ggatgccggc aagctttcct cagctgcaga cgagcacgtc ctcgtcaaca tcrccaagct     120
cagcccagcc ctcccggaga ggagctccgg ggtgyaccca gtcacccaga tggcgggmgt     180
tccygtyagg agctgcgctg ctgaagcaac cgcgccggck atgctgccca acagggacgt     240
ggtcgacgtc ttcgtcascc gacacagccc cgccgtccac gtggcataga ttctcgatcg     300
atcgsgtgca tggcccatgc atgygcccgc yacacgtacg ctagmttta tatattcgaa     360
ggackacttg ctgctggtcg tgagcatata tatgatggas raaatratta agtagtatat     420
atrtaagtaa ttractrcca tgsatggaag ctagstaatg gatggaggca gaggycagar     480
cgatgaaggg ggaagctata catatatrtg ygtaattaat atagatatat gggmtttgtg     540
twcwtmtttg cwgctatgta ttaatttgca tggrtatctg ttattccttt ttatgtgtaa     600
cgtcttctaa taaaatgtaa ttgaaccsac actacyrttg ttagctacca caagtttcsc     660
raaaatggct tctrtgtgtt cgggcsggaa agccctgrcc caaagttgtc atccggttca     720
rycacactag rtcccrgacr tytataaaag gagcctcaaa ttgctaagyt tcagtttttg     780
actccccacc cctataaatg a                                                801
```

<210> SEQ ID NO 8
<211> LENGTH: 801
<212> TYPE: DNA
<213> ORGANISM: Zea mays

<400> SEQUENCE: 8

```
tctgcgtcgg mttctcygtc agtgtcttcg tsgcgccact magcatcatg gtgagcyctg      60
agcacgcgta taaaactgtg ccaagatgca tggacgacag atygatcarc ccwrtcagtt     120
```

```
ttgatccatg tgtatcrttt ctaatgmrcc gtrtwtatat atgtgtgcag agacgmgtga    180
tccagacgaa gagcgtggag tacatgccct tctccctctc cctctcgctc accctcagcg    240
ccgtcgtctg gttcctctac ggcctcctca tcaaggacaa atacgtcgcg gtaattgttt    300
catctaatct gctgcarccg ycatggtatt ggtatctctc actkkycwtt aytkrtmarc    360
yamrtackwt ctmtgtacgy aygcagcttc caaacatcct kgggttcacc ttcggcgtgg    420
tccagatggt gctctacgtg ttgtacatga acaagacgcc ggtggcggcg actgccragg    480
gyaaggatgc cggcaagctt tcctcagctg cagacgagca cgtcctcgtc aacatcrcca    540
agctcagccc agccctcccg gagaggagct cggggtgya cccagtcacc cagatggcgg    600
gmgttccygt yaggagctgc gctgctgaag caaccgcgcc ggckatgctg cccaacaggg    660
acgtggtcga cgtcttcgtc asccgacaca gccccgccgt ccacgtggca tagattctcg    720
atcgatcgsg tgcatggccc atgcatgygc ccgcyacacg tacgctagmt tttatatatt    780
cgaaggacka cttgctgctg g                                              801

<210> SEQ ID NO 9
<211> LENGTH: 801
<212> TYPE: DNA
<213> ORGANISM: Zea mays

<400> SEQUENCE: 9
cgggmgttcc ygtyaggagc tgcgctgctg aagcaaccgc gccggckatg ctgcccaaca     60
gggacgtggt cgacgtcttc gtcasccgac acagccccgc cgtccacgtg gcatagattc    120
tcgatcgatc gsgtgcatgg cccatgcatg ygcccgcyac acgtacgcta gmttttatat    180
attcgaagga ckacttgctg ctggtcgtga gcatatatat gatggasraa atrattaagt    240
agtatatatr taagtaattr actrccatgs atggaagcta gstaatggat ggaggcagag    300
gycagarcga tgaaggggga agctatacat atatrtgygt aattaatata gatatatggg    360
mtttgtgtwc wtmtttgcwg ctatgtatta atttgcatgg rtatctgtta ttccttttta    420
tgtgtaacgt cttctaataa aatgtaattg aaccsacact acyrttgtta gctaccacaa    480
gtttcscraa aatggcttct rtgtgttcgg gcsggaaagc cctgrcccaa agttgtcatc    540
cggttcaryc acactagrtc ccrgacrtyt ataaaaggag cctcaaattg ctaagyttca    600
gtttttgact ccccacccct ataaatgagy gacarcgycc acccaracgc gagtgtggca    660
gcggttaccm gagagcgcga ggcgacgrca gttccccgag agcgaaaggc gacgrcgscc    720
agagactcgc gcgacygcga wgccaagcgc ggyggcggcc tcyagaggca ccayggggcgg    780 ctactcccag atyyggcggc g                                              801

<210> SEQ ID NO 10
<211> LENGTH: 501
<212> TYPE: DNA
<213> ORGANISM: Zea mays

<400> SEQUENCE: 10
tttcctcagc tgcagacgag cacgtcctcg tcaacatcgc caagctcagc ccagccctcc     60
cggagaggag ctccggggtg cacccagtca cccagatggc gggcgttcct gtcaggagct    120
gcgctgctga agcaaccgcg ccggcgatgc tgcccaacag ggacgtggtc gacgtcttcg    180
tcagccgaca cagccccgcc gtccacgtgg catagattct cgatcgatcg cgtgcatggc    240
ccatgcatgc gcccgccaca cgtacgctag cttttatata ttcgaaggac gacttgctgc    300
tggtcgtgag catatatatg atggagaaaa tgattaagta gtatatatat aagtaattaa    360
```

```
ctgccatgca tggaagctag ctaatggatg gaggcagagg ccagaacgat gaaggggaa      420 gctatacata tatgtgtgta attaatatag atatatgggc tttgtgttca tctttgcagc    480
tatgtattaa tttgcatgga t                                              501
```

<210> SEQ ID NO 11
<211> LENGTH: 801
<212> TYPE: DNA
<213> ORGANISM: Zea mays

<400> SEQUENCE: 11

```
tcgtctggtt cctctacggc ctcctcatca aggacaaata cgtcgcggta attgtttcat     60
ctaatctgct gcarccgyca tggtattggt atctctcact kkycwttayt krtmarcyam    120
rtackwtctm tgtacgyayg cagcttccaa acatcctkgg gttcaccttc ggcgtggtcc    180
agatggtgct ctacgtgttg tacatgaaca agacgccggt ggcggcgact gccragggya    240
aggatgccgg caagctttcc tcagctgcag acgagcacgt cctcgtcaac atcrccaagc    300
tcagcccagc cctcccggag aggagctccg ggtgyaccc agtcacccag atggcgggmg     360
ttccygtyag gagctgcgct gctgaagcaa ccgcgccggc katgctgccc aacagggacg    420
tggtcgacgt cttcgtcasc cgacacagcc ccgccgtcca cgtggcatag attctcgatc    480
gatcgsgtgc atgcccatg catgygcccg cyacacgtac gctagmtttt atatattcga    540
aggackactt gctgctggtc gtgagcatat atatgatgga sraaatratt aagtagtata    600
tatrtaagta attractrcc atgsatgaaa gctagstaat ggatggaggc agaggycaga    660
rcgatgaagg gggaagctat acatatatrt gygtaattaa tatagatata tgggmtttgt    720
gtwcwtmttt gcwgctatgt attaatttgc atggrtatct gttattcctt tttatgtgta    780
acgtcttcta ataaaatgta a                                              801
```

<210> SEQ ID NO 12
<211> LENGTH: 801
<212> TYPE: DNA
<213> ORGANISM: Zea mays

<400> SEQUENCE: 12

```
gacgckggca gtgaggaaya gaaggattca ggtrsgtgga atcaaaaact tacacaggcg     60
acaggaagag gaagagcgca atgacattcc ctggggagac agatcyaaca gagattaggc    120
gaggcaagaa gaagaccatc aggtaggcat gmarcagagg caggaatggc atggtgayac    180
tgaccagaaa ctccgaagaa gaacctggcg ataygctcca tctcttccgc ttcgygctta    240
tcgctgtgcg gaaccctcgg ctgtgctgsc ctggaacccg aacggagcag rggggtagt     300 gastggactg gastccttc ctccacggtc taggccsgga gcgcacccac acccaacgag    360
cagttagcta gtagctctca agtctgaayr gctgagcsca rcacacagca gccaagccaa    420
cgagcctgtg tacgggcggt gtctttgtgc ctgtgtgtca cccggtgcag cagggaacga    480
gcggtgtggc taatatataa ggagcagagg attgtgatct tgggaggtaa ggggtaggac    540
cggtggagaa gagrrcctgt tcgracggaa gcccatacgt tcttatcttc ttcttagctt    600
gtyagtcaaa gtrtagatgg ccatttggca ctaacacgat gggccggccc aggcayggca    660
cgaaaaagca cggtccaggc acgacccggt ccggttagta tagtgccagt gcctggcacg    720
gcacggctat agtgccgtgc ctgggccact atctcgaccc gtagtgctgg cacgggcacg    780
acacagttac atttttattt t                                              801
```

<210> SEQ ID NO 13
<211> LENGTH: 801
<212> TYPE: DNA
<213> ORGANISM: Zea mays

<400> SEQUENCE: 13

| | | | | | |
|---|---|---|---|---|---|
| gttcctccca | gtcccagaca | gcaaataagc | cttgcccgcc | tacacctggc | tggcgacctt | 60 |
| gccgtcgccg | ccgacggcgt | ccgcygcstt | gttggtcgtg | gcrtcggcca | gctccacggc | 120 |
| agcggccacc | ttcttggtgt | cctccacctc | cgcggcggcg | gcggcggcct | ctcccttgcc | 180 |
| ggccggcgcg | gcggggccct | tgttttttccg | gtagatggcg | tacaggatga | gctgcatcar | 240 |
| rcccaggaag | ctcccgcacc | cgttcggkat | ctrcamgcat | gcacagacag | cgcgggttta | 300 |
| gmgacastgg | ggstgtrcyg | aagtttgsac | sgcatgaatc | attccgacat | gatgagattt | 360 |
| gsaraaaaaa | aaarctcggc | ctwagatatt | tcatcgcagt | ytgtcgcgtt | ggtgtgtact | 420 |
| gaagtggagt | gcaccgtgca | gtttgctary | tagcattgcg | acaagaaaga | gcgcgggcgc | 480 |
| tgttgctyct | gcctgtgccg | ggtccaatcc | agctgcatgg | acatgggcac | ggcggcccat | 540 |
| cggcagctag | caccggcgtg | cgctgcctgt | gggtggccac | gcccacgctg | ctagacgcta | 600 |
| ccggcgccca | tgcccgtgca | tcggcwgcgg | cagcggcagg | catgtgcgcc | tggttgggyt | 660 |
| tgggcgggac | atcgaaaggg | caaccgacgc | ccagmccggg | ggtactgtgc | tggccagaty | 720 |
| agatgcagtt | acgtccagtc | ccaacagcta | gtgayacagt | rctgctrcag | tggtttccga | 780 |
| gtgccaawcg | gacaacmtgc | g | | | | 801 |

<210> SEQ ID NO 14
<211> LENGTH: 501
<212> TYPE: DNA
<213> ORGANISM: Zea mays

<400> SEQUENCE: 14

| | | | | | |
|---|---|---|---|---|---|
| cttggggtag | cctcctggga | gagatggaga | tgagagtaac | aacaaccgta | aaagcccaca | 60 |
| gaaaccaaca | ccaatctgct | ccaccgacaa | actaaggcag | cctcgtttag | gatgttcctc | 120 |
| ccagtcccag | acagcaaata | agccttgccc | gcctacacct | ggctggcgac | cttgccgtcg | 180 |
| ccgccgacgg | cgtccgctgc | cttgttggtc | gtggcatcgg | ccagctccac | ggcagcggcc | 240 |
| accttcttgg | tgtcctccac | ctccgcggcg | gcggcggcgg | cctctccctt | gccggccggc | 300 |
| gcggcggggc | ccttgttttt | ccggtagatg | gcgtacagga | tgagctgcat | caggcccagg | 360 |
| aagctcccgc | acccgttcgg | gatctgcacg | catgcacaga | cagcgcgggt | ttagcgacag | 420 |
| tgggggtgtg | ctgaagtttg | gaccgcatga | atcattccga | catgatgaga | tttgcaaaaa | 480 |
| aaaaaaactc | ggccttagat | a | | | | 501 |

<210> SEQ ID NO 15
<211> LENGTH: 501
<212> TYPE: DNA
<213> ORGANISM: Zea mays

<400> SEQUENCE: 15

| | | | | | |
|---|---|---|---|---|---|
| cctcctggga | gagatggaga | tgagagtaac | aacaaccgta | aaagcccaca | gaaaccaaca | 60 |
| ccaatctgct | ccaccgacaa | actaaggcag | cctcgtttag | gatgttcctc | ccagtcccag | 120 |
| acagcaaata | agccttgccc | gcctacacct | ggctggcgac | cttgccgtcg | ccgccgacgg | 180 |
| cgtccgctgc | cttgttggtc | gtggcatcgg | ccagctccac | ggcagcggcc | accttcttgg | 240 |
| tgtcctccac | ctccgcggcg | gcggcggcgg | cctctccctt | gccggccggc | gcggcggggc | 300 |

```
ccttgttttt ccggtagatg gcgtacagga tgagctgcat caggcccagg aagctcccgc      360
acccgttcgg gatctgcacg catgcacaga cagcgcgggt ttagcgacag tgggggtgtg      420
ctgaagtttg gaccgcatga atcattccga catgatgaga tttgcaaaaa aaaaaaactc      480
ggccttagat atttcatcgc a                                                501

<210> SEQ ID NO 16
<211> LENGTH: 501
<212> TYPE: DNA
<213> ORGANISM: Zea mays

<400> SEQUENCE: 16
ccgtaaaagc ccacagaaac caacaccaat ctgctccacc gacaaactaa ggcagcctcg       60
tttaggatgt tcctcccagt cccagacagc aaataagcct tgcccgccta cacctggctg      120
gcgaccttgc cgtcgccgcc gacggcgtcc gctgccttgt tggtcgtggc atcggccagc      180
tccacggcag cggccacctt cttggtgtcc tccacctccg cggcggcggc ggcggcctct      240
cccttgccgg ccggcgcggc ggggcccttg tttttccggt agatggcgta caggatgagc      300
tgcatcaggc ccaggaagct cccgcacccg ttcgggatct gcacgcatgc acagacagcg      360
cgggtttagc gacagtgggg gtgtgctgaa gtttggaccg catgaatcat tccgacatga      420
tgagatttgc aaaaaaaaaa aactcggcct tagatatttc atcgcagtct gtcgcgttgg      480
tgtgtactga agtggagtgc a                                                501

<210> SEQ ID NO 17
<211> LENGTH: 801
<212> TYPE: DNA
<213> ORGANISM: Zea mays

<400> SEQUENCE: 17
atgcaacatt agtttcttga gcagcaatga gagcataatg agctatacta tcaatgtcac       60
gayatcsatg tggcaaaaac aatattactt ctargtctrt cttgagcaat agagtgatta      120
ttgctwacag gaggtayaka agcttaawst gygtgaagat gaaaatcytr tagttgtyaa      180
agtcattatc tamtwtcaag ttsaagyatt rtcttgactt rgtargtgtt ygtggagctt      240
agcaccctag trgtgtttgg sgaggaaaca atttttataga ttaaatcaac attagtttct      300
tgattagtgt aaatatgctt attattatyt tttycttata kttatttgga cygactawak      360
ctagaactgc actcttttga tttgggyatt caagacrggc waaattaagc acacaaagaa      420
tatgttaagt ataaatagat gcatgccctg catgttacag tcttatcatc ttcccgtaga      480
gatctacgac gttgacacgg cgtacgtaga cgactacgya cgtaccgacc aagaccatca      540
caccacyata attattagca tgcattgtca gatccaatgc aaacaamagc tactactact      600
tgattcgaca ctgaastgaa ctgaactgac aagactacgc acacgagaga gacacgcaat      660
aataatccaa caattaacca actaaacgay caactagcag acgacgatgc ctgcatctgc      720
atgcttgagc tgccagccac ttgccaccaa actgtcgtac gtcrtccgag ctrgctaatr      780
agaagctagc agggtgtgta c                                                801

<210> SEQ ID NO 18
<211> LENGTH: 801
<212> TYPE: DNA
<213> ORGANISM: Zea mays

<400> SEQUENCE: 18
```

```
tawygttaac tygtrataay tgtraacttg ttataytrga atatttttat attwrtatgr      60
ttayygatcg tatttaaaat tmtgmtcrtt aymtgtgyat tttcygtmcc gaacytccaa     120
tattratact gtttccgttt ctaaagttac catwttttat ktmatttccg atataarata    180
traaaacrga cacaracaca gttggagcyg tgsaaccrak csgaccwcaa atctacrata    240
ctgcaaagca tgcgaggggc ctggtttgtg ttycctagaa gargattgsc tgmacttta    300 cactactaaa acaagcttcy ctygataatc aaakgtatgg attttcacca tttcttcatt    360
rtattgacaa cayccttctc tggcmaaact aycgtgctaa yaatctaaca tcttsgaagc    420
ttataccaaa graagaaaca atccatgrag gtcacaagtt tamatrartt ttcaaacaat    480
aaaaattggt aacctsttsc atgcatgcat gcwggtaggt accgttggtc tkggaagttt    540
tygacagcaa gagacttcta tgctatactc cagcgcgcgc actgawygaa gctcatcatc    600
agacatggct agaygcttct cccyggtcgg aggccakaag aggcgaggac gctgtttcyt    660
tgctgcattg ggaggccttg ctgttcatgt agatcgcgta gacgatcagc tggatggtgc    720
caagcacgaa gcctatccca ttggggatct gcaygcagag agcgatcgag aggttctgtt    780
tagtatgggt agcggaaaag a                                             801

<210> SEQ ID NO 19
<211> LENGTH: 501
<212> TYPE: DNA
<213> ORGANISM: Zea mays

<400> SEQUENCE: 19
atcccatccc ttctctacgg gtcgagtcaa cgggagggac tgcatgcatg caggcagtac     60
atctggccgc tgctgtcgcg tagcagcagc agcaggcccc ttccttgact cgacaaatct    120
actactgatc gatatcgact cactctgcta ttacacttta accaacctac gcctccacgg    180
aaatggccat gtcgggcttg atcgccagct gctccggcgg cgccatgggt ccagggacgc    240
cgccgtcggc cacgccggac gcatctgccc ctgctcccgc agctgcctcg gcggcgccgg    300
cgcaggtgac aggctccacg tccacgtcga cgaccacgac cacctgcggc tcgtgcacct    360
cctccaccgg cgtcggcgta gcttcgatgt cgatgtcgat ggggtgcacc tcagcaccgc    420
agctcgccct ggcctcggcc gccgccgcgg ccaccaccac ctccttggcg tgctccggca    480
gcttcgcctc ctccaccgtc a                                             501
```

GENETIC MARKERS ASSOCIATED WITH DROUGHT TOLERANCE IN MAIZE

CROSS REFERENCES TO RELATED APPLICATIONS

The presently disclosed subject matter claims the benefit of U.S. Provisional Patent Application Ser. No. 62/093,055, filed Dec. 17, 2014, the disclosure of which is incorporated herein by reference in its entirety.

FIELD OF THE INVENTION

The present invention relates to compositions and methods for identifying, selecting and/or producing maize plants having increased yield under non-drought conditions, increased yield stability under drought conditions, and/or increased drought tolerance.

STATEMENT REGARDING ELECTRONIC SUBMISSION OF A SEQUENCE LISTING

A Sequence Listing in ASCII text format, submitted under 37 C.F.R. § 1.821, entitled "80664-US-REG-ORG-NAT-1_Sequence_Listing_ST25", 38 kilobytes in size, generated Dec. 9, 2015 and filed via EFS-Web is provided in lieu of a paper copy. The Sequence Listing is hereby incorporated by reference into the specification for its disclosures.

BACKGROUND

A goal of plant breeding is to combine various desirable traits in a single plant. For field crops such as corn, these traits can include greater yield and better agronomic quality. However, genetic loci that influence yield and agronomic quality are not always known, and even if known, their contributions to such traits are frequently unclear. Thus, new loci that can positively influence such desirable traits need to be identified and/or the abilities of known loci to do so need to be discovered.

Once discovered, these desirable loci can be selected for as part of a breeding program in order to generate plants that carry desirable traits. An exemplary method for generating such plants includes the transfer by introgression of nucleic acid sequences from plants that have desirable genetic information into plants that do not by crossing the plants using traditional breeding techniques.

Desirable loci can be introgressed into commercially available plant varieties using marker-assisted selection (MAS) or marker-assisted breeding (MAB). MAS and MAB involves the use of one or more of the molecular markers for the identification and selection of those progeny plants that contain one or more loci that encode the desired traits. Such identification and selection can be based on selection of informative markers that are associated with desired traits. MAB can also be used to develop near-isogenic lines (NIL) harboring loci of interest, allowing a more detailed study of the effect each locus can have on a desired trait, and is also an effective method for development of backcross inbred line (BIL) populations.

Drought is one of the major limitations to maize production worldwide. Identifying genes that enhance the drought tolerance of maize may lead to more efficient crop production by allowing for the identification, selection and production of maize plants with improved water optimization traits and enhanced drought tolerance.

SUMMARY OF THE INVENTION

Compositions and methods for identifying, selecting and/or producing maize plants having increased yield under non-drought conditions, increased yield stability under drought conditions, and/or increased drought tolerance are provided. As described herein, a marker associated with increased yield under non-drought conditions, increased yield stability under drought conditions, and/or increased drought tolerance may comprise, consist essentially of or consist of a single allele or a combination of alleles at one or more genetic loci.

Accordingly, in some embodiments, a method of identifying, selecting and/or producing a maize plant having increased yield under non-drought conditions, increased yield stability under drought conditions, and/or increased drought tolerance is provided, comprising: detecting, in a maize plant or maize plant part, an allele of at least one marker locus that is associated with increased yield under non-drought conditions, increased yield stability under drought conditions, and/or increased drought tolerance in a maize plant, wherein said at least one marker locus is located within a chromosomal interval comprising (a) a chromosome interval on chromosome 10 defined by and including base pair (bp) position 14762443 to base pair (bp) position 14765098; (b) a chromosome interval on chromosome 10 defined by and including base pair (bp) position 14762443 to base pair (bp) position 14765012; (c) a chromosome interval on chromosome 10 defined by and including base pair (bp) position 14762443 to base pair (bp) position 14764839; (d) a chromosome interval on chromosome 10 defined by and including base pair (bp) position 14762443 to base pair (bp) position 14764763; (e) a chromosome interval on chromosome 10 defined by and including base pair (bp) position 14762443 to base pair (bp) position 14764762; (f) a chromosome interval on chromosome 10 defined by and including base pair (bp) position 14762443 to base pair (bp) position 14764658; (g) a chromosome interval on chromosome 10 defined by and including base pair (bp) position 14762443 to base pair (bp) position 14764415; (h) a chromosome interval on chromosome 10 defined by and including base pair (bp) position 14764415 to base pair (bp) position 14765098; (i) a chromosome interval on chromosome 10 defined by and including base pair (bp) position 14764415 to base pair (bp) position 14765012; (j) a chromosome interval on chromosome 10 defined by and including base pair (bp) position 14764415 to base pair (bp) position 14764839; (k) a chromosome interval on chromosome 10 defined by and including base pair (bp) position 14764415 to base pair (bp) position 14764763; (l) a chromosome interval on chromosome 10 defined by and including base pair (bp) position 14764415 to base pair (bp) position 14764762; (m) a chromosome interval on chromosome 10 defined by and including base pair (bp) position 14764415 to base pair (bp) position 14764658; (n) a chromosome interval on chromosome 10 defined by and including base pair (bp) position 14764658 to base pair (bp) position 14765098; (o) a chromosome interval on chromosome 10 defined by and including base pair (bp) position 14764658 to base pair (bp) position 14765012; (p) a chromosome interval on chromosome 10 defined by and including base pair (bp) position 14764658 to base pair (bp) position 14764839; (q) a chromosome interval on chromosome 10 defined by and including base pair (bp) position 14764658 to base pair (bp) position 14764763; (r) a chromosome interval on chromosome 10 defined by and including base pair (bp) position 14764658 to base pair (bp) position 14764762; (s) a chromosome interval on chromosome 10 defined by and including base pair (bp) position 14764762 to base pair (bp) position 14765098; (t) a chromosome interval on chromosome 10 defined by and including base pair (bp) position 14764762 to base pair (bp) position 14765012; (u) a chromosome interval on chromosome 10 defined by and including base pair (bp) position 14764762 to base pair (bp) position 14764839; (v) a chromosome interval on chromosome 10 defined by and including base pair (bp) position 14764762 to base pair (bp) position 14764763; (w) a chromosome interval on chromosome 10 defined by and including base pair (bp) position 14764763 to base pair (bp) position 14765098; (x) a chromosome interval on chromosome 10 defined by and including base pair (bp) position 14764763 to base pair (bp) position 14765012; (y) a chromosome interval on chromosome 10 defined by and including base pair (bp) position 14764763 to base pair (bp) position 14764839; (z) a chromosome interval on chromosome 10 defined by and including base pair (bp) position 14764839 to base pair (bp) position 14765098; (aa) a chromosome interval on chromosome 10 defined by and including base pair (bp) position 14764839 to base pair (bp) position 14765012; (bb) a chromosome interval on chromosome 3 defined by and including base pair (bp) position 171748815 to base pair (bp) position 171752467; (cc) a chromosome interval on chromosome 3 defined by and including base pair (bp) position 171748815 to base pair (bp) position 171752311; (dd) a chromosome interval on chromosome 3 defined by and including base pair (bp) position 171748815 to base pair (bp) position 171749536; (ee) a chromosome interval on chromosome 3 defined by and including base pair (bp) position 171748815 to base pair (bp) position 171749318; (ff) a chromosome interval on chromosome 3 defined by and including base pair (bp) position 171748815 to base pair (bp) position 171749283 (S_7767535); (gg) a chromosome interval on chromosome 3 defined by and including base pair (bp) position 171748815 to base pair (bp) position 171749273; (hh) a chromosome interval on chromosome 3 defined by and including base pair (bp) position 171749273 to base pair (bp) position 171752467; (ii) a chromosome interval on chromosome 3 defined by and including base pair (bp) position 171749273 to base pair (bp) position 171752311; (jj) a chromosome interval on chromosome 3 defined by and including base pair (bp) position 171749273 to base pair (bp) position 171749536; (kk) a chromosome interval on chromosome 3 defined by and including base pair (bp) position 171749273 to base pair (bp) position 171749318; (ll) a chromosome interval on chromosome 3 defined by and including base pair (bp) position 171749273 to base pair (bp) position 171749283; (mm) a chromosome interval on chromosome 3 defined by and including base pair (bp) position 171749283 to base pair (bp) position 171752467 (nn) a chromosome interval on chromosome 3 defined by and including base pair (bp) position 171749283 to base pair (bp) position 171752311; (oo) a chromosome interval on chromosome 3 defined by and including base pair (bp) position 171749283 to base pair (bp) position 171749536; (pp) a chromosome interval on chromosome 3 defined by and including base pair (bp) position 171749283 to base pair (bp) position 171749318; (qq) a chromosome interval on chromosome 3 defined by and including base pair (bp) position 171749318 to base pair (bp) position 171752467; (rr) a chromosome interval on chromosome 3 defined by and including base pair (bp) position 171749318 to base pair (bp) position 171752311; (ss) a chromosome interval on chromosome 3 defined by and including base pair (bp) position 171749318 to base pair (bp) position 171749536; (tt) a chromosome interval on chromosome 3 defined by and including base pair (bp) position 171749536 to base pair (bp) position 171752467; (uu) a chromosome interval on chromosome 3 defined by and including base pair (bp) position 171749536 to base pair (bp) position 171752311; (vv) a chromosome interval on chromosome 1 defined by and including base pair (bp) position 194932443 to base pair (bp) position 194935353; (ww) a chromosome interval on chromosome 8 defined by and including base pair (bp) position 33363546 to base pair (bp) position 33368983; (xx) a chromosome interval on chromosome 8 defined by and including base pair (bp) position 33363546 to base pair (bp) position 33363625; (yy) a chromosome interval on chromosome 8 defined by and including base pair (bp) position 33363625 to base pair (bp) position 33368983; (zz) a chromosome interval on chromosome 5 defined by and including base pair (bp) position 164854921 to base pair (bp) position 164858109; (aaa) a chromosome interval on chromosome 5 defined by and including base pair (bp) position 164854921 to base pair (bp) position 164855482 (S_25177407); (bbb) a chromosome interval on chromosome 5 defined by and including base pair (bp) position 164855482 to base pair (bp) position 164858109; or (ccc) any combination of (a) to (bbb) above, thereby identifying, selecting and/or producing a maize plant having increased yield under non-drought conditions, increased yield stability under drought conditions.

In some embodiments, a method of identifying, selecting and/or producing a maize plant having increased yield under non-drought conditions, increased yield stability under drought conditions, and/or increased drought tolerance is provided, comprising: detecting, in a maize plant or maize plant part, the presence of an allele of at least one marker locus associated with increased yield under non-drought conditions, increased yield stability under drought conditions, and/or increased drought tolerance in a maize plant, wherein said allele of at least one marker locus comprises: (a) a G allele at base pair (bp) position 14762443; (b) a C allele at base pair (bp) position 14765098; (c) an A allele at base pair (bp) position 14765012; (d) an A allele at base pair (bp) position 14764839; (e) a G allele at base pair (bp) position 14764763; (f) a C allele at base pair (bp) position 14764762; (g) a G allele at base pair (bp) position 14764658; (h) a G allele at base pair (bp) position 14764415; (i) a G allele at base pair (bp) position 171748815; (j) a C allele at base pair (bp) position 171752467; (k) a G allele at base pair (bp) position 171752311; (l) a C allele at base pair (bp) position 171749536; (m) an A allele at base pair (bp) position 171749318; (n) an A allele at base pair (bp) position 171749283; (o) a C allele at base pair (bp) position 171749273; (p) an A allele at base pair (bp) position 194932443; (q) a T allele at base pair (bp) position 194935353; (r) a C allele at base pair (bp) position 33363546; (s) an A allele at base pair (bp) position 33368983; (t) a T allele at base pair (bp) position 33363625; (u) a C allele at base pair (bp) position 164854921; (v) a G allele at base pair (bp) position 164858109; (x) an A allele at base pair (bp) position 164855482; or (y) any combination of (a) to (x) above, thereby identifying, selecting and/or producing a maize plant having increased yield under non-drought conditions, increased yield stability under drought conditions.

Accordingly, in some embodiments, a method of identifying, selecting and/or producing a maize plant having increased yield under non-drought conditions, increased yield stability under drought conditions, and/or increased drought tolerance is provided, comprising: detecting, in a maize plant or maize plant part, an allele of at least one marker locus that is associated with increased yield under non-drought conditions, increased yield stability under drought conditions, and/or increased drought tolerance in a maize plant, wherein said at least one marker comprises: "C" at a nucleotide position that corresponds to position 401 of SEQ ID NO: 6 (PZE1014822710), "A" at a nucleotide position that corresponds to position 401 of SEQ ID NO: 7 (PZE1014822787), "G" at a nucleotide position that corresponds to position 401 of SEQ ID NO: 8 (PZE1014822363), "A" at a nucleotide position that corresponds to position 401 of SEQ ID NO: 9 (PZE1014822960), "G" at a nucleotide position that corresponds to position 251 of SEQ ID NO: 10 (S_3355011), "G" at a nucleotide position that corresponds to position 401 of SEQ ID NO: 11 (PZE1014822606), "G" at a nucleotide position that corresponds to position 401 of SEQ ID NO: 12 (PZE03170079889), "C" allele at a nucleotide position that corresponds to position 401 of SEQ ID NO: 13 (PZE03170077114), "C" at a nucleotide position that corresponds to position 251 of SEQ ID NO: 14 (S_7767530), "A" at a nucleotide position that corresponds to position 251 of SEQ ID NO: 15 (S_7767535), "A" at a nucleotide position that corresponds to position 251 of SEQ ID NO: 16 (S_7767546), "A" at a nucleotide position that corresponds to position 401 of SEQ ID NO: 17 (PZE01194799632), "T" at a nucleotide position that corresponds to position 401 of SEQ ID NO: 18 (PZE0833363225), and "A" at a nucleotide position that corresponds to position 251 of SEQ ID NO: 19 (S_25177407).

In some embodiments, a method of selecting a maize plant or germplasm having increased yield under non-drought conditions, increased yield stability under drought conditions, and/or increased drought tolerance is provided, comprising crossing a first maize plant or germplasm with a second maize plant or germplasm, wherein said first maize plant or germplasm comprises within its genome a genetic marker associated with increased yield under non-drought conditions, increased yield stability under drought conditions, and/or increased drought tolerance in a maize plant, wherein said genetic marker comprises any of (a) to (y), above.

In some embodiments, a plant can be regenerated from a plant part in which said genetic marker(s) is/are detected.

Also provided herein are maize plants and maize plant parts produced, selected and/or identified by the methods of the invention, as well as crops comprising said maize plants, harvested products produced from said plants and crops, and post-harvest products produced from the harvested products.

These and other aspects of the invention are set forth in more detail in the description of the invention below.

BRIEF DESCRIPTION OF THE DRAWINGS

FIG. 1 provides the QQ plot generated to look at the observed distribution of −log 10(P-values) of the data a shown in Tables 2.1-2.4.

BRIEF DESCRIPTION OF THE SEQUENCE LISTING

SEQ ID NO.: 1 ZmSWEET13a [GRMZM2G173669]
  GRMZM2G173669 coord=10:14762443 . . . 14765098:1
SEQ ID NO.: 2 ZmSWEET1a [GRMZM2G039365]
  GRMZM2G039365 coord=3:171748815 . . . 171752467:-1
SEQ ID NO.: 3 ZmSWEET11/MtN3 [GRMZM2G368827]
  GRMZM2G368827 coord=1:194932443 . . . 194935353:-1
SEQ ID NO.: 4 ZmSWEET16b [GRMZM2G111926]
  GRMZM2G111926 coord=8:33363546 . . . 33368983:-1
SEQ ID NO.: 5 ZmSWEET15b [GRMZM5G872392]
  GRMZM5G872392 coord=5:164854921 . . . 164858109:-1
SEQ ID NO.: 6 PZE1014822710
  C/T SNP AT NUCLEOTIDE 401 identifies a favorable/unfavorable allele
SEQ ID NO.: 7 PZE1014822787
  A/G SNP AT NUCLEOTIDE 401 identifies a favorable/unfavorable allele
SEQ ID NO.: 8 PZE1014822363
  G/T SNP AT NUCLEOTIDE 401 identifies a favorable/unfavorable allele
SEQ ID NO.: 9 PZE1014822960
  A/G SNP AT NUCLEOTIDE 401 identifies a favorable/unfavorable allele
SEQ ID NO.: 10 S_3355011
  G/C SNP AT NUCLEOTIDE 251 identifies a favorable/unfavorable allele
SEQ ID NO.: 11 PZE1014822606
  G/T SNP AT NUCLEOTIDE 401 identifies a favorable/unfavorable allele
SEQ ID NO.: 12 PZE03170079889
  G/A SNP AT NUCLEOTIDE 401 identifies a favorable/unfavorable allele
SEQ ID NO.: 13 PZE03170077114
  C/T SNP AT NUCLEOTIDE 401 identifies a favorable/unfavorable allele
SEQ ID NO.: 14 S_7767530
  C/T SNP AT NUCLEOTIDE 251 identifies a favorable/unfavorable allele
SEQ ID NO.: 15 S_7767535
  A/C SNP AT NUCLEOTIDE 251 identifies a favorable/unfavorable allele
SEQ ID NO.: 16 S_7767546
  A/C SNP AT NUCLEOTIDE 251 identifies a favorable/unfavorable allele
SEQ ID NO.: 17 PZE01194799632
  A/T SNP AT NUCLEOTIDE 401 identifies a favorable/unfavorable allele
SEQ ID NO.: 18 PZE0833363225
  T/C SNP AT NUCLEOTIDE 401 identifies a favorable/unfavorable allele
SEQ ID NO.: 19 S_25177407
  A/C SNP AT NUCLEOTIDE 251 identifies a favorable/unfavorable allele

DETAILED DESCRIPTION

The present invention provides compositions and methods for identifying, selecting and/or producing maize plants having increased yield under non-drought conditions, increased yield stability under drought conditions, and/or increased drought tolerance, as well as maize plants, parts thereof, including but not limited to seeds, and maize germplasm, that are identified, selected and/or produced by methods of this invention. The present invention further provides an assay for the detection of increased yield under non-drought conditions, increased yield stability under drought conditions, and/or increased drought tolerance in a maize plant, plant part and/or maize germplasm. In addition, the present invention provides maize plants, plant parts, and/or germplasm having within their genome one or more SNP or QTL markers associated with increased yield under non-drought conditions, increased yield stability under drought conditions, and/or increased drought tolerance.

This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. Thus, the invention contemplates that in some embodiments of the invention, any feature or combination of features set forth herein can be excluded or omitted. In addition, numerous variations and additions to the various embodiments suggested herein will be apparent to those skilled in the art in light of the instant disclosure, which do not depart from the instant invention. Hence, the following descriptions are intended to illustrate some particular embodiments of the invention, and not to exhaustively specify all permutations, combinations and variations thereof.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

All publications, patent applications, patents and other references cited herein are incorporated by reference in their entireties for the teachings relevant to the sentence and/or paragraph in which the reference is presented. References to techniques employed herein are intended to refer to the techniques as commonly understood in the art, including variations on those techniques or substitutions of equivalent techniques that would be apparent to one of skill in the art.

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a composition comprises components A, B and C, it is specifically intended that any of A, B or C, or a combination thereof, can be omitted and disclaimed singularly or in any combination.

As used in the description of the invention and the appended claims, the singular forms "a," "an" and "the" are intended to include the plural forms as well, unless the context clearly indicates otherwise.

As used herein, "and/or" refers to and encompasses any and all possible combinations of one or more of the associated listed items, as well as the lack of combinations when interpreted in the alternative ("or").

The term "about," as used herein when referring to a measurable value such as a dosage or time period and the like, refers to variations of ±20%, ±10%, ±5%, ±1%, ±0.5%, or even ±0.1% of the specified amount.

As used herein, phrases such as "between X and Y" and "between about X and Y" should be interpreted to include X and Y. As used herein, phrases such as "between about X and Y" mean "between about X and about Y" and phrases such as "from about X to Y" mean "from about X to about Y."

The terms "comprise," "comprises" and "comprising" as used herein, specify the presence of the stated features, integers, steps, operations, elements, and/or components, but do not preclude the presence or addition of one or more other features, integers, steps, operations, elements, components, and/or groups thereof.

As used herein, the transitional phrase "consisting essentially of" means that the scope of a claim is to be interpreted to encompass the specified materials or steps recited in the claim and those that do not materially affect the basic and novel characteristic(s) of the claimed invention. Thus, the term "consisting essentially of" when used in a claim of this invention is not intended to be interpreted to be equivalent to "comprising."

As used herein, the term "allele" refers to one of two or more different nucleotides or nucleotide sequences that occur at a specific locus.

A "locus" is a position on a chromosome where a gene or marker or allele is located. In some embodiments, a locus may encompass one or more nucleotides.

As used herein, the terms "desired allele," "target allele" and/or "allele of interest" are used interchangeably to refer to an allele associated with a desired trait. In some embodiments, a desired allele may be associated with either an increase or a decrease (relative to a control) of or in a given trait, depending on the nature of the desired phenotype. In some embodiments of this invention, the phrase "desired allele," "target allele" or "allele of interest" refers to an allele(s) that is associated with increased yield under non-drought conditions, increased yield stability under drought conditions, and/or increased drought tolerance in a maize plant relative to a control maize plant not having the target allele or alleles. Thus, for example, a maize plant comprising one or more of the markers associated with increased yield under non-drought conditions, increased yield stability under drought conditions, and/or increased drought tolerance in a maize plant as described herein (e.g., desired alleles) can have increased yield under non-drought conditions, increased yield stability under drought conditions, and/or increased drought tolerance as compared to a maize plant that does not comprise said one or more markers associated with increased yield under non-drought conditions, increased yield stability under drought conditions, and/or increased drought tolerance (e.g., desired alleles).

A marker is "associated with" a trait when said trait is linked to the marker and when the presence of the marker is an indicator of whether and/or to what extent the desired trait or trait form will occur in a plant/germplasm comprising the marker. Similarly, a marker is "associated with" an allele or chromosome interval when it is linked to said allele or said chromosome interval and when the presence of the marker is an indicator of whether the allele or chromosome interval is present in a plant/germplasm comprising the marker. For example, "a marker associated with a drought tolerance allele" refers to a marker whose presence or absence can be used to predict whether a plant will display drought tolerance.

As used herein, the terms "backcross" and "backcrossing" refer to the process whereby a progeny plant is crossed back to one of its parents one or more times (e.g., 1, 2, 3, 4, 5, 6, 7, 8, 9, 10, or more.). In a backcrossing scheme, the "donor" parent refers to the parental plant with the desired gene or locus to be introgressed. The "recipient" parent (used one or more times) or "recurrent" parent (used two or more times) refers to the parental plant into which the gene or locus is being introgressed. For example, see Ragot, M. et al. *Marker-assisted Backcrossing: A Practical Example*, in TECHNIQUES ET UTILISATIONS DES MARQUEURS MOLECULAIRES LES COLLOQUES, Vol. 72, pp. 45-56 (1995); and Openshaw et al., *Marker-assisted Selection in Backcross Breeding*, in PRO- CEEDINGS OF THE SYMPOSIUM "ANALYSIS OF MOLECULAR MARKER DATA," pp. 41-43 (1994). The initial cross gives rise to the F1 generation. The term "BC1" refers to the second use of the recurrent parent, "BC2" refers to the third use of the recurrent parent, and so on. In some embodiments, the number of backcrosses can be about 1 to about 10 (e.g., 1, 2, 3, 4, 5, 6, 7, 8, 9, 10). In some embodiments, the number of backcrosses is about 7.

As used herein, a "control" maize plant means a maize plant which does not comprise said marker or markers of the invention, wherein said control maize plant is grown under the same environmental conditions as the identified, selected, produced, introgressed maize plant. In some embodiments, the control maize plant can have a substantially similar genetic background (e.g., 70%, 75%, 80%, 85%, 90%, 91%, 92%, 93%, 94%, 95%, 96%, 97%, 98%, 99%, or more) to the identified, selected, produced, introgressed plant. In some embodiments, the control plant is of the same elite line as that of the identified, selected, produced, introgressed plant but does not comprise said marker or markers of the invention.

As used herein, the terms "cross" or "crossed" refer to the fusion of gametes via pollination to produce progeny (e.g., cells, seeds or plants). The term encompasses both sexual crosses (the pollination of one plant by another) and selfing (self-pollination, e.g., when the pollen and ovule are from the same plant). The term "crossing" refers to the act of the gametes fusing via pollination to produce progeny.

As used herein, the terms "cultivar" and "variety" refer to a group of similar plants that by structural or genetic features and/or performance can be distinguished from other cultivars or varieties within the same species.

As used herein, the terms "drought tolerance" and "drought tolerant" refer to a plant's ability to endure and/or thrive under drought stress conditions. When used in reference to a plant part, the terms refer to the ability of a plant that arises from that plant part to endure and/or thrive under drought conditions. In general, a plant or plant part is designated as "drought tolerant" if it displays "increased drought tolerance." This can be measured in terms of a single plant or in terms of the results from a group of the drought tolerant plants of this invention. Thus, for example, when measuring yield, the measurements are made on a group of the plants of the invention, which is then compared to the yield of a group of appropriate control plants.

In some embodiments, as used herein, the term "increased drought tolerance" or "enhanced drought tolerance" refers to an improvement in one or more water optimization traits as compared to one or more controls (e.g., one or both parents, or a plant lacking a marker associated with drought tolerance when grown under the same environmental conditions). Exemplary water optimization traits include, but are not limited to, water loss, accumulation of reactive oxygen species, accumulation of dehydrins, root architecture, accumulation of late embryogenesis abundant proteins, grain yield at standard moisture percentage (YGSMN), grain moisture at harvest (GMSTP), grain weight per plot (GWTPN), percent yield recovery (PYREC), yield reduction (YRED), and percent barren (PB). Thus, a plant that exhibits decreased water loss, decreased accumulation of reactive oxygen species, increased accumulation of dehydrins, improved root architecture, increased accumulation of late embryogenesis abundant proteins, increased grain yield at standard moisture percentage (YGSMN), increased grain moisture at harvest (GMSTP), increased grain weight per plot (GWTPN), increased percent yield recovery (PYREC), decreased yield reduction (YRED), and/or decreased percent barren (PB) as compared to a control plant when each is grown under the same drought stress conditions displays enhanced or increased drought tolerance and may be designated as "drought tolerant."

As used herein, "increased yield" means increased grain yield at standard moisture percentage (YGSMN) in a plant or plants of this invention as compared to a control.

As used herein, "yield stability" refers to a difference in the relative rank of a plant line under well-watered versus drought conditions. "Increased yield stability" means that there is less change in rank for the plant line in the two conditions as compared to a control.

As used herein, "drought conditions" refers to water deprived conditions that result in a loss in yield of 30% or more versus well-watered conditions.

As used herein, "non-drought conditions" means that the plants are well watered.

As used herein, the terms "elite" and/or "elite line" refer to any line that is substantially homozygous and has resulted from breeding and selection for desirable agronomic performance.

As used herein, the terms "exotic," "exotic line" and "exotic germplasm" refer to any plant, line or germplasm that is not elite. In general, exotic plants/germplasms are not derived from any known elite plant or germplasm, but rather are selected to introduce one or more desired genetic elements into a breeding program (e.g., to introduce novel alleles into a breeding program).

A "genetic map" is a description of genetic linkage relationships among loci on one or more chromosomes within a given species, generally depicted in a diagrammatic or tabular form. For each genetic map, distances between loci are measured by the recombination frequencies between them. Recombination between loci can be detected using a variety of markers. A genetic map is a product of the mapping population, types of markers used, and the polymorphic potential of each marker between different populations. The order and genetic distances between loci can differ from one genetic map to another.

As used herein, the term "genotype" refers to the genetic constitution of an individual (or group of individuals) at one or more genetic loci, as contrasted with the observable and/or detectable and/or manifested trait (the phenotype). Genotype is defined by the allele(s) of one or more known loci that the individual has inherited from its parents. The term genotype can be used to refer to an individual's genetic constitution at a single locus, at multiple loci, or more generally, the term genotype can be used to refer to an individual's genetic make up for all the genes in its genome. Genotypes can be indirectly characterized, e.g., using markers and/or directly characterized by, e.g., nucleic acid sequencing.

As used herein, the term "germplasm" refers to genetic material of or from an individual (e.g., a plant), a group of individuals (e.g., a plant line, variety or family), or a clone derived from a line, variety, species, or culture. The germplasm can be part of an organism or cell, or can be separate from the organism or cell. In general, germplasm provides genetic material with a specific genetic makeup that provides a foundation for some or all of the hereditary qualities of an organism or cell culture. As used herein, germplasm includes cells, seed or tissues from which new plants may be grown, as well as plant parts that can be cultured into a whole plant (e.g., leaves, stems, buds, roots, pollen, cells, etc.). In some embodiments, germplasm includes but is not limited to tissue culture.

A "haplotype" is the genotype of an individual at a plurality of genetic loci, i.e., a combination of alleles. Typically, the genetic loci that define a haplotype are physically and genetically linked, i.e., on the same chromosome segment. The term "haplotype" can refer to polymorphisms at a particular locus, such as a single marker locus, or polymorphisms at multiple loci along a chromosomal segment.

As used herein, the term "heterozygous" refers to a genetic status wherein different alleles reside at corresponding loci on homologous chromosomes.

As used herein, the term "homozygous" refers to a genetic status wherein identical alleles reside at corresponding loci on homologous chromosomes.

As used herein, the term "hybrid" in the context of plant breeding refers to a plant that is the offspring of genetically dissimilar parents produced by crossing plants of different lines or breeds or species, including but not limited to a cross between two inbred lines.

As used herein, the term "inbred" refers to a substantially homozygous plant or variety. The term may refer to a plant or plant variety that is substantially homozygous throughout the entire genome or that is substantially homozygous with respect to a portion of the genome that is of particular interest.

The terms "increase," "increasing," "increased," "enhance," "enhanced," "enhancing," and "enhancement" (and grammatical variations thereof), as used herein, describe an elevation, for example, in yield, yield stability or the tolerance of a plant to drought by the introduction of a genetic marker(s) of the invention into the plant, thereby producing a plant having, for example, increased yield, yield stability, and/or drought tolerance (e.g., an elevation of at least about 20%, 25%, 30%, 35%, 40%, 45%, 50%, 75%, 100%, 125%, 150%, 175%, 200%, 350%, 300%, 350%, 400%, 450%, 500% or more). This increase can be observed by comparing the yield, yield stability, and/or drought tolerance of the plant comprising the genetic marker(s) of the invention to the yield, yield stability, and/or drought tolerance of a plant lacking said genetic marker(s) of the invention (i.e., a control).

As used herein, the terms "introgression," "introgressing" and "introgressed" refer to both the natural and artificial transmission of a desired allele or combination of desired alleles of a genetic locus or genetic loci from one genetic background to another. For example, a desired allele at a specified locus can be transmitted to at least one progeny via a sexual cross between two parents of the same species, where at least one of the parents has the desired allele in its genome. Alternatively, for example, transmission of an allele can occur by recombination between two donor genomes, e.g., in a fused protoplast, where at least one of the donor protoplasts has the desired allele in its genome. The desired allele may be a selected allele of a marker, a QTL, a transgene, or the like. Offspring comprising the desired allele can be backcrossed one or more times (e.g., 1, 2, 3, 4, 5, 6, 7, 8, 9, 10 or more times) to a line having a desired genetic background, selecting for the desired allele, with the result being that the desired allele becomes fixed in the desired genetic background. For example, a marker associated with increased yield under non-drought conditions, increased yield stability under drought conditions, and/or increased drought tolerance may be introgressed from a donor into a recurrent parent that is drought sensitive or does not comprise said marker(s) associated with increased yield under non-drought conditions, increased yield stability under drought conditions, and/or increased drought tolerance. The resulting offspring could then be backcrossed one or more times and selected until the progeny comprises the genetic marker(s) associated with increased yield under non-drought conditions, increased yield stability under drought conditions, and/or increased drought tolerance in the recurrent parent background.

As used herein, the term "linkage" refers to the degree with which one marker locus is associated with another marker locus or some other locus. The linkage relationship between a genetic marker and a phenotype may be given as a "probability" or "adjusted probability." Linkage can be expressed as a desired limit or range. For example, in some embodiments, any marker is linked (genetically and physically) to any other marker when the markers are separated by less than about 50, 40, 30, 25, 20, or 15 map units (or cM).

A centimorgan ("cM") or a genetic map unit (m.u.) is a unit of measure of recombination frequency and is defined as the distance between genes for which one product of meiosis in 100 is recombinant. One cM is equal to a 1% chance that a marker at one genetic locus will be separated from a marker at a second locus due to crossing over in a single generation. Thus, a recombinant frequency (RF) of 1% is equivalent to 1 map unit (m.u.).

As used herein, the phrase "linkage group" refers to all of the genes or genetic traits that are located on the same chromosome. Within the linkage group, those loci that are close enough together can exhibit linkage in genetic crosses. Since the probability of crossover increases with the physical distance between loci on a chromosome, loci for which the locations are far removed from each other within a linkage group might not exhibit any detectable linkage in direct genetic tests. The term "linkage group" is mostly used to refer to genetic loci that exhibit linked behavior in genetic systems where chromosomal assignments have not yet been made. Thus, the term "linkage group" is synonymous with the physical entity of a chromosome, although one of ordinary skill in the art will understand that a linkage group can also be defined as corresponding to a region of (i.e., less than the entirety) of a given chromosome.

As used herein, the term "linkage disequilibrium" refers to a non-random segregation of genetic loci or traits (or both). In either case, linkage disequilibrium implies that the relevant loci are within sufficient physical proximity along a length of a chromosome so that they segregate together with greater than random (i.e., non-random) frequency (in the case of co-segregating traits, the loci that underlie the traits are in sufficient proximity to each other). Markers that show linkage disequilibrium are considered linked. Linked loci co-segregate more than 50% of the time, e.g., from about 51% to about 100% of the time. In other words, two markers that co-segregate have a recombination frequency of less than 50% (and, by definition, are separated by less than 50 cM on the same chromosome). As used herein, linkage can be between two markers, or alternatively between a marker and a phenotype. A marker locus can be "associated with" (linked to) a trait, e.g., increased yield under non-drought conditions, increased yield stability under drought conditions, and/or increased drought tolerance. The degree of linkage of a genetic marker to a phenotypic trait is measured, e.g., as a statistical probability of co-segregation of that marker with the phenotype.

Linkage disequilibrium is most commonly assessed using the measure $r^2$, which is calculated using the formula described by Hill and Robertson, *Theor. Appl. Genet.* 38:226 (1968). When $r^2=1$, complete linkage disequilibrium exists between the two marker loci, meaning that the markers have not been separated by recombination and have the same allele frequency. Values for $r^2$ above ⅓ indicate sufficiently strong linkage disequilibrium to be useful for mapping. Ardlie et al., *Nature Reviews Genetics* 3:299 (2002). Hence, alleles are in linkage disequilibrium when $r^2$ values between pairwise marker loci are greater than or equal to about 0.3, 0.4, 0.5, 0.6, 0.7, 0.8, 0.9, or 1.0.

As used herein, the term "linkage equilibrium" describes a situation where two markers independently segregate, i.e., sort among progeny randomly. Markers that show linkage equilibrium are considered unlinked (whether or not they lie on the same chromosome).

As used herein, the terms "marker" and "genetic marker" are used interchangeably to refer to a nucleotide and/or a nucleotide sequence that has been associated with a phenotype and/or trait. A marker may be, but is not limited to, an allele, a gene, a haplotype, a chromosome interval, a restriction fragment length polymorphism (RFLP), a simple sequence repeat (SSR), a random amplified polymorphic DNA (RAPD), a cleaved amplified polymorphic sequence (CAPS) (Rafalski and Tingey, *Trends in Genetics* 9:275 (1993)), an amplified fragment length polymorphism (AFLP) (Vos et al., *Nucleic Acids Res.* 23:4407 (1995)), a single nucleotide polymorphism (SNP) (Brookes, *Gene* 234:177 (1993)), a sequence-characterized amplified region (SCAR) (Paran and Michelmore, *Theor. Appl. Genet.* 85:985 (1993)), a sequence-tagged site (STS) (Onozaki et al., *Euphytica* 138:255 (2004)), a single-stranded conformation polymorphism (SSCP) (Orita et al., *Proc. Natl. Acad. Sci. USA* 86:2766 (1989)), an inter-simple sequence repeat (ISSR) (Blair et al., *Theor. Appl. Genet.* 98:780 (1999)), an inter-retrotransposon amplified polymorphism (TRAP), a retrotransposon-microsatellite amplified polymorphism (REMAP) (Kalendar et al., *Theor. Appl. Genet.* 98:704 (1999)), an isozyme marker, an RNA cleavage product (such as a Lynx tag) or any combination of the markers described herein. A marker may be present in genomic or expressed nucleic acids (e.g., ESTs). A large number of maize genetic markers are known in the art, and are published or available from various sources, such as the MaizeGDB internet resource (maizegdb.org). In some embodiments, a genetic marker of this invention is a SNP allele, a SNP allele located in a chromosome interval and/or a haplotype (combination of SNP alleles), each of which is associated with increased yield under non-drought conditions, increased yield stability under drought conditions, and/or increased drought tolerance.

Markers corresponding to genetic polymorphisms between members of a population can be detected by methods well-established in the art. These include, but are not limited to, nucleic acid sequencing, hybridization methods, amplification methods (e.g., PCR-based sequence specific amplification methods), detection of restriction fragment length polymorphisms (RFLP), detection of isozyme markers, detection of polynucleotide polymorphisms by allele specific hybridization (ASH), detection of amplified variable sequences of the plant genome, detection of self-sustained sequence replication, detection of simple sequence repeats (SSRs), detection of randomly amplified polymorphic DNA (RAPD), detection of single nucleotide polymorphisms (SNPs), and/or detection of amplified fragment length polymorphisms (AFLPs). Thus, in some embodiments of this invention, such well known methods can be used to detect the SNP alleles as defined herein (See, e.g., Table 1).

Accordingly, in some embodiments of this invention, a marker is detected by amplifying a maize nucleic acid with two oligonucleotide primers by, for example, an amplification reaction such as the polymerase chain reaction (PCR).

A "marker allele," also described as an "allele of a marker locus," can refer to one of a plurality of polymorphic nucleotides found at a marker locus in a population that is polymorphic for the marker locus.

"Marker-assisted selection" (MAS) is a process by which phenotypes are selected based on marker genotypes. Marker assisted selection includes the use of marker genotypes for identifying plants for inclusion in and/or removal from a breeding program or planting.

As used herein, the terms "marker locus" and "marker loci" refer to a specific chromosome location or locations in the genome of an organism where a specific marker or markers can be found. A marker locus can be used to track the presence of a second linked locus, e.g., a linked locus that encodes or contributes to expression of a phenotypic trait. For example, a marker locus can be used to monitor segregation of alleles at a locus, such as a QTL or single gene, that are genetically or physically linked to the marker locus.

As used herein, the term "percent barren" (PB) refers to the percentage of plants in a given area (e.g., plot) with no grain. It is typically expressed in terms of the percentage of plants per plot and can be calculated as:

$$\frac{\text{number of plants in the plot with no grain}}{\text{total number of plants in the plot}} \times 100$$

As used herein, the term "percent yield recovery" (PYREC) refers to the effect an allele and/or combination of alleles has on the yield of a plant grown under stress conditions (e.g., drought conditions) as compared to that of a plant that is genetically identical except insofar as it lacks the allele and/or combination of alleles. PYREC is calculated as:

{1−[yield under full irrigation (w/ allele(s) of interest)−yield under drought conditions (w/ allele(s) of interest)]/[yield under full irrigation (w/out allele(s) of interest)−yield under drought conditions (w/out allele(s) of interest)]}×100

By way of example and not limitation, if a control plant yields 200 bushels under full irrigation conditions, but yields only 100 bushels under drought stress conditions, then its percentage yield loss would be calculated at 50%. If an otherwise genetically identical hybrid that contains the allele(s) of interest yields 125 bushels under drought stress conditions and 200 bushels under full irrigation conditions, then the percentage yield loss would be calculated as 37.5% and the PYREC would be calculated as 25% [(1.00−(200−125)/(200−100))×100].

As used herein, the term "water optimization trait" refers to any trait that can be shown to influence the yield of a plant under different sets of growth conditions related to water availability.

As used herein, the term "yield reduction" (YD) refers to the degree to which yield is reduced in plants grown under stress conditions. YD is calculated as:

$$\frac{\text{yield under non-stress conditions} - \text{yield under stress conditions}}{\text{yield under non-stress conditions}} \times 100$$

As used herein, the term "probe" refers to a single-stranded oligonucleotide sequence that will form a hydrogen-bonded duplex with a complementary sequence in a target nucleic acid sequence analyte or its cDNA derivative. Thus, a "marker probe" and "probe" refers to a nucleotide sequence or nucleic acid molecule that can be used to detect the presence of one or more particular alleles within a marker locus (e.g., a nucleic acid probe that is complementary to all of or a portion of the marker or marker locus, through nucleic acid hybridization). Marker probes comprising about 8, 10, 15, 20, 30, 40, 50, 60, 70, 80, 90, 100 or more contiguous nucleotides may be used for nucleic acid hybridization. Alternatively, in some aspects, a marker probe refers to a probe of any type that is able to distinguish (i.e., genotype) the particular allele that is present at a marker locus. Based on the guidance provided herein, the nucleotide sequences of the genes (e.g., SEQ ID NO:1 (Gene Model ID No: GRMZM2G173669); SEQ ID NO:2 (Gene Model ID No: GRMZM2G039365); SEQ ID NO:3 (Gene Model ID No: GRMZM2G368827); SEQ ID NO:4 Gene Model ID No: GRMZM2G111926); SEQ ID NO:5 (Gene Model ID No: GRMZM2G872392) and the location of the SNPs therein, probes can be readily developed for detecting the markers of this invention.

As used herein, the term "molecular marker" may be used to refer to a genetic marker, as defined above, or an encoded product thereof (e.g., a protein) used as a point of reference when identifying a linked locus. A molecular marker can be derived from genomic nucleotide sequences or from expressed nucleotide sequences (e.g., from a spliced RNA, a cDNA, etc.). The term also refers to nucleotide sequences complementary to or flanking the marker sequences, such as nucleotide sequences used as probes and/or primers capable of amplifying the marker sequence. Nucleotide sequences are "complementary" when they specifically hybridize in solution, e.g., according to Watson-Crick base pairing rules.

As used herein, the term "primer" refers to an oligonucleotide which is capable of annealing to a nucleic acid target and serving as a point of initiation of DNA synthesis when placed under conditions in which synthesis of a primer extension product is induced (e.g., in the presence of nucleotides and an agent for polymerization such as DNA polymerase and at a suitable temperature and pH). A primer (in some embodiments an extension primer and in some embodiments an amplification primer) is in some embodiments single stranded for maximum efficiency in extension and/or amplification. In some embodiments, the primer is an oligodeoxyribonucleotide. A primer is typically sufficiently long to prime the synthesis of extension and/or amplification products in the presence of the agent for polymerization. The minimum length of the primer can depend on many factors, including, but not limited to temperature and composition (A/T vs. G/C content) of the primer. In the context of amplification primers, these are typically provided as a pair of bi-directional primers consisting of one forward and one reverse primer or provided as a pair of forward primers as commonly used in the art of DNA amplification such as in PCR amplification. As such, it will be understood that the term "primer," as used herein, can refer to more than one primer, particularly in the case where there is some ambiguity in the information regarding the terminal sequence(s) of the target region to be amplified. Hence, a "primer" can include a collection of primer oligonucleotides containing sequences representing the possible variations in the sequence or includes nucleotides which allow a typical base pairing.

Primers can be prepared by any suitable method. Methods for preparing oligonucleotides of specific sequence are known in the art, and include, for example, cloning and restriction of appropriate sequences and direct chemical synthesis. Chemical synthesis methods can include, for example, the phospho di- or tri-ester method, the diethylphosphoramidate method and the solid support method disclosed in U.S. Pat. No. 4,458,066.

Primers can be labeled, if desired, by incorporating detectable moieties by for instance spectroscopic, fluorescence, photochemical, biochemical, immunochemical, or chemical moieties.

Based on the guidance provided herein, the nucleotide sequences of the genes (e.g., SEQ ID NO:1 (Gene Model ID No: GRMZM2G173669); SEQ ID NO:2 (Gene Model ID No: GRMZM2G039365); SEQ ID NO:3 (Gene Model ID No: GRMZM2G368827); SEQ ID NO:4 Gene Model ID No: GRMZM2G111926); SEQ ID NO:5 (Gene Model ID No: GRMZM2G872392) and the location of the SNPs therein, probes can be readily developed for detecting the markers of this invention. Particular nucleotides that are present at particular locations in the markers and nucleic acids disclosed herein can be determined using standard molecular biology techniques including, but not limited to amplification of genomic DNA from plants and subsequent sequencing. Additionally, oligonucleotide primers can be designed that would be expected to specifically hybridize to particular sequences that include the polymorphisms disclosed herein. For example, oligonucleotides can be designed to distinguish between the "C" allele and the "T" allele at a nucleotide position that corresponds to position 401 of SEQ ID NO: 6 (PZE1014822710). For example, oligonucleotides can be designed to distinguish between the "A" allele and the "G" allele at a nucleotide position that corresponds to position 401 of SEQ ID NO: 7 (PZE1014822787). For example, oligonucleotides can be designed to distinguish between the "G" allele and the "T" allele at a nucleotide position that corresponds to position 401 of SEQ ID NO: 8 (PZE1014822363). For example, oligonucleotides can be designed to distinguish between the "A" allele and the "G" allele at a nucleotide position that corresponds to position 401 of SEQ ID NO: 9 (PZE1014822960). For example, oligonucleotides can be designed to distinguish between the "G" allele and the "C" allele at a nucleotide position that corresponds to position 251 of SEQ ID NO: 10 (S_3355011). For example, oligonucleotides can be designed to distinguish between the "G" allele and the "T" allele at a nucleotide position that corresponds to position 401 of SEQ ID NO: 11 (PZE1014822606). For example, oligonucleotides can be designed to distinguish between the "G" allele and the "A" allele at a nucleotide position that corresponds to position 401 of SEQ ID NO: 12 (PZE03170079889). For example, oligonucleotides can be designed to distinguish between the "C" allele and the "T" allele at a nucleotide position that corresponds to position 401 of SEQ ID NO: 13 (PZE03170077114). For example, oligonucleotides can be designed to distinguish between the "C" allele and the "T" allele at a nucleotide position that corresponds to position 251 of SEQ ID NO: 14 (S_7767530). For example, oligonucleotides can be designed to distinguish between the "A" allele and the "C" allele at a nucleotide position that corresponds to position 251 of SEQ ID NO: 15 (S_7767535). For example, oligonucleotides can be designed to distinguish between the "A" allele and the "C" allele at a nucleotide position that corresponds to position 251 of SEQ ID NO: 16 (S_7767546). For example, oligonucleotides can be designed to distinguish between the "A" allele and the "T" allele at a nucleotide position that corresponds to position 401 of SEQ ID NO: 17 (PZE01194799632). For example, oligonucleotides can be designed to distinguish between the "T" allele and the "C" allele at a nucleotide position that corresponds to position 401 of SEQ ID NO: 18 (PZE0833363225). For example, oligonucleotides can be designed to distinguish between the "A" allele and the "C" allele at a nucleotide position that corresponds to position 251 of SEQ ID NO: 19 (S_25177407).

The PCR method is well described in handbooks and known to the skilled person. After amplification by PCR, target polynucleotides can be detected by hybridization with a probe polynucleotide, which forms a stable hybrid with the target sequence under stringent to moderately stringent hybridization and wash conditions. If it is expected that the probes are essentially completely complementary (i.e., about 99% or greater) to the target sequence, stringent conditions can be used. If some mismatching is expected, for example if variant strains are expected with the result that the probe will not be completely complementary, the stringency of hybridization can be reduced. In some embodiments, conditions are chosen to rule out non-specific/adventitious binding. Conditions that affect hybridization, and that select against non-specific binding are known in the art, and are described in, for example, Sambrook & Russell (2001). *Molecular Cloning: A Laboratory Manual, Third Edition*, Cold Spring Harbor Laboratory Press, Cold Spring Harbor, N.Y., United States of America. Generally, lower salt concentration and higher temperature hybridization and/or washes increase the stringency of hybridization conditions.

Different nucleotide sequences or polypeptide sequences having homology are referred to herein as "homologues." The term homologue includes homologous sequences from the same and other species and orthologous sequences from the same and other species. "Homology" refers to the level of similarity between two or more nucleotide sequences and/or amino acid sequences in terms of percent of positional identity (i.e., sequence similarity or identity). Homology also refers to the concept of similar functional properties among different nucleic acids, amino acids, and/or proteins.

As used herein, the phrase "nucleotide sequence homology" refers to the presence of homology between two polynucleotides. Polynucleotides have "homologous" sequences if the sequence of nucleotides in the two sequences is the same when aligned for maximum correspondence. The "percentage of sequence homology" for polynucleotides, such as 50, 55, 60, 65, 70, 75, 80, 85, 90, 95, 96, 97, 98, 99 or 100 percent sequence homology, can be determined by comparing two optimally aligned sequences over a comparison window (e.g., about 20-200 contiguous nucleotides), wherein the portion of the polynucleotide sequence in the comparison window can include additions or deletions (i.e., gaps) as compared to a reference sequence for optimal alignment of the two sequences. Optimal alignment of sequences for comparison can be conducted by computerized implementations of known algorithms, or by visual inspection. Readily available sequence comparison and multiple sequence alignment algorithms are, respectively, the Basic Local Alignment Search Tool (BLAST®; Altschul et al. (1990) *J Mol Biol* 215:403-10; Altschul et al. (1997) *Nucleic Acids Res* 25:3389-3402) and ClustalX (Chenna et al. (2003) *Nucleic Acids Res* 31:3497-3500) programs, both available on the Internet. Other suitable programs include, but are not limited to, GAP, BestFit, PlotSimilarity, and FASTA, which are part of the Accelrys GCG Package available from Accelrys Software, Inc. of San Diego, Calif., United States of America.

As used herein "sequence identity" refers to the extent to which two optimally aligned polynucleotide or polypeptide sequences are invariant throughout a window of alignment of components, e.g., nucleotides or amino acids. "Identity" can be readily calculated by known methods including, but not limited to, those described in: *Computational Molecular Biology* (Lesk, A. M., ed.) Oxford University Press, New York (1988); *Biocomputing: Informatics and Genome Projects* (Smith, D. W., ed.) Academic Press, New York (1993); *Computer Analysis of Sequence Data, Part I* (Griffin, A. M., and Griffin, H. G., eds.) Humana Press, New Jersey (1994); *Sequence Analysis in Molecular Biology* (von Heinje, G., ed.) Academic Press (1987); and *Sequence Analysis Primer* (Gribskov, M. and Devereux, J., eds.) Stockton Press, New York (1991).

As used herein, the term "substantially identical" or "corresponding to" with regard to the comparison of two (or more) nucleotide sequences means that the two nucleotide sequences have at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% sequence identity. In some embodiments, two nucleotide sequences can have at least about 75%, 80%, 85%, 90%, 95%, or 100% sequence identity, and any range or value therein. In representative embodiments, two nucleotide sequences can have at least about 95%, 96%, 97%, 98%, 99% or 100% sequence identity, and any range or value therein.

An "identity fraction" for aligned segments of a test sequence and a reference sequence is the number of identical components which are shared by the two aligned sequences divided by the total number of components in the reference sequence segment, i.e., the entire reference sequence or a smaller defined part of the reference sequence. Percent sequence identity is represented as the identity fraction multiplied by 100. As used herein, the term "percent sequence identity" or "percent identity" refers to the percentage of identical nucleotides in a linear polynucleotide sequence of a reference ("query") polynucleotide molecule (or its complementary strand) as compared to a test ("subject") polynucleotide molecule (or its complementary strand) when the two sequences are optimally aligned (with appropriate nucleotide insertions, deletions, or gaps totaling less than 20 percent of the reference sequence over the window of comparison). In some embodiments, "percent identity" can refer to the percentage of identical amino acids in an amino acid sequence.

Optimal alignment of sequences for aligning a comparison window is well known to those skilled in the art and may be conducted by tools such as the local homology algorithm of Smith and Waterman, the homology alignment algorithm of Needleman and Wunsch, the search for similarity method of Pearson and Lipman, and optionally by computerized implementations of these algorithms such as GAP, BEST-FIT, FASTA, and TFASTA available as part of the GCG® Wisconsin Package® (Accelrys Inc., Burlington, Mass.). The comparison of one or more polynucleotide sequences may be to a full-length polynucleotide sequence or a portion thereof, or to a longer polynucleotide sequence. For purposes of this invention "percent identity" may also be determined using BLAST®X version 2.0 for translated nucleotide sequences and BLAST®N version 2.0 for polynucleotide sequences.

The percent of sequence identity can be determined using the "Best Fit" or "Gap" program of the Sequence Analysis Software Package™ (Version 10; Genetics Computer Group, Inc., Madison, Wis.). "Gap" utilizes the algorithm of Needleman and Wunsch (Needleman and Wunsch, *J Mol. Biol.* 48:443-453, 1970) to find the alignment of two sequences that maximizes the number of matches and minimizes the number of gaps. "BestFit" performs an optimal alignment of the best segment of similarity between two sequences and inserts gaps to maximize the number of matches using the local homology algorithm of Smith and Waterman (Smith and Waterman, *Adv. Appl. Math.,* 2:482-489, 1981, Smith et al., *Nucleic Acids Res.* 11:2205-2220, 1983).

Useful methods for determining sequence identity are also disclosed in *Guide to Huge Computers* (Martin J. Bishop, ed., Academic Press, San Diego (1994)), and Carillo et al. (*Applied Math* 48:1073 (1988)). More particularly, preferred computer programs for determining sequence identity include but are not limited to the Basic Local Alignment Search Tool (BLAST®) programs, which are publicly available from National Center Biotechnology Information (NCBI) at the National Library of Medicine, National Institute of Health, Bethesda, Md. 20894; see BLAST® Manual, Altschul et al., NCBI, NLM, NIH; (Altschul et al., *J. Mol. Biol.* 215:403-410 (1990)); version 2.0 or higher of BLAST® programs allows the introduction of gaps (deletions and insertions) into alignments; for peptide sequence, BLAST®X can be used to determine sequence identity; and for polynucleotide sequence, BLAST®N can be used to determine sequence identity.

As used herein, the terms "phenotype," "phenotypic trait" or "trait" refer to one or more traits of an organism. The phenotype can be observable to the naked eye, or by any other means of evaluation known in the art, e.g., microscopy, biochemical analysis, and/or an electromechanical assay. In some cases, a phenotype is directly controlled by a single gene or genetic locus, i.e., a "single gene trait." In other cases, a phenotype is the result of several genes.

As used herein, the term "polymorphism" refers to a variation in the nucleotide sequence at a locus, where said variation is too common to be due merely to a spontaneous mutation. A polymorphism must have a frequency of at least about 1% in a population. A polymorphism can be a single nucleotide polymorphism (SNP), or an insertion/deletion polymorphism, also referred to herein as an "indel." Additionally, the variation can be in a transcriptional profile or a methylation pattern. The polymorphic site or sites of a nucleotide sequence can be determined by comparing the nucleotide sequences at one or more loci in two or more germplasm entries.

As used herein, the term "plant" can refer to a whole plant, a plant part or a plant organ (e.g., leaves, stems, roots, etc.), a plant tissue, a plant tissue culture, a seed, a plant cell and/or a plant germplasm. A plant cell is a cell of a plant, taken from a plant, or derived through culture from a cell taken from a plant.

As used herein, the term "plant part" includes but is not limited to embryos, pollen, seeds, leaves, flowers (including but not limited to anthers, ovules and the like), fruit, stems or branches, roots, root tips, cells including cells that are intact in plants and/or parts of plants, protoplasts, plant cell tissue cultures, plant calli, plant clumps, and the like. As used herein, "plant part" can also include germplasm. Thus, a plant part includes maize tissue culture from which soybmaizeean plants can be regenerated. Further, as used herein, "plant cell" refers to a structural and physiological unit of the plant, which comprises a cell wall and also may refer to a protoplast. A plant cell of the present invention can be in the form of an isolated single cell or can be a cultured cell or can be a part of a higher-organized unit such as, for example, a plant tissue or a plant organ.

As used herein, the term "population" refers to a genetically heterogeneous collection of plants sharing a common genetic derivation.

As used herein, the terms "progeny," "progeny plant," and/or "offspring" refer to a plant generated from a vegetative or sexual reproduction from one or more parent plants. A progeny plant may be obtained by cloning or selfing a single parent plant, or by crossing two parental plants and includes selfings as well as the F1 or F2 or still further generations. An F1 is a first-generation offspring produced from parents at least one of which is used for the first time as donor of a trait, while offspring of second generation (F2) or subsequent generations (F3, F4, and the like) are specimens produced from selfings or crossings of F1s, F2s and the like. An F1 can thus be (and in some embodiments is) a hybrid resulting from a cross between two true breeding parents (the phrase "true-breeding" refers to an individual that is homozygous for one or more traits), while an F2 can be an offspring resulting from self-pollination of the F1 hybrids.

As used herein, the term "maize" or "corn" refers to *Zea mays* plant(s).

As used herein, the term "reference sequence" refers to a defined nucleotide sequence used as a basis for nucleotide sequence comparison (e.g., Chromosome 10, Chromosome 3, Chromosome 1, Chromosome 5, and/or Chromosome 8 of *Zea mays* cultivar B73).

Genetic loci correlating with particular phenotypes, such as drought tolerance, can be mapped in an organism's genome. By identifying a marker or cluster of markers that co-segregate with a trait of interest, the breeder is able to rapidly select a desired phenotype by selecting for the proper marker (a process called marker-assisted selection, or MAS). Such markers may also be used by breeders to design genotypes in silico and to practice whole genome selection.

The present invention provides markers associated with increased yield under non-drought conditions, increased yield stability under drought conditions, and/or increased drought tolerance in maize. Detection of these markers and/or other linked markers can be used to identify, select and/or produce maize plants having increased yield under non-drought conditions, increased yield stability under drought conditions, and/or increased drought tolerance and/or to eliminate maize plants from breeding programs or from planting that do not have increased yield under non-drought conditions, increased yield stability under drought conditions, and/or increased drought tolerance.

Molecular or genetic markers are used for the visualization of differences in nucleic acid sequences. This visualization can be due to DNA-DNA hybridization techniques after digestion with a restriction enzyme (e.g., an RFLP) and/or due to techniques using the polymerase chain reaction (e.g., SNP, STS, SSR/microsatellites, AFLP, and the like). In some embodiments, all differences between two parental genotypes segregate in a mapping population based on the cross of these parental genotypes. The segregation of the different markers can be compared and recombination frequencies can be calculated. Methods for mapping markers in plants are disclosed in, for example, Glick & Thompson (1993) *Methods in Plant Molecular Biology and Biotechnology*, CRC Press, Boca Raton, Fla., United States of America; Zietkiewicz et al. (1994) Genomics 20:176-183.

Table 1 provides the names of markers (SNPs) of this invention that are associated with increased yield under non-drought conditions, increased yield stability under drought conditions, and/or increased drought tolerance in maize, the physical genetic locations of each marker on the respective maize chromosome or linkage group, and the target allele that is associated with increased yield under non-drought conditions, increased yield stability under drought conditions, and/or increased drought tolerance.

Markers of the present invention are described herein with respect to the positions of marker loci in the genome of the maize B73 variety (version 2) at the Maize Genetics and Genomics Database internet resource (browse.maizegdb.org/gb2/gbrowse/maize_v2/).

See Table 1, below.

TABLE 1

The respective maize chromosome or linkage group of physical and genetic positions of the markers of the invention including allele associated with increased yield under non-drought conditions, increased yield stability under drought conditions, and/or increased drought tolerance (fav. allele).

| Gene Model ID | Gene name | Chrom. | Gene begin | Gene end | (SNP) name | Physical position in Maize B73 | Fav. Allele/ Unfav. Allele |
|---|---|---|---|---|---|---|---|
| GRMZM2G173669 | SWEET-13a | chr10 | 14762443 | 14765098 | PZE1014822710 | 14764762 | C/T |
| GRMZM2G173669 | SWEET-13a | chr10 | 14762443 | 14765098 | PZE1014822787 | 14764839 | A/G |
| GRMZM2G173669 | SWEET-13a | chr10 | 14762443 | 14765098 | PZE1014822363 | 14764415 | G/T |
| GRMZM2G173669 | SWEET-13a | chr10 | 14762443 | 14765098 | PZE1014822960 | 14765012 | A/G |
| GRMZM2G173669 | SWEET-13a | chr10 | 14762443 | 14765098 | S_3355011 | 14764763 | G/C |
| GRMZM2G173669 | SWEET-13a | chr10 | 14762443 | 14765098 | PZE1014822606 | 14764658 | G/T |
| GRMZM2G039365 | SWEET-1a | chr3 | 171748815 | 171752467 | PZE03170079889 | 171752311 | G/A |
| GRMZM2G039365 | SWEET-1a | chr3 | 171748815 | 171752467 | PZE03170077114 | 171749536 | C/T |
| GRMZM2G039365 | SWEET-1a | chr3 | 171748815 | 171752467 | S_7767530 | 171749273 | C/T |
| GRMZM2G039365 | SWEET-1a | chr3 | 171748815 | 171752467 | S_7767535 | 171749283 | A/C |
| GRMZM2G039365 | SWEET-1a | chr3 | 171748815 | 171752467 | S_7767546 | 171749318 | A/C |
| GRMZM2G368827 | SWEET-11/MtN3 | chr1 | 194932443 | 194935353 | PZE01194799632 | 194932443 | A/T |
| GRMZM2G111926 | SWEET-16b | chr8 | 33363546 | 33368983 | PZE0833363225 | 33363625 | T/C |
| GRMZM5G872392 | SWEET-15b | chr5 | 164854921 | 164858109 | S_25177407 | 164855482 | A/C |

Thus, in some embodiments of this invention, the marker alleles associated with increased yield under non-drought conditions, increased yield stability under drought conditions, and/or increased drought tolerance in maize are as set forth in Table 1.

In some embodiments of this invention, the marker allele(s) associated with increased yield under non-drought conditions, increased yield stability under drought conditions, and/or increased drought tolerance as set forth in Table 1 can be located in a chromosomal interval including, but not limited to (a) a chromosome interval on chromosome 10 defined by and including base pair (bp) position 14762443 to base pair (bp) position 14765098 (Gene Model ID No: GRMZM2G173669); (b) a chromosome interval on chromosome 10 defined by and including base pair (bp) position 14762443 to base pair (bp) position 14765012 (PZE10148229607.S_3355639); (c) a chromosome interval on chromosome 10 defined by and including base pair (bp) position 14762443 to base pair (bp) position 14764839 (PZE1014822787.S_3355210); (d) a chromosome interval on chromosome 10 defined by and including base pair (bp) position 14762443 to base pair (bp) position 14764763 (S_3355011); (e) a chromosome interval on chromosome 10 defined by and including base pair (bp) position 14762443 to base pair (bp) position 14764762 (PZE1014822710.S_3355009); (f) a chromosome interval on chromosome 10 defined by and including base pair (bp) position 14762443 to base pair (bp) position 14764658 (PZE101482206.S_3354710); (g) a chromosome interval on chromosome 10 defined by and including base pair (bp) position 14762443 to base pair (bp) position 14764415 (PZE1014822363.S_3353987); (h) a chromosome interval on chromosome 10 defined by and including base pair (bp) position 14764415 to base pair (bp) position 14765098; (i) a chromosome interval on chromosome 10 defined by and including base pair (bp) position 14764415 to base pair (bp) position 14765012; (j) a chromosome interval on chromosome 10 defined by and including base pair (bp) position 14764415 to base pair (bp) position 14764839; (k) a chromosome interval on chromosome 10 defined by and including base pair (bp) position 14764415 to base pair (bp) position 14764763; (l) a chromosome interval on chromosome 10 defined by and including base pair (bp) position 14764415 to base pair (bp) position 14764762; (m) a chromosome interval on chromosome 10 defined by and including base pair (bp) position 14764415 to base pair (bp) position 14764658; (n) a chromosome interval on chromosome 10 defined by and including base pair (bp) position 14764658 to base pair (bp) position 14765098; (o) a chromosome interval on chromosome 10 defined by and including base pair (bp) position 14764658 to base pair (bp) position 14765012; (p) a chromosome interval on chromosome 10 defined by and including base pair (bp) position 14764658 to base pair (bp) position 14764839; (q) a chromosome interval on chromosome 10 defined by and including base pair (bp) position 14764658 to base pair (bp) position 14764763; (r) a chromosome interval on chromosome 10 defined by and including base pair (bp) position 14764658 to base pair (bp) position 14764762; (s) a chromosome interval on chromosome 10 defined by and including base pair (bp) position 14764762 to base pair (bp) position 14765098; (t) a chromosome interval on chromosome 10 defined by and including base pair (bp) position 14764762 to base pair (bp) position 14765012; (u) a chromosome interval on chromosome 10 defined by and including base pair (bp) position 14764762 to base pair (bp) position 14764839; (v) a chromosome interval on chromosome 10 defined by and including base pair (bp) position 14764762 to base pair (bp) position 14764763; (w) a chromosome interval on chromosome 10 defined by and including base pair (bp) position 14764763 to base pair (bp)

position 14765098; (x) a chromosome interval on chromosome 10 defined by and including base pair (bp) position 14764763 to base pair (bp) position 14765012; (y) a chromosome interval on chromosome 10 defined by and including base pair (bp) position 14764763 to base pair (bp) position 14764839; (z) a chromosome interval on chromosome 10 defined by and including base pair (bp) position 14764839 to base pair (bp) position 14765098; (aa) a chromosome interval on chromosome 10 defined by and including base pair (bp) position 14764839 to base pair (bp) position 14765012; (bb) a chromosome interval on chromosome 3 defined by and including base pair (bp) position 171748815 to base pair (bp) position 171752467 (Gene Model ID No: GRMZM2G039365); (cc) a chromosome interval on chromosome 3 defined by and including base pair (bp) position 171748815 to base pair (bp) position 171752311 (PZE03170079889.S_7768072); (dd) a chromosome interval on chromosome 3 defined by and including base pair (bp) position 171748815 to base pair (bp) position 171749536 (PZE03170077114.S_7767618); (ee) a chromosome interval on chromosome 3 defined by and including base pair (bp) position 171748815 to base pair (bp) position 171749318 (S_7767546); (ff) a chromosome interval on chromosome 3 defined by and including base pair (bp) position 171748815 to base pair (bp) position 171749283 (S_7767535); (gg) a chromosome interval on chromosome 3 defined by and including base pair (bp) position 171748815 to base pair (bp) position 171749273 (S_7767530); (hh) a chromosome interval on chromosome 3 defined by and including base pair (bp) position 171749273 to base pair (bp) position 171752467; (ii) a chromosome interval on chromosome 3 defined by and including base pair (bp) position 171749273 to base pair (bp) position 171752311; (jj) a chromosome interval on chromosome 3 defined by and including base pair (bp) position 171749273 to base pair (bp) position 171749536; (kk) a chromosome interval on chromosome 3 defined by and including base pair (bp) position 171749273 to base pair (bp) position 171749318; (ll) a chromosome interval on chromosome 3 defined by and including base pair (bp) position 171749273 to base pair (bp) position 171749283; (mm) a chromosome interval on chromosome 3 defined by and including base pair (bp) position 171749283 to base pair (bp) position 171752467; (nn) a chromosome interval on chromosome 3 defined by and including base pair (bp) position 171749283 to base pair (bp) position 171752311; (oo) a chromosome interval on chromosome 3 defined by and including base pair (bp) position 171749283 to base pair (bp) position 171749536; (pp) a chromosome interval on chromosome 3 defined by and including base pair (bp) position 171749283 to base pair (bp) position 171749318; (qq) a chromosome interval on chromosome 3 defined by and including base pair (bp) position 171749318 to base pair (bp) position 171752467; (rr) a chromosome interval on chromosome 3 defined by and including base pair (bp) position 171749318 to base pair (bp) position 171752311; (ss) a chromosome interval on chromosome 3 defined by and including base pair (bp) position 171749318 to base pair (bp) position 171749536; (tt) a chromosome interval on chromosome 3 defined by and including base pair (bp) position 171749536 to base pair (bp) position 171752467; (uu) a chromosome interval on chromosome 3 defined by and including base pair (bp) position 171749536 to base pair (bp) position 171752311; (vv) a chromosome interval on chromosome 1 defined by and including base pair (bp) position 194932443 (PZE01194799632) to base pair (bp) position 194935353 (Gene Model ID No: GRMZM2G368827); (ww) a chromosome interval on chromosome 8 defined by and including base pair (bp) position 33363546 to base pair (bp) position 33368983 (Gene Model ID No: GRMZM2G111926); (xx) a chromosome interval on chromosome 8 defined by and including base pair (bp) position 33363546 to base pair (bp) position 33363625 (PZE0833363225.S_16494088); (yy) a chromosome interval on chromosome 8 defined by and including base pair (bp) position 33363625 to base pair (bp) position 33368983; (zz) a chromosome interval on chromosome 5 defined by and including base pair (bp) position 164854921 to base pair (bp) position 164858109 (Gene Model ID No: GRMZM2G872392); (aaa) a chromosome interval on chromosome 5 defined by and including base pair (bp) position 164854921 to base pair (bp) position 164855482 (S_25177407); (bbb) a chromosome interval on chromosome 5 defined by and including base pair (bp) position 164855482 to base pair (bp) position 164858109; and (ccc) any combination of (a) to (bbb) above.

In some embodiments, bp position 14762443 comprises a G allele; bp position 14765098 comprises a C allele; bp position 14765012 comprises an A allele; bp position 14764839 comprises an A allele; bp position 14764763 comprises a G allele; bp position 14764762 comprises a C allele; bp position 14764658 comprises a G allele; bp position 14764415 comprises a G allele; bp position 171748815 comprises a G allele; bp position 171752467 comprises a C allele; bp position 171752311 comprises a G allele; bp position 171749536 comprises a C allele; bp position 171749318 comprises an A allele; bp position 171749283 comprises an A allele; bp position 171749273 comprises a C allele; bp position 194932443 comprises an A allele; bp position 194935353 comprises a T allele; bp position 33363546 comprises a C allele; bp position 33368983 comprises an A allele; bp position 33363625 comprises a T allele; bp position 164854921 comprises a C allele; bp position 164858109 comprises a G allele; and bp position 164855482 comprises an A allele.

Thus, in some embodiments, the marker allele(s) associated with increased yield under non-drought conditions, increased yield stability under drought conditions, and/or increased drought tolerance as set forth in Table 1 can be located in a chromosomal interval defined by and including (a) a G allele at base pair (bp) position 14762443 and a C allele at base pair (bp) position 14765098; (b) a G allele at base pair (bp) position 14762443 and an A allele at base pair (bp) position 14765012; (c) a G allele at base pair (bp) position 14762443 and an A allele at base pair (bp) position 14764839; (d) a G allele at base pair (bp) position 14762443 and a G allele at base pair (bp) position 14764763; (e) a G allele at base pair (bp) position 14762443 and a C allele at base pair (bp) position 14764762; (f) a G allele at base pair (bp) position 14762443 and a G allele at base pair (bp) position 14764658; (g) a G allele at base pair (bp) position 14762443 and a G allele at base pair (bp) position 14764415; (h) a G allele at base pair (bp) position 14764415 and a C allele at base pair (bp) position 14765098; (i) a G allele at base pair (bp) position 14764415 and an A allele at base pair (bp) position 14765012; (j) a G allele at base pair (bp) position 14764415 and an A allele at base pair (bp) position 14764839; (k) a G allele at base pair (bp) position 14764415 and a G allele at base pair (bp) position 14764763; (l) a G allele at base pair (bp) position 14764415 and a C allele at base pair (bp) position 14764762; (m) a G allele at base pair (bp) position 14764415 and a G allele at base pair (bp) position 14764658; (n) a G allele at base pair (bp) position 14764658 and a C allele at base pair (bp) position 14765098; (o) a G allele at base pair (bp) position 14764658 and an A allele at base pair (bp) position 14765012; (p) a G allele at base pair (bp) position 14764658 and an A allele at base pair (bp) position 14764839; (q) a G allele at base pair (bp) position 14764658 and a G allele at base pair (bp) position 14764763; (r) a G allele at base pair (bp) position 14764658 and a C allele at base pair (bp) position 14764762; (s) a C allele at base pair (bp) position 14764762 and a C allele at base pair (bp) position 14765098; (t) a C allele at base pair (bp) position 14764762 and an A allele at base pair (bp) position 14765012; (u) a C allele at base pair (bp) position 14764762 and an A allele at base pair (bp) position 14764839; (v) a C allele at base pair (bp) position 14764762 and a G allele at base pair (bp) position 14764763; (w) a G allele at base pair (bp) position 14764763 and a C allele at base pair (bp) position 14765098; (x) a G allele at base pair (bp) position 14764763 and an A allele at base pair (bp) position 14765012; (y) a G allele at base pair (bp) position 14764763 and an A allele at base pair (bp) position 14764839; (z) an A allele at base pair (bp) position 14764839 and a C allele at base pair (bp) position 14765098; (aa) an A allele at base pair (bp) position 14764839 and an A allele at base pair (bp) position 14765012; (bb) a G allele at base pair (bp) position 171748815 and a C allele at base pair (bp) position 171752467; (cc) a G allele at base pair (bp) position 171748815 and a G allele at base pair (bp) position 171752311; (dd) a G allele at base pair (bp) position 171748815 and a C allele at base pair (bp) position 171749536; (ee) a G allele at base pair (bp) position 171748815 and an A allele at base pair (bp) position 171749318; (ff) a G allele at base pair (bp) position 171748815 and an A allele at base pair (bp) position 171749283; (gg) a G allele at base pair (bp) position 171748815 and a C allele at base pair (bp) position 171749273; (hh) a C allele at base pair (bp) position 171749273 and a C allele at base pair (bp) position 171752467; (ii) a C allele at base pair (bp) position 171749273 and a G allele at base pair (bp) position 171752311; (jj) a C allele at base pair (bp) position 171749273 and a C allele at base pair (bp) position 171749536; (kk) a C allele at base pair (bp) position 171749273 and an A allele at base pair (bp) position 171749318; (ll) a C allele at base pair (bp) position 171749273 and an A allele at base pair (bp) position 171749283; (mm) an A allele at base pair (bp) position 171749283 and a C allele at base pair (bp) position 171752467; (nn) an A allele at base pair (bp) position 171749283 a G allele at base pair (bp) position 171752311; (oo) an A allele at base pair (bp) position 171749283 and a C allele at base pair (bp) position 171749536; (pp) an A allele at base pair (bp) position 171749283 and an A allele at base pair (bp) position 171749318; (qq) an A allele at base pair (bp) position 171749318 and a C allele at base pair (bp) position 171752467; (rr) an A allele at base pair (bp) position 171749318 and a G allele at base pair (bp) position 171752311; (ss) an A allele at base pair (bp) position 171749318 and a C allele at base pair (bp) position 171749536; (tt) a C allele at base pair (bp) position 171749536 and a C allele at base pair (bp) position 171752467; (uu) a C allele at base pair (bp) position 171749536 and a G allele at base pair (bp) position 171752311; (vv) an A allele at base pair (bp) position 194932443 and a T allele at base pair (bp) position 194935353; (ww) a C allele at base pair (bp) position 33363546 and an A allele at base pair (bp) position 33368983; (xx) a C allele at base pair (bp) position 33363546 and a T allele at base pair (bp) position 33363625; (yy) a T allele at base pair (bp) position 33363625 and an A allele at base pair (bp) position 33368983; (zz) a C allele at base pair (bp) position 164854921 and a G allele at base pair (bp) position 164858109; (aaa) a C allele at base pair (bp) position 164854921 and an A allele at base pair (bp) position 164855482; (bbb) an A allele at base pair (bp) position 164855482 and a G allele at base pair (bp) position 164858109; and (ccc) any combination of (a) to (bbb) above. In some embodiments, the allele at each base pair position can be homozygous.

Thus, for example, in some embodiments, the marker allele(s) associated with increased yield under non-drought conditions, increased yield stability under drought conditions, and/or increased drought tolerance as set forth in Table 1 can be located in a chromosomal interval defined by and including (a) a GG allele at base pair (bp) position 14764415 and an AA allele at base pair (bp) position 14765012; (b) a GG allele at base pair (bp) position 14764415 and an AA allele at base pair (bp) position 14764839; (c) a GG allele at base pair (bp) position 14764415 and a GG allele at base pair (bp) position 14764763; (d) a GG allele at base pair (bp) position 14764415 and a CC allele at base pair (bp) position 14764762; (e) a GG allele at base pair (bp) position 14764415 and a GG allele at base pair (bp) position 14764658; (f) a GG allele at base pair (bp) position 14764658 and an AA allele at base pair (bp) position 14765012; (g) a GG allele at base pair (bp) position 14764658 and an AA allele at base pair (bp) position 14764839; (h) a GG allele at base pair (bp) position 14764658 and a GG allele at base pair (bp) position 14764763; (i) a GG allele at base pair (bp) position 14764658 and a CC allele at base pair (bp) position 14764762; (j) a CC allele at base pair (bp) position 14764762 and an AA allele at base pair (bp) position 14765012; (k) a CC allele at base pair (bp) position 14764762 and an AA allele at base pair (bp) position 14764839; (l) a CC allele at base pair (bp) position 14764762 and a GG allele at base pair (bp) position 14764763; (m) a GG allele at base pair (bp) position 14764763 and an AA allele at base pair (bp) position 14765012; (n) a GG allele at base pair (bp) position 14764763 and an AA allele at base pair (bp) position 14764839; (o) an AA allele at base pair (bp) position 14764839 and an AA allele at base pair (bp) position 14765012; (p) a CC allele at base pair (bp) position 171749273 and a GG allele at base pair (bp) position 171752311; (q) a CC allele at base pair (bp) position 171749273 and a CC allele at base pair (bp) position 171749536; (r) a CC allele at base pair (bp) position 171749273 and an AA allele at base pair (bp) position 171749318; (s) a CC allele at base pair (bp) position 171749273 and an AA allele at base pair (bp) position 171749283; (t) an AA allele at base pair (bp) position 171749283 a GG allele at base pair (bp) position 171752311; (u) an AA allele at base pair (bp) position 171749283 and a CC allele at base pair (bp) position 171749536; (v) an AA allele at base pair (bp) position 171749283 and an AA allele at base pair (bp) position 171749318; (w) an AA allele at base pair (bp) position 171749318 and a GG allele at base pair (bp) position 171752311; (x) an AA allele at base pair (bp) position 171749318 and a CC allele at base pair (bp) position 171749536; and/or (y) a CC allele at base pair (bp) position 171749536 and a GG allele at base pair position 171752311.

As would be understood by one of skill in the art, additional chromosomal intervals can be defined by the SNP markers provided herein in Table 1.

In some embodiments, a genetic marker of this invention as set forth in Table 1 is associated with increased yield under non-drought conditions, increased yield stability under drought conditions, and/or increased drought tolerance in maize, wherein the genetic marker includes but is not limited to: a G allele at base pair (bp) position 14762443; a C allele at base pair (bp) position 14765098; an A allele at base pair (bp) position 14765012; an A allele at base pair (bp) position 14764839; a G allele at base pair (bp) position 14764763; a C allele at base pair (bp) position 14764762; a G allele at base pair (bp) position 14764658; a G allele at base pair (bp) position 14764415; a G allele at base pair (bp) position 171748815; a C allele at base pair (bp) position 171752467; a G allele at base pair (bp) position 171752311; a C allele at base pair (bp) position 171749536; an A allele at base pair (bp) position 171749318; an A allele at base pair (bp) position 171749283; a C allele at base pair (bp) position 171749273; an A allele at base pair (bp) position 194932443; a T allele at base pair (bp) position 194935353; a C allele at base pair (bp) position 33363546; an A allele at base pair (bp) position 33368983; a T allele at base pair (bp) position 33363625; a C allele at base pair (bp) position 164854921; a G allele at base pair (bp) position 164858109; an A allele at base pair (bp) position 164855482; and/or any combination thereof. In some embodiments, the allele at each described base pair position can be independently homozygous or heterozygous. In some embodiments, the allele at each described base pair position can be homozygous.

In some embodiments, a combination of genetic markers of this invention as set forth in Table 1 is associated with increased yield under non-drought conditions, increased yield stability under drought conditions, and/or increased drought tolerance in maize, wherein the combination of genetic markers includes but is not limited to: (a) a G allele at base pair (bp) position 14762443 and a C allele at base pair (bp) position 14765098; (b) a G allele at base pair (bp) position 14762443 and an A allele at base pair (bp) position 14765012; (c) a G allele at base pair (bp) position 14762443 and an A allele at base pair (bp) position 14764839; (d) a G allele at base pair (bp) position 14762443 and a G allele at base pair (bp) position 14764763; (e) a G allele at base pair (bp) position 14762443 and a C allele at base pair (bp) position 14764762; (f) a G allele at base pair (bp) position 14762443 and a G allele at base pair (bp) position 14764658; (g) a G allele at base pair (bp) position 14762443 and a G allele at base pair (bp) position 14764415; (h) a G allele at base pair (bp) position 14764415 and a C allele at base pair (bp) position 14765098; (i) a G allele at base pair (bp) position 14764415 and an A allele at base pair (bp) position 14765012; (j) a G allele at base pair (bp) position 14764415 and an A allele at base pair (bp) position 14764839; (k) a G allele at base pair (bp) position 14764415 and a G allele at base pair (bp) position 14764763; (l) a G allele at base pair (bp) position 14764415 and a C allele at base pair (bp) position 14764762; (m) a G allele at base pair (bp) position 14764415 and a G allele at base pair (bp) position 14764658; (n) a G allele at base pair (bp) position 14764658 and a C allele at base pair (bp) position 14765098; (o) a G allele at base pair (bp) position 14764658 and an A allele at base pair (bp) position 14765012; (p) a G allele at base pair (bp) position 14764658 and an A allele at base pair (bp) position 14764839; (q) a G allele at base pair (bp) position 14764658 and a G allele at base pair (bp) position 14764763; (r) a G allele at base pair (bp) position 14764658 and a C allele at base pair (bp) position 14764762; (s) a C allele at base pair (bp) position 14764762 and a C allele at base pair (bp) position 14765098; (t) a C allele at base pair (bp) position 14764762 and an A allele at base pair (bp) position 14765012; (u) a C allele at base pair (bp) position 14764762 and an A allele at base pair (bp) position 14764839; (v) a C allele at base pair (bp) position 14764762 and a G allele at base pair (bp) position 14764763; (w) a G allele at base pair (bp) position 14764763 and a C allele at base pair (bp) position 14765098; (x) a G allele at base pair (bp) position 14764763 and an A allele at base pair (bp) position 14765012; (y) a G allele at base pair (bp) position 14764763 and an A allele at base pair (bp) position 14764839; (z) an A allele at base pair (bp) position 14764839 and a C allele at base pair (bp) position 14765098; (aa) an A allele at base pair (bp) position 14764839 and an A allele at base pair (bp) position 14765012; (bb) a G allele at base pair (bp) position 171748815 and a C allele at base pair (bp) position 171752467 (Gene Model ID No: GRMZM2G039365); (cc) a G allele at base pair (bp) position 171748815 and a G allele at base pair (bp) position 171752311; (dd) a G allele at base pair (bp) position 171748815 and a C allele at base pair (bp) position 171749536; (ee) a G allele at base pair (bp) position 171748815 and an A allele at base pair (bp) position 171749318; (ff) a G allele at base pair (bp) position 171748815 and an A allele at base pair (bp) position 171749283; (gg) a G allele at base pair (bp) position 171748815 and a C allele at base pair (bp) position 171749273; (hh) a C allele at base pair (bp) position 171749273 and a C allele at base pair (bp) position 171752467; (ii) a C allele at base pair (bp) position 171749273 and a G allele at base pair (bp) position 171752311; (jj) a C allele at base pair (bp) position 171749273 and a C allele at base pair (bp) position 171749536; (kk) a C allele at base pair (bp) position 171749273 and an A allele at base pair (bp) position 171749318; (ll) a C allele at base pair (bp) position 171749273 and an A allele at base pair (bp) position 171749283; (mm) an A allele at base pair (bp) position 171749283 and a C allele at base pair (bp) position 171752467; (nn) an A allele at base pair (bp) position 171749283 a G allele at base pair (bp) position 171752311; (oo) an A allele at base pair (bp) position 171749283 and a C allele at base pair (bp) position 171749536; (pp) an A allele at base pair (bp) position 171749283 and an A allele at base pair (bp) position 171749318; (qq) an A allele at base pair (bp) position 171749318 and a C allele at base pair (bp) position 171752467; (rr) an A allele at base pair (bp) position 171749318 and a G allele at base pair (bp) position 171752311; (ss) an A allele at base pair (bp) position 171749318 and a C allele at base pair (bp) position 171749536; (tt) a C allele at base pair (bp) position 171749536 and a C allele at base pair (bp) position 171752467; (uu) a C allele at base pair (bp) position 171749536 and a G allele at base pair (bp) position 171752311; (vv) an A allele at base pair (bp) position 194932443 and a T allele at base pair (bp) position 194935353 (Gene Model ID No: GRMZM2G368827); (ww) a C allele at base pair (bp) position 33363546 and an A allele at base pair (bp) position 33368983 (Gene Model ID No: GRMZM2G111926); (xx) a C allele at base pair (bp) position 33363546 and a T allele at base pair (bp) position 33363625; (yy) a T allele at base pair (bp) position 33363625 and an A allele at base pair (bp) position 33368983; (zz) a C allele at base pair (bp) position 164854921 and a G allele at base pair (bp) position 164858109 (Gene Model ID No: GRMZM2G872392); (aaa) a C allele at base pair (bp) position 164854921 and an A allele at base pair (bp) position 164855482; (bbb) an A allele at base pair (bp) position 164855482 and a G allele at base pair (bp) position 164858109; and (ccc) any combination of (a) to (bbb) above. In some embodiments, the allele at each described base pair position can be independently homozygous or heterozygous. In some embodiments, the allele at each described base pair position can be homozygous.

In some embodiments, the combination of markers associated with increased yield under non-drought conditions, increased yield stability under drought conditions, and/or increased drought tolerance in maize, can be any combination of markers identified on chromosome 3, markers identified on chromosome 10, markers identified on chromosome 1, markers identified on chromosome 8, or markers identified on chromosome 5. Thus, in some embodiments, a combination of markers associated with increased yield under non-drought conditions, increased yield stability under drought conditions, and/or increased drought tolerance in maize can include, but are not limited to, all or any combination of a G allele at base pair (bp) position 14762443; a C allele at base pair (bp) position 14765098; an A allele at base pair (bp) position 14765012; an A allele at base pair (bp) position 14764839; a G allele at base pair (bp) position 14764763; a C allele at base pair (bp) position 14764762; a G allele at base pair (bp) position 14764658; and/or a G allele at base pair (bp) position 14764415 each of which are located on maize chromosome 10. In some embodiments, the combination of markers associated with increased yield under non-drought conditions, increased yield stability under drought conditions, and/or increased drought tolerance in maize can include, but are not limited to, all or any combination of a G allele at base pair (bp) position 171748815; a C allele at base pair (bp) position 171752467; a G allele at base pair (bp) position 171752311; a C allele at base pair (bp) position 171749536; an A allele at base pair (bp) position 171749318; an A allele at base pair (bp) position 171749283; and/or a C allele at base pair (bp) position 171749273 each of which are located on maize chromosome 3. In some embodiments, the combination of markers associated with increased yield under non-drought conditions, increased yield stability under drought conditions, and/or increased drought tolerance in maize can include, but are not limited to, an A allele at base pair (bp) position 194932443 and/or a T allele at base pair (bp) position 194935353, which are located on maize chromosome 1. In some embodiments, the combination of markers associated with increased yield under non-drought conditions, increased yield stability under drought conditions, and/or increased drought tolerance in maize can include, but are not limited to, all or any combination of a C allele at base pair (bp) position 33363546; an A allele at base pair (bp) position 33368983; and/or a T allele at base pair (bp) position 33363625 each of which are located on maize chromosome 8. In some embodiments, the combination of markers associated with increased yield under non-drought conditions, increased yield stability under drought conditions, and/or increased drought tolerance in maize can include, but are not limited to, all or any combination of a C allele at base pair (bp) position 164854921; a G allele at base pair (bp) position 164858109; and/or an A allele at base pair (bp) position 164855482 each of which are located on maize chromosome 5. In some embodiments, the allele at each described base pair position can be independently homozygous or heterozygous. In some embodiments, the allele at each described base pair position can be homozygous.

Accordingly, this invention further provides methods of identifying, selecting, and/or producing a maize plant or part thereof having increased yield under non-drought conditions, increased yield stability under drought conditions, and/or increased drought tolerance, said method comprising: detecting, in said maize plant or maize plant part, the presence of at least one genetic marker associated with increased yield under non-drought conditions, increased yield stability under drought conditions, and/or increased drought tolerance in a maize plant, as described herein. In further embodiments, said at least one marker can comprise, consist essentially of or consist of any marker linked to the aforementioned genetic markers. That is, any genetic marker that is in linkage disequilibrium with any of the aforementioned markers (SNPs, chromosome intervals and/or combinations of markers (haplotypes)) may also be used to identify, select and/or produce a maize plant having increased yield under non-drought conditions, increased yield stability under drought conditions, and/or increased drought tolerance. Linked markers may be determined, for example, by using resources available on the MaizeGDB website (maizegdb.org), Maize Sequence (ensembl.gramene.org), Phytozome v9.1: *Zea mays* (phytozome.net/maize.php).

The present invention further provides that the detecting of a genetic marker can comprise the use of a nucleic acid probe having a nucleotide base sequence that is substantially complementary (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% complementary) to a nucleic acid sequence defining the molecular marker and which nucleic acid probe specifically hybridizes under stringent conditions with a nucleic acid sequence defining the molecular marker. A suitable nucleic acid probe can for instance be a single strand of the amplification product corresponding to the marker. In some embodiments, the detecting of a marker is designed to determine whether a particular allele of a SNP is present or absent in a particular plant.

Additionally, the methods of this invention include detecting an amplified DNA fragment associated with the presence of a particular allele of a SNP. In some embodiments, the amplified fragment associated with a particular allele of a SNP has a predicted length or nucleic acid sequence, and detecting an amplified DNA fragment having the predicted length or the predicted nucleic acid sequence is performed such that the amplified DNA fragment has a length that corresponds (plus or minus a few bases; e.g., a length of one, two or three bases more or less) to the expected length based on a similar reaction with the same primers with the DNA from the plant in which the marker was first detected or the nucleic acid sequence that corresponds (e.g., a homology of at least about 80%, 81%, 82%, 83%, 84%, 85%, 86%, 87%, 88%, 89%, 90%, 91%, 92%, 93%, 94%, 95%, 96%, 97%, 98%, 99% or more) to the expected sequence based on the sequence of the marker associated with that SNP in the plant in which the marker was first detected.

The detecting of an amplified DNA fragment having the predicted length or the predicted nucleic acid sequence can be performed by any of a number or techniques, including, but not limited to, standard gel-electrophoresis techniques or by using automated DNA sequencers. Such methods of detecting an amplified DNA fragment are not described here in detail as they are well known to those of ordinary skill in the art.

As shown in Table 1, the SNP markers of this invention are associated with increased yield under non-drought conditions, increased yield stability under drought conditions, and/or increased drought tolerance. In some embodiments, as described herein, one marker or a combination of markers can be used to detect the presence of a maize plant having increased yield under non-drought conditions, increased yield stability under drought conditions, and/or increased drought tolerance. In some embodiments, a marker can be located within a chromosomal interval (QTL) or be present in the genome of the plant as a haplotype as defined herein.

Thus, methods for identifying and/or selecting a maize plant or germplasm having increased yield under non-drought conditions, increased yield stability under drought conditions, and/or increased drought tolerance comprise detecting the presence of a genetic marker (e.g., SNP, SNP located in chromosomal interval (QTL) and/or combination of SNPs) associated with increased yield under non-drought conditions, increased yield stability under drought conditions, and/or increased drought tolerance in a maize plant or part thereof. The genetic marker can be detected in any sample taken from, for example, a maize plant or from a maize germplasm, including, but not limited to, the whole plant or germplasm or any part thereof (e.g., a seed, a leaf, a tissue culture, a cell, etc.).

Accordingly, in some aspects of the present invention, a method of identifying and/or selecting a maize plant or maize plant part having increased yield under non-drought conditions, increased yield stability under drought conditions, and/or increased drought tolerance is provided, the method comprising: detecting, in said maize plant or maize plant part, the presence of a marker associated with increased yield under non-drought conditions, increased yield stability under drought conditions, and/or increased drought tolerance in a maize plant, wherein said marker is located within a chromosomal interval comprising, consisting essentially of, or consisting of (a) a chromosome interval on chromosome 10 defined by and including base pair (bp) position 14762443 to base pair (bp) position 14765098; (b) a chromosome interval on chromosome 10 defined by and including base pair (bp) position 14762443 to base pair (bp) position 14765012; (c) a chromosome interval on chromosome 10 defined by and including base pair (bp) position 14762443 to base pair (bp) position 14764839; (d) a chromosome interval on chromosome 10 defined by and including base pair (bp) position 14762443 to base pair (bp) position 14764763; (e) a chromosome interval on chromosome 10 defined by and including base pair (bp) position 14762443 to base pair (bp) position 14764762; (f) a chromosome interval on chromosome 10 defined by and including base pair (bp) position 14762443 to base pair (bp) position 14764658; (g) a chromosome interval on chromosome 10 defined by and including base pair (bp) position 14762443 to base pair (bp) position 14764415; (h) a chromosome interval on chromosome 10 defined by and including base pair (bp) position 14764415 to base pair (bp) position 14765098; (i) a chromosome interval on chromosome 10 defined by and including base pair (bp) position 14764415 to base pair (bp) position 14765012; (j) a chromosome interval on chromosome 10 defined by and including base pair (bp) position 14764415 to base pair (bp) position 14764839; (k) a chromosome interval on chromosome 10 defined by and including base pair (bp) position 14764415 to base pair (bp) position 14764763; (l) a chromosome interval on chromosome 10 defined by and including base pair (bp) position 14764415 to base pair (bp) position 14764762; (m) a chromosome interval on chromosome 10 defined by and including base pair (bp) position 14764415 to base pair (bp) position 14764658; (n) a chromosome interval on chromosome 10 defined by and including base pair (bp) position 14764658 to base pair (bp) position 14765098; (o) a chromosome interval on chromosome 10 defined by and including base pair (bp) position 14764658 to base pair (bp) position 14765012; (p) a chromosome interval on chromosome 10 defined by and including base pair (bp) position 14764658 to base pair (bp) position 14764839; (q) a chromosome interval on chromosome 10 defined by and including base pair (bp) position 14764658 to base pair (bp) position 14764763; (r) a chromosome interval on chromosome 10 defined by and including base pair (bp) position 14764658 to base pair (bp) position 14764762; (s) a chromosome interval on chromosome 10 defined by and including base pair (bp) position 14764762 to base pair (bp) position 14765098; (t) a chromosome interval on chromosome 10 defined by and including base pair (bp) position 14764762 to base pair (bp) position 14765012; (u) a chromosome interval on chromosome 10 defined by and including base pair (bp) position 14764762 to base pair (bp) position 14764839; (v) a chromosome interval on chromosome 10 defined by and including base pair (bp) position 14764762 to base pair (bp) position 14764763; (w) a chromosome interval on chromosome 10 defined by and including base pair (bp) position 14764763 to base pair (bp) position 14765098; (x) a chromosome interval on chromosome 10 defined by and including base pair (bp) position 14764763 to base pair (bp) position 14765012; (y) a chromosome interval on chromosome 10 defined by and including base pair (bp) position 14764763 to base pair (bp) position 14764839; (z) a chromosome interval on chromosome 10 defined by and including base pair (bp) position 14764839 to base pair (bp) position 14765098; (aa) a chromosome interval on chromosome 10 defined by and including base pair (bp) position 14764839 to base pair (bp) position 14765012; (bb) a chromosome interval on chromosome 3 defined by and including base pair (bp) position 171748815 to base pair (bp) position 171752467; (cc) a chromosome interval on chromosome 3 defined by and including base pair (bp) position 171748815 to base pair (bp) position 171752311; (dd) a chromosome interval on chromosome 3 defined by and including base pair (bp) position 171748815 to base pair (bp) position 171749536; (ee) a chromosome interval on chromosome 3 defined by and including base pair (bp) position 171748815 to base pair (bp) position 171749318; (ff) a chromosome interval on chromosome 3 defined by and including base pair (bp) position 171748815 to base pair (bp) position 171749283; (gg) a chromosome interval on chromosome 3 defined by and including base pair (bp) position 171748815 to base pair (bp) position 171749273; (hh) a chromosome interval on chromosome 3 defined by and including base pair (bp) position 171749273 to base pair (bp) position 171752467; (ii) a chromosome interval on chromosome 3 defined by and including base pair (bp) position 171749273 to base pair (bp) position 171752311; (jj) a chromosome interval on chromosome 3 defined by and including base pair (bp) position 171749273 to base pair (bp) position 171749536; (kk) a chromosome interval on chromosome 3 defined by and including base pair (bp) position 171749273 to base pair (bp) position 171749318; (ll) a chromosome interval on chromosome 3 defined by and including base pair (bp) position 171749273 to base pair (bp) position 171749283; (mm) a chromosome interval on chromosome 3 defined by and including base pair (bp) position 171749283 to base pair (bp) position 171752467; (nn) a chromosome interval on chromosome 3 defined by and including base pair (bp) position 171749283 to base pair (bp) position 171752311; (oo) a chromosome interval on chromosome 3 defined by and including base pair (bp)

position 171749283 to base pair (bp) position 171749536; (pp) a chromosome interval on chromosome 3 defined by and including base pair (bp) position 171749283 to base pair (bp) position 171749318; (qq) a chromosome interval on chromosome 3 defined by and including base pair (bp) position 171749318 to base pair (bp) position 171752467; (rr) a chromosome interval on chromosome 3 defined by and including base pair (bp) position 171749318 to base pair (bp) position 171752311; (ss) a chromosome interval on chromosome 3 defined by and including base pair (bp) position 171749318 to base pair (bp) position 171749536; (tt) a chromosome interval on chromosome 3 defined by and including base pair (bp) position 171749536 to base pair (bp) position 171752467; (uu) a chromosome interval on chromosome 3 defined by and including base pair (bp) position 171749536 to base pair (bp) position 171752311; (vv) a chromosome interval on chromosome 1 defined by and including base pair (bp) position 194932443 to base pair (bp) position 194935353; (ww) a chromosome interval on chromosome 8 defined by and including base pair (bp) position 33363546 to base pair (bp) position 33368983; (xx) a chromosome interval on chromosome 8 defined by and including base pair (bp) position 33363546 to base pair (bp) position 33363625; (yy) a chromosome interval on chromosome 8 defined by and including base pair (bp) position 33363625 to base pair (bp) position 33368983; (zz) a chromosome interval on chromosome 5 defined by and including base pair (bp) position 164854921 to base pair (bp) position 164858109; (aaa) a chromosome interval on chromosome 5 defined by and including base pair (bp) position 164854921 to base pair (bp) position 164855482; (bbb) a chromosome interval on chromosome 5 defined by and including base pair (bp) position 164855482 to base pair (bp) position 164858109; and (ccc) any combination of (a) to (bbb) above, thereby identifying and/or selecting a maize plant or maize plant part having increased yield under non-drought conditions, increased yield stability under drought conditions, and/or increased drought tolerance as compared to a control maize plant.

In some embodiments, an allele is detected at the base pair positions of the chromosome intervals described herein, wherein said allele comprises, consists essentially of, or consists of a G or GG at base pair (bp) position 14762443; a C or CC at base pair (bp) position 14765098; an A or AA at base pair (bp) position 14765012; an A or AA at base pair (bp) position 14764839; a G or GG at base pair (bp) position 14764763; a C or CC at base pair (bp) position 14764762; a G or GG at base pair (bp) position 14764658; a G or GG at base pair (bp) position 14764415; a G at base pair (bp) position 171748815; a C at base pair (bp) position 171752467; a G or GG at base pair (bp) position 171752311; a C or CC at base pair (bp) position 171749536; an A or AA at base pair (bp) position 171749318; an A or AA at base pair (bp) position 171749283; a C or CC at base pair (bp) position 171749273; an A or AA at base pair (bp) position 194932443; a T or TT at base pair (bp) position 194935353; a C or CC at base pair (bp) position 33363546; an A or AA at base pair (bp) position 33368983; a T or TT at base pair (bp) position 33363625; a C or CC at base pair (bp) position 164854921; a G or GG at base pair (bp) position 164858109; and/or an A or AA at base pair (bp) position 164855482. In some embodiments, the alleles defining the chromosome intervals can be independently heterozygous or homozygous.

In some embodiments, a method of identifying and/or selecting a maize plant or maize plant part having increased yield under non-drought conditions, increased yield stability under drought conditions, and/or increased drought tolerance is provided, the method comprising: detecting, in a maize plant or maize plant part, the presence of a marker associated with increased yield under non-drought conditions, increased yield stability under drought conditions, and/or increased drought tolerance in a maize plant, wherein said marker is located within a chromosomal interval comprising, consisting essentially of, or consisting of: a chromosomal interval on chromosome 10 defined by and including a G or GG allele at base pair (bp) position 14762443 and a C or CC allele at base pair (bp) position 14765098; a G or GG allele at base pair (bp) position 14762443 and an A or AA allele at base pair (bp) position 14765012; a G or GG allele at base pair (bp) position 14762443 and an A or AA allele at base pair (bp) position 14764839; a G or GG allele at base pair (bp) position 14762443 and a G or GG allele at base pair (bp) position 14764763; a G or GG allele at base pair (bp) position 14762443 and a C or CC allele at base pair (bp) position 14764762; a G or GG allele at base pair (bp) position 14762443 and a G or GG allele at base pair (bp) position 14764658; a G or GG allele at base pair (bp) position 14762443 and a G or GG allele at base pair (bp) position 14764415; a G or GG allele at base pair (bp) position 14764415 and a C or CC allele at base pair (bp) position 14765098; a G or GG allele at base pair (bp) position 14764415 and an A or AA allele at base pair (bp) position 14765012; a G or GG allele at base pair (bp) position 14764415 and an A allele at base pair (bp) position 14764839; a G or GG allele at base pair (bp) position 14764415 and a G allele at base pair (bp) position 14764763; a G or GG allele at base pair (bp) position 14764415 and a C or CC allele at base pair (bp) position 14764762; a G or GG allele at base pair (bp) position 14764415 and a G or GG allele at base pair (bp) position 14764658; a G or GG allele at base pair (bp) position 14764658 and a C allele at base pair (bp) position 14765098; a G or GG allele at base pair (bp) position 14764658 and an A or AA allele at base pair (bp) position 14765012; a G or GG allele at base pair (bp) position 14764658 and an A or AA allele at base pair (bp) position 14764839; a G or GG allele at base pair (bp) position 14764658 and a G or GG allele at base pair (bp) position 14764763; a G or GG allele at base pair (bp) position 14764658 and a C or CC allele at base pair (bp) position 14764762; a C or CC allele at base pair (bp) position 14764762 and a C or CC allele at base pair (bp) position 14765098; a C or CC allele at base pair (bp) position 14764762 and an A or AA allele at base pair (bp) position 14765012; a C or CC allele at base pair (bp) position 14764762 and an A or AA allele at base pair (bp) position 14764839; a C or CC allele at base pair (bp) position 14764762 and a G or GG allele at base pair (bp) position 14764763; a G or GG allele at base pair (bp) position 14764763 and a C or CC allele at base pair (bp) position 14765098; G or GG allele at base pair (bp) position 14764763 and an A or AA allele at base pair (bp) position 14765012; a G or GG allele at base pair (bp) position 14764763 and an A or AA allele at base pair (bp) position 14764839; an A or AA allele at base pair (bp) position 14764839 and a C or CC allele at base pair (bp) position 14765098; an A or AA allele at base pair (bp) position 14764839 and an A or AA allele at base pair (bp) position 14765012 or any combination thereof, thereby identifying and/or selecting a maize plant or maize plant part having increased yield under non-drought conditions, increased yield stability under drought conditions, and/or increased drought tolerance as compared to a control maize plant. In some embodiments, the alleles defining the chromosome intervals can be independently heterozygous or homozygous.

In some embodiments, a method of identifying and/or selecting a maize plant or maize plant part having increased yield under non-drought conditions, increased yield stability under drought conditions, and/or increased drought tolerance is provided, the method comprising: detecting, in said maize plant or maize plant part, the presence of a marker associated with increased yield under non-drought conditions, increased yield stability under drought conditions, and/or increased drought tolerance in a maize plant, wherein said marker is located within a chromosomal interval comprising, consisting essentially of, or consisting of: a chromosomal interval on chromosome 3 defined by and including a G or GG allele at base pair (bp) position 171748815 and a C or CC allele at base pair (bp) position 171752467; a G or GG allele at base pair (bp) position 171748815 and a G or GG allele at base pair (bp) position 171752311; a G or GG allele at base pair (bp) position 171748815 and a C or CC allele at base pair (bp) position 171749536; a G or GG allele at base pair (bp) position 171748815 and an A or AA allele at base pair (bp) position 171749318; a G or GG allele at base pair (bp) position 171748815 and an A or AA allele at base pair (bp) position 171749283; a G or GG allele at base pair (bp) position 171748815 and a C or CC allele at base pair (bp) position 171749273; a C or CC allele at base pair (bp) position 171749273 and a C or CC allele at base pair (bp) position 171752467; a C or CC allele at base pair (bp) position 171749273 and a G or GG allele at base pair (bp) position 171752311; a C or CC allele at base pair (bp) position 171749273 and a C or CC allele at base pair (bp) position 171749536; a C or CC allele at base pair (bp) position 171749273 and an A or AA allele at base pair (bp) position 171749318; a C or CC allele at base pair (bp) position 171749273 and an A or AA allele at base pair (bp) position 171749283; an A or AA allele at base pair (bp) position 171749283 and a C or CC allele at base pair (bp) position 171752467; an A or AA allele at base pair (bp) position 171749283 a G or GG allele at base pair (bp) position 171752311; an A or AA allele at base pair (bp) position 171749283 and a C or CC allele at base pair (bp) position 171749536; an A or AA allele at base pair (bp) position 171749283 and an A or AA allele at base pair (bp) position 171749318; an A or AA allele at base pair (bp) position 171749318 and a C or CC allele at base pair (bp) position 171752467; an A or AA allele at base pair (bp) position 171749318 and a G or GG allele at base pair (bp) position 171752311; an A or AA allele at base pair (bp) position 171749318 and a C or CC allele at base pair (bp) position 171749536; a C or CC allele at base pair (bp) position 171749536 and a C or CC allele at base pair (bp) position 171752467; a C or CC allele at base pair (bp) position 171749536 and a G or GG allele at base pair (bp) position 171752311; or any combination thereof, thereby identifying and/or selecting a maize plant or maize plant part having increased yield under non-drought conditions, increased yield stability under drought conditions, and/or increased drought tolerance as compared to a control maize plant. In some embodiments, the alleles defining the chromosome intervals can be independently heterozygous or homozygous.

In some embodiments, a method of identifying and/or selecting a maize plant or maize plant part having increased yield under non-drought conditions, increased yield stability under drought conditions, and/or increased drought tolerance is provided, the method comprising: detecting, in said maize plant or maize plant part, the presence of a marker associated with increased yield under non-drought conditions, increased yield stability under drought conditions, and/or increased drought tolerance in a maize plant, wherein said marker is located within a chromosomal interval comprising, consisting essentially of, or consisting of: a chromosomal interval on chromosome 1 defined by and including an A or an AA allele at base pair (bp) position 194932443 and a T or TT allele at base pair (bp) position 194935353, thereby identifying and/or selecting a maize plant or maize plant part having increased yield under non-drought conditions, increased yield stability under drought conditions, and/or increased drought tolerance as compared to a control maize plant. In some embodiments, the alleles defining the chromosome intervals can be independently heterozygous or homozygous.

In some embodiments, a method of identifying and/or selecting a maize plant or maize plant part having increased yield under non-drought conditions, increased yield stability under drought conditions, and/or increased drought tolerance is provided, the method comprising: detecting, in said maize plant or maize plant part, the presence of a marker associated with increased yield under non-drought conditions, increased yield stability under drought conditions, and/or increased drought tolerance in a maize plant, wherein said marker is located within a chromosomal interval comprising, consisting essentially of, or consisting of: a chromosomal interval on chromosome 8 defined by and including a C or CC allele at base pair (bp) position 33363546 and an A or AA allele at base pair (bp) position 33368983; a C or CC allele at base pair (bp) position 33363546 and a T or TT allele at base pair (bp) position 33363625; a T or TT allele at base pair (bp) position 33363625 and an A or AA allele at base pair (bp) position 33368983; or any combination thereof, thereby identifying and/or selecting a maize plant or maize plant part having increased yield under non-drought conditions, increased yield stability under drought conditions, and/or increased drought tolerance as compared to a control maize plant. In some embodiments, the alleles defining the chromosome intervals can be independently heterozygous or homozygous.

In some embodiments, a method of identifying and/or selecting a maize plant or maize plant part having increased yield under non-drought conditions, increased yield stability under drought conditions, and/or increased drought tolerance is provided, the method comprising: detecting, in said maize plant or maize plant part, the presence of a marker associated with increased yield under non-drought conditions, increased yield stability under drought conditions, and/or increased drought tolerance in a maize plant, wherein said marker is located within a chromosomal interval comprising, consisting essentially of, or consisting of: a chromosomal interval on chromosome 5 defined by and including a C or CC allele at base pair (bp) position 164854921 and a G or GG allele at base pair (bp) position 164858109; a C or CC allele at base pair (bp) position 164854921 and an A or AA allele at base pair (bp) position 164855482; an A or AA allele at base pair (bp) position 164855482 and a G or GG allele at base pair (bp) position 164858109; or any combination thereof, thereby identifying and/or selecting a maize plant or maize plant part having increased yield under non-drought conditions, increased yield stability under drought conditions, and/or increased drought tolerance as compared to a control maize plant. In some embodiments, the alleles defining the chromosome intervals can be independently heterozygous or homozygous.

In some embodiments, detecting can comprise detecting any combination of markers associated with increased yield under non-drought conditions, increased yield stability under drought conditions, and/or increased drought tolerance in maize as defined herein. Thus, the combination of markers can be any combination of those identified on chromosome 3, those identified on chromosome 10, those identified on chromosome 1, those identified on chromosome 8, or those identified on chromosome 5. Thus, in some embodiments, a method of identifying and/or selecting a maize plant or maize plant part having increased yield under non-drought conditions, increased yield stability under drought conditions, and/or increased drought tolerance is provided, comprising: detecting, in a maize plant or maize plant part, the presence of a combination of markers associated with increased yield under non-drought conditions, increased yield stability under drought conditions, and/or increased drought tolerance in a maize plant, wherein said combination of markers comprises, consists essentially of, or consists of: (a) a G allele at base pair (bp) position 14762443 and a C allele at base pair (bp) position 14765098; (b) a G allele at base pair (bp) position 14762443 and an A allele at base pair (bp) position 14765012; (c) a G allele at base pair (bp) position 14762443 and an A allele at base pair (bp) position 14764839; (d) a G allele at base pair (bp) position 14762443 and a G allele at base pair (bp) position 14764763; (e) a G allele at base pair (bp) position 14762443 and a C allele at base pair (bp) position 14764762; (f) a G allele at base pair (bp) position 14762443 and a G allele at base pair (bp) position 14764658; (g) a G allele at base pair (bp) position 14762443 and a G allele at base pair (bp) position 14764415; (h) a G allele at base pair (bp) position 14764415 and a C allele at base pair (bp) position 14765098; (i) a G allele at base pair (bp) position 14764415 and an A allele at base pair (bp) position 14765012; (j) a G allele at base pair (bp) position 14764415 and an A allele at base pair (bp) position 14764839; (k) a G allele at base pair (bp) position 14764415 and a G allele at base pair (bp) position 14764763; (l) a G allele at base pair (bp) position 14764415 and a C allele at base pair (bp) position 14764762; (m) a G allele at base pair (bp) position 14764415 and a G allele at base pair (bp) position 14764658; (n) a G allele at base pair (bp) position 14764658 and a C allele at base pair (bp) position 14765098; (o) a G allele at base pair (bp) position 14764658 and an A allele at base pair (bp) position 14765012; (p) a G allele at base pair (bp) position 14764658 and an A allele at base pair (bp) position 14764839; (q) a G allele at base pair (bp) position 14764658 and a G allele at base pair (bp) position 14764763; (r) a G allele at base pair (bp) position 14764658 and a C allele at base pair (bp) position 14764762; (s) a C allele at base pair (bp) position 14764762 and a C allele at base pair (bp) position 14765098; (t) a C allele at base pair (bp) position 14764762 and an A allele at base pair (bp) position 14765012; (u) a C allele at base pair (bp) position 14764762 and an A allele at base pair (bp) position 14764839; (v) a C allele at base pair (bp) position 14764762 and a G allele at base pair (bp) position 14764763; (w) a G allele at base pair (bp) position 14764763 and a C allele at base pair (bp) position 14765098; (x) a G allele at base pair (bp) position 14764763 and an A allele at base pair (bp) position 14765012; (y) a G allele at base pair (bp) position 14764763 and an A allele at base pair (bp) position 14764839; (z) an A allele at base pair (bp) position 14764839 and a C allele at base pair (bp) position 14765098; (aa) an A allele at base pair (bp) position 14764839 and an A allele at base pair (bp) position 14765012; (bb) a G allele at base pair (bp) position 171748815 and a C allele at base pair (bp) position 171752467; (cc) a G allele at base pair (bp) position 171748815 and a G allele at base pair (bp) position 171752311; (dd) a G allele at base pair (bp) position 171748815 and a C allele at base pair (bp) position 171749536; (ee) a G allele at base pair (bp) position 171748815 and an A allele at base pair (bp) position 171749318; (ff) a G allele at base pair (bp) position 171748815 and an A allele at base pair (bp) position 171749283; (gg) a G allele at base pair (bp) position 171748815 and a C allele at base pair (bp) position 171749273; (hh) a C allele at base pair (bp) position 171749273 and a C allele at base pair (bp) position 171752467; (ii) a C allele at base pair (bp) position 171749273 and a G allele at base pair (bp) position 171752311; (jj) a C allele at base pair (bp) position 171749273 and a C allele at base pair (bp) position 171749536; (kk) a C allele at base pair (bp) position 171749273 and an A allele at base pair (bp) position 171749318; (ll) a C allele at base pair (bp) position 171749273 and an A allele at base pair (bp) position 171749283; (mm) an A allele at base pair (bp) position 171749283 and a C allele at base pair (bp) position 171752467; (nn) an A allele at base pair (bp) position 171749283 a G allele at base pair (bp) position 171752311; (oo) an A allele at base pair (bp) position 171749283 and a C allele at base pair (bp) position 171749536; (pp) an A allele at base pair (bp) position 171749283 and an A allele at base pair (bp) position 171749318; (qq) an A allele at base pair (bp) position 171749318 and a C allele at base pair (bp) position 171752467; (rr) an A allele at base pair (bp) position 171749318 and a G allele at base pair (bp) position 171752311; (ss) an A allele at base pair (bp) position 171749318 and a C allele at base pair (bp) position 171749536; (tt) a C allele at base pair (bp) position 171749536 and a C allele at base pair (bp) position 171752467; (uu) a C allele at base pair (bp) position 171749536 and a G allele at base pair (bp) position 171752311; (vv) an A allele at base pair (bp) position 194932443 and a T allele at base pair (bp) position 194935353; (ww) a C allele at base pair (bp) position 33363546 and an A allele at base pair (bp) position 33368983; (xx) a C allele at base pair (bp) position 33363546 and a T allele at base pair (bp) position 33363625; (yy) a T allele at base pair (bp) position 33363625 and an A allele at base pair (bp) position 33368983; (zz) a C allele at base pair (bp) position 164854921 and a G allele at base pair (bp) position 164858109; (aaa) a C allele at base pair (bp) position 164854921 and an A allele at base pair (bp) position 164855482; (bbb) an A allele at base pair (bp) position 164855482 and a G allele at base pair (bp) position 164858109; or (ccc) any combination of (a) to (bbb) above, thereby identifying and/or selecting a maize plant or maize plant part having increased yield under non-drought conditions, increased yield stability under drought conditions, and/or increased drought tolerance. In some embodiments, the alleles at the base pair positions defined herein can be independently heterozygous or homozygous.

In some embodiments, a method of identifying and/or selecting a maize plant or maize plant part having increased yield under non-drought conditions, increased yield stability under drought conditions, and/or increased drought tolerance is provided, the method comprising: detecting, in a maize plant or maize plant part, the presence of an allele of at least one marker locus associated with increased yield under non-drought conditions, increased yield stability under drought conditions and/or increased drought tolerance in a maize plant, wherein said allele of at least one marker locus comprises, consists essentially of, or consists of: a G allele at base pair (bp) position 14762443; a C allele at base pair (bp) position 14765098; an A allele at base pair (bp) position 14765012; an A allele at base pair (bp) position 14764839; a G allele at base pair (bp) position 14764763; a C allele at base pair (bp) position 14764762; a G allele at base pair (bp) position 14764658; a G allele at base pair (bp) position 14764415; a G allele at base pair (bp) position 171748815; a C allele at base pair (bp) position 171752467; a G allele at base pair (bp) position 171752311; a C allele at base pair (bp) position 171749536; an A allele at base pair (bp) position 171749318; an A allele at base pair (bp) position 171749283; a C allele at base pair (bp) position 171749273; an A allele at base pair (bp) position 194932443; a T allele at base pair (bp) position 194935353; a C allele at base pair (bp) position 33363546; an A allele at base pair (bp) position 33368983; a T allele at base pair (bp) position 33363625; a C allele at base pair (bp) position 164854921; a G allele at base pair (bp) position 164858109; an A allele at base pair (bp) position 164855482; or any combination thereof, thereby identifying and/or selecting a maize plant or maize plant part having increased yield under non-drought conditions, increased yield stability under drought conditions, and/or increased drought tolerance. In some embodiments, the marker alleles can be independently heterozygous or homozygous.

In representative embodiments, the detecting, in said maize plant or maize plant part, comprises, consists essentially of, or consists of detecting the presence of: a G or GG at base pair (bp) position 14762443; a C or CC at base pair (bp) position 14765098; an AA at base pair (bp) position 14765012; an AA at base pair (bp) position 14764839; a GG at base pair (bp) position 14764763; a CC at base pair (bp) position 14764762; a GG at base pair (bp) position 14764658; a GG at base pair (bp) position 14764415; a G or GG at base pair (bp) position 171748815; a C or CC at base pair (bp) position 171752467; a GG at base pair (bp) position 171752311; a CC at base pair (bp) position 171749536; an AA at base pair (bp) position 171749318; an AA at base pair (bp) position 171749283; a CC at base pair (bp) position 171749273; an AA at base pair (bp) position 194932443; a T or TT at base pair (bp) position 194935353; a C or CC at base pair (bp) position 33363546; an A or AA at base pair (bp) position 33368983; a TT at base pair (bp) position 33363625; a C or CC at base pair (bp) position 164854921; a G or CC at base pair (bp) position 164858109; an AA at base pair (bp) position 164855482, or any combination thereof.

In some embodiments, a method of identifying and/or selecting a maize plant or maize plant part having increased yield under non-drought conditions, increased yield stability under drought conditions, and/or increased drought tolerance is provided, the method comprising: detecting, in a maize plant or maize plant part, the presence of an allele of at least one marker locus associated with increased yield under non-drought conditions, increased yield stability under drought conditions and/or increased drought tolerance in a maize plant, wherein said allele of at least one marker locus is selected from the group comprised of INDEL 1 and INDEL2 found in Table 3.

Thus, as described herein, methods for identifying and/or selecting a maize plant or maize plant part having increased yield under non-drought conditions, increased yield stability under drought conditions, and/or increased drought tolerance can comprise detecting the presence of a marker or a combination of markers associated with increased yield under non-drought conditions, increased yield stability under drought conditions, and/or increased drought tolerance in a maize plant as defined herein. Any combination of genetic markers of this invention can be used to identify and/or select a maize plant or germplasm having increased yield under non-drought conditions, increased yield stability under drought conditions, and/or increased drought tolerance.

The subject matter disclosed herein also relates to methods for producing maize plants comprising detecting the presence of a marker allele or a locus associated with increased yield under non-drought conditions, increased yield stability under drought conditions, and/or increased drought tolerance in a donor maize plant according to the methods described herein and transferring a nucleic acid sequence comprising at least one allele thus detected from the donor plant to a maize plant not having increased yield under non-drought conditions, increased yield stability under drought conditions, and/or increased drought tolerance. The transfer of the nucleic acid sequence can be performed by any known or later developed methods for transferring genetic material between plants.

Thus, the present invention encompasses methods of plant breeding and methods of selecting/identifying plants, in particular maize plants, particularly cultivated maize plants as breeder plants for use in breeding programs or cultivated maize plants having desired genotypic or potential phenotypic properties, in particular related to producing valuable maize plants, also referred to herein as commercially valuable plants. Herein, a cultivated plant is defined as a plant

TABLE 3

Significant Insertion/Deletion Markers from FBAM Study a

| INDEL | Analysis_ID | Trait | Marker | GeneModelID |
|---|---|---|---|---|
| 1 | Sweet_SS_K_1PC | YGSMN_2008_irrigated | chr3_171748915_A_AGA | GRMZM2G039365 |
| 2 | Sweet_NSS_K_6PC | YGSMN_2009_irrigated | chr10_14764880_GCATG_G | GRMZM2G173669 | b

| INDEL | Chrom. | Site | NegLogP | Num_Ind | Allele_1 | Allele1_effect | Allele_2 | Allele2_effect |
|---|---|---|---|---|---|---|---|---|
| 1 | chr3 | 171748915 | 3.6662304 | 142 | D | 2.1373275 | I | −2.1373275 |
| 2 | chr10 | 14764880 | 3.5313721 | 229 | D | −2.11413 | I | 2.11413 | being purposely selected or having been derived from a plant having been purposely selected in agricultural or horticultural practice for having desired genotypic or potential phenotypic properties, for example, a plant obtained by inbreeding.

The presently disclosed subject matter thus also provides methods for selecting a plant of the species Zea mays exhibiting increased yield under non-drought conditions, increased yield stability under drought conditions, and/or increased drought tolerance, the methods comprising detecting in the plant the presence of one or more genetic markers associated with increased yield under non-drought conditions, increased yield stability under drought conditions, and/or increased drought tolerance as defined herein. In an exemplary embodiment, a method for selecting such a plant comprises providing a sample of genomic DNA from a maize plant or maize plant part; and detecting in the sample of genomic DNA at least one genetic marker associated with increased yield under non-drought conditions, increased yield stability under drought conditions, and/or increased drought tolerance as described herein. In some embodiments, the detecting can comprise detecting one or more SNPs, a combination of SNPs (haplotype), and/or SNPs located in chromosomal intervals that are associated with increased yield under non-drought conditions, increased yield stability under drought conditions, and/or increased drought tolerance in a maize plant.

The providing of a sample of genomic DNA from a maize plant can be performed by standard DNA isolation methods well known in the art.

As is well known in the art, the detecting of a genetic marker can in some embodiments comprise the use of one or more sets of primer pairs that can be used to produce one or more amplification products that are suitable for identifying, for example, a SNP. Primer pairs can be readily prepared using the nucleotide sequences of SEQ ID NO:1, SEQ ID NO:2, SEQ ID NO:3, SEQ ID NO:4, and/or SEQ ID NO:5, and the positions and alleles of the markers as provided herein.

In some embodiments of this invention, a method is provided, said method comprising transfer by introgression of the nucleic acid sequence conferring increased yield under non-drought conditions, increased yield stability under drought conditions, and/or increased drought tolerance from a donor maize plant into a recipient maize plant by crossing the plants. This transfer can be accomplished by using traditional breeding techniques. Loci associated with increased yield under non-drought conditions, increased yield stability under drought conditions, and/or increased drought tolerance in maize plants are introgressed in some embodiments into commercial corn varieties using marker-assisted selection (MAS) or marker-assisted breeding (MAB). MAS and MAB involves the use of one or more of the molecular markers, identified as having a significant likelihood of co-segregation with a desired trait, and used for the identification and selection of those offspring plants that contain one or more of the genes that encode the desired trait. As disclosed herein, such identification and selection is based on selection of one or more SNP alleles of this invention or markers associated therewith. MAB can also be used to develop near-isogenic lines (NIL) harboring one or more alleles of interest associated with increased yield under non-drought conditions, increased yield stability under drought conditions, and/or increased drought tolerance in a maize plant, allowing a more detailed study of an effect of such allele(s), and is also an effective method for development of backcross inbred line (BIL) populations. Maize plants developed according to these embodiments can in some embodiments derive a majority of their traits from the recipient plant and derive increased yield under non-drought conditions, increased yield stability under drought conditions, and/or increased drought tolerance from the donor plant. MAB/MAS techniques increase the efficiency of backcrossing and introgressing genes using marker-assisted selection (MAS) or marker-assisted breeding (MAB).

Thus, traditional breeding techniques can be used to introgress a nucleic acid sequence associated with increased yield under non-drought conditions, increased yield stability under drought conditions, and/or increased drought tolerance into a recipient maize plant not having increased yield under non-drought conditions, increased yield stability under drought conditions, and/or increased drought tolerance. For example, inbred maize lines having increased yield under non-drought conditions, increased yield stability under drought conditions, and/or increased drought tolerance can be developed using the techniques of recurrent selection and backcrossing, selfing, and/or dihaploids, or any other technique used to make parental lines. In a method of recurrent selection and backcrossing, increased yield under non-drought conditions, increased yield stability under drought conditions, and/or increased drought tolerance can be introgressed into a target recipient plant (the recurrent parent) by crossing the recurrent parent with a first donor plant, which differs from the recurrent parent and is referred to herein as the "non-recurrent parent." The recurrent parent can be a plant that does not exhibit or exhibits a low level of increased yield under non-drought conditions, increased yield stability under drought conditions, and/or increased drought tolerance, but which, in some embodiments, comprises commercially desirable characteristics, such as, but not limited to disease and/or insect resistance, valuable nutritional characteristics, valuable additional abiotic stress tolerance (including, but not limited to, additional drought tolerance, salt tolerance), and the like. In some embodiments, the non-recurrent parent exhibits increased yield under non-drought conditions, increased yield stability under drought conditions, and/or increased drought tolerance and comprises a nucleic acid sequence that is associated with increased yield under non-drought conditions, increased yield stability under drought conditions, and/or increased drought tolerance. The non-recurrent parent can be any maize variety or inbred line that is cross-fertile with the recurrent parent. In some embodiments, a recurrent parent plant can be the control plant against which increased yield under non-drought conditions, increased yield stability under drought conditions, and/or increased drought tolerance can be measured.

In some embodiments, the progeny resulting from a cross between the recurrent parent and non-recurrent parent are backcrossed to the recurrent parent. The resulting plant population is then screened for the desired characteristics, which screening can occur in a number of different ways. For instance, the population can be screened using phenotypic pathology screens or quantitative bioassays as are known in the art. Alternatively, instead of using bioassays, MAB can be performed using one or more of the hereinbefore described molecular markers, hybridization probes, or polynucleotides to identify those progeny that comprise a nucleic acid sequence associated with increased yield under non-drought conditions, increased yield stability under drought conditions, and/or increased drought tolerance. Also, MAB can be used to confirm the results obtained from the quantitative bioassays. In some embodiments, the markers defined herein are suitable to select proper offspring plants by genotypic screening.

Following screening, the F1 hybrid plants that exhibit a phenotype of increased yield under non-drought conditions, increased yield stability under drought conditions, and/or increased drought tolerance or, in some embodiments, the genotype, and thus comprise the requisite nucleic acid sequence associated with increased yield under non-drought conditions, increased yield stability under drought conditions, and/or increased drought tolerance, can then be selected and backcrossed to the recurrent parent for one or more generations in order to allow for the maize plant to become increasingly inbred. This process can be performed for one, two, three, four, five, six, seven, eight, or more generations.

Thus, a marker that demonstrates linkage with a locus affecting a desired phenotypic trait provides a useful tool for selection of the trait in a plant population. This is particularly true where the phenotype may be difficult to assay or occurs at a late stage in plant development. Since DNA marker assays are less laborious and take up less physical space than field phenotyping, much larger populations can be assayed, increasing the chances of finding a recombinant plant with the target segment moved from the donor line moved to the recipient line. The closer the linkage, the more useful the marker, as recombination is less likely to occur between the marker and the gene that causes or imparts the trait. In addition, having flanking markers can decrease the chance that false positive selection will occur. Ideally, a marker is in the gene itself, so that recombination cannot occur between the marker and the gene. Such a marker is called a "perfect marker."

The availability of integrated linkage maps of the maize genome containing increasing densities of public maize markers has facilitated maize genetic mapping and MAS. See, e.g. MaizeGDB (maizegdb.org/map.php).

Of all the molecular marker types, SNPs are the most abundant and have the potential to provide the highest genetic map resolution (Bhattramakki et al., *Plant Molec. Biol.* 48:539 (2002)). SNPs can be assayed in a so-called "ultra-high-throughput" fashion because they do not require large amounts of nucleic acid and automation of the assay is straight-forward. SNPs also have the benefit of being relatively low-cost systems. These three factors together make SNPs highly attractive for use in MAS. Several methods are available for SNP genotyping, including but not limited to, hybridization, primer extension, oligonucleotide ligation, nuclease cleavage, minisequencing and coded spheres. Such methods have been reviewed in various publications: Gut, *Hum. Mutat.* 17:475 (2001); Shi, *Clin. Chem.* 47:164 (2001); Kwok, *Pharmacogenomics* 1:95 (2000); Bhattramakki and Rafalski, *Discovery and application of single nucleotide polymorphism markers in plants*, in PLANT GENOTYPING: THE DNA FINGERPRINTING OF PLANTS, CABI Publishing, Wallingford (2001). A wide range of commercially available technologies utilize these and other methods to interrogate SNPs, including Masscode™ (Qiagen, Germantown, Md.), Invader® (Hologic, Madison, Wis.), SnapShot® (Applied Biosystems, Foster City, Calif.), Taqman® (Applied Biosystems, Foster City, Calif.) and Beadarrays™ (Illumina, San Diego, Calif.).

Accordingly, the markers of the present invention can be used in marker-assisted selection methods to identify and/or select and/or produce progeny having a genetic marker associated with increased yield under non-drought conditions, increased yield stability under drought conditions, and/or increased drought tolerance in maize. Thus, in some embodiments, the present invention relates to methods for producing maize plants comprising an allele associated with increased yield under non-drought conditions, increased yield stability under drought conditions, and/or increased drought tolerance, comprising detecting the presence of at least one allele associated with increased yield under non-drought conditions, increased yield stability under drought conditions, and/or increased drought tolerance in a donor maize plant as described herein, crossing the donor maize plant with a second maize plant or germplasm, and detecting in the progeny plant(s) the presence of said at least one allele associated with increased yield under non-drought conditions, increased yield stability under drought conditions, and/or increased drought tolerance, thereby transferring the at least one allele associated with increased yield under non-drought conditions, increased yield stability under drought conditions, and/or increased drought tolerance thus detected from the donor maize plant to the second maize plant and producing a maize plant (e.g., progeny plant) having increased yield under non-drought conditions, increased yield stability under drought conditions, and/or increased drought tolerance. In some embodiments, the second maize plant does not comprise increased yield under non-drought conditions, increased yield stability under drought conditions, and/or increased drought tolerance. The transfer of the allele associated with increased yield under non-drought conditions, increased yield stability under drought conditions, and/or increased drought tolerance can be performed by any of the methods described herein.

Thus, in some embodiments, a method of producing a maize plant having increased yield under non-drought conditions, increased yield stability under drought conditions, and/or increased drought tolerance is provided, the method comprising: detecting, in a maize plant, at least one a marker locus that is associated with increased yield under non-drought conditions, increased yield stability under drought conditions, and/or increased drought tolerance, wherein said at least one marker locus is located within a chromosomal interval comprising, consisting essentially of, or consisting of: (a) a chromosome interval on chromosome 10 defined by and including base pair (bp) position 14762443 to base pair (bp) position 14765098; (b) a chromosome interval on chromosome 10 defined by and including base pair (bp) position 14762443 to base pair (bp) position 14765012; (c) a chromosome interval on chromosome 10 defined by and including base pair (bp) position 14762443 to base pair (bp) position 14764839; (d) a chromosome interval on chromosome 10 defined by and including base pair (bp) position 14762443 to base pair (bp) position 14764763; (e) a chromosome interval on chromosome 10 defined by and including base pair (bp) position 14762443 to base pair (bp) position 14764762; (f) a chromosome interval on chromosome 10 defined by and including base pair (bp) position 14762443 to base pair (bp) position 14764658; (g) a chromosome interval on chromosome 10 defined by and including base pair (bp) position 14762443 to base pair (bp) position 14764415; (h) a chromosome interval on chromosome 10 defined by and including base pair (bp) position 14764415 to base pair (bp) position 14765098; (i) a chromosome interval on chromosome 10 defined by and including base pair (bp) position 14764415 to base pair (bp) position 14765012; (j) a chromosome interval on chromosome 10 defined by and including base pair (bp) position 14764415 to base pair (bp) position 14764839; (k) a chromosome interval on chromosome 10 defined by and including base pair (bp) position 14764415 to base pair (bp) position 14764763; (l) a chromosome interval on chromosome 10 defined by and including base pair (bp) position 14764415 to base pair (bp) position 14764762; (m) a chromosome interval on chromosome 10 defined by and including base pair (bp) position 14764415 to base pair (bp) position 14764658; (n) a chromosome interval on chromosome 10 defined by and including base pair (bp) position 14764658 to base pair (bp) position 14765098; (o) a chromosome interval on chromosome 10 defined by and including base pair (bp) position 14764658 to base pair (bp) position 14765012; (p) a chromosome interval on chromosome 10 defined by and including base pair (bp) position 14764658 to base pair (bp) position 14764839; (q) a chromosome interval on chromosome 10 defined by and including base pair (bp) position 14764658 to base pair (bp) position 14764763; (r) a chromosome interval on chromosome 10 defined by and including base pair (bp) position 14764658 to base pair (bp) position 14764762; (s) a chromosome interval on chromosome 10 defined by and including base pair (bp) position 14764762 to base pair (bp) position 14765098; (t) a chromosome interval on chromosome 10 defined by and including base pair (bp) position 14764762 to base pair (bp) position 14765012; (u) a chromosome interval on chromosome 10 defined by and including base pair (bp) position 14764762 to base pair (bp) position 14764839; (v) a chromosome interval on chromosome 10 defined by and including base pair (bp) position 14764762 to base pair (bp) position 14764763; (w) a chromosome interval on chromosome 10 defined by and including base pair (bp) position 14764763 to base pair (bp) position 14765098; (x) a chromosome interval on chromosome 10 defined by and including base pair (bp) position 14764763 to base pair (bp) position 14765012; (y) a chromosome interval on chromosome 10 defined by and including base pair (bp) position 14764763 to base pair (bp) position 14764839; (z) a chromosome interval on chromosome 10 defined by and including base pair (bp) position 14764839 to base pair (bp) position 14765098; (aa) a chromosome interval on chromosome 10 defined by and including base pair (bp) position 14764839 to base pair (bp) position 14765012; (bb) a chromosome interval on chromosome 3 defined by and including base pair (bp) position 171748815 to base pair (bp) position 171752467; (cc) a chromosome interval on chromosome 3 defined by and including base pair (bp) position 171748815 to base pair (bp) position 171752311; (dd) a chromosome interval on chromosome 3 defined by and including base pair (bp) position 171748815 to base pair (bp) position 171749536; (ee) a chromosome interval on chromosome 3 defined by and including base pair (bp) position 171748815 to base pair (bp) position 171749318; (ff) a chromosome interval on chromosome 3 defined by and including base pair (bp) position 171748815 to base pair (bp) position 171749283; (gg) a chromosome interval on chromosome 3 defined by and including base pair (bp) position 171748815 to base pair (bp) position 171749273; (hh) a chromosome interval on chromosome 3 defined by and including base pair (bp) position 171749273 to base pair (bp) position 171752467; (ii) a chromosome interval on chromosome 3 defined by and including base pair (bp) position 171749273 to base pair (bp) position 171752311; (jj) a chromosome interval on chromosome 3 defined by and including base pair (bp) position 171749273 to base pair (bp) position 171749536; (kk) a chromosome interval on chromosome 3 defined by and including base pair (bp) position 171749273 to base pair (bp) position 171749318; (ll) a chromosome interval on chromosome 3 defined by and including base pair (bp) position 171749273 to base pair (bp) position 171749283; (mm) a chromosome interval on chromosome 3 defined by and including base pair (bp) position 171749283 to base pair (bp) position 171752467; (nn) a chromosome interval on chromosome 3 defined by and including base pair (bp) position 171749283 to base pair (bp) position 171752311; (oo) a chromosome interval on chromosome 3 defined by and including base pair (bp) position 171749283 to base pair (bp) position 171749536; (pp) a chromosome interval on chromosome 3 defined by and including base pair (bp) position 171749283 to base pair (bp) position 171749318; (qq) a chromosome interval on chromosome 3 defined by and including base pair (bp) position 171749318 to base pair (bp) position 171752467; (rr) a chromosome interval on chromosome 3 defined by and including base pair (bp) position 171749318 to base pair (bp) position 171752311; (ss) a chromosome interval on chromosome 3 defined by and including base pair (bp) position 171749318 to base pair (bp) position 171749536; (tt) a chromosome interval on chromosome 3 defined by and including base pair (bp) position 171749536 to base pair (bp) position 171752467; (uu) a chromosome interval on chromosome 3 defined by and including base pair (bp) position 171749536 to base pair (bp) position 171752311; (vv) a chromosome interval on chromosome 1 defined by and including base pair (bp) position 194932443 to base pair (bp) position 194935353; (ww) a chromosome interval on chromosome 8 defined by and including base pair (bp) position 33363546 to base pair (bp) position 33368983; (xx) a chromosome interval on chromosome 8 defined by and including base pair (bp) position 33363546 to base pair (bp) position 33363625; (yy) a chromosome interval on chromosome 8 defined by and including base pair (bp) position 33363625 to base pair (bp) position 33368983; (zz) a chromosome interval on chromosome 5 defined by and including base pair (bp) position 164854921 to base pair (bp) position 164858109; (aaa) a chromosome interval on chromosome 5 defined by and including base pair (bp) position 164854921 to base pair (bp) position 164855482; (bbb) a chromosome interval on chromosome 5 defined by and including base pair (bp) position 164855482 to base pair (bp) position 164858109; or (ccc) any combination of (a) to (bbb) above, thereby producing a plant having increased yield under non-drought conditions, increased yield stability under drought conditions, and/or increased drought tolerance as compared to a control maize plant.

In some embodiments, an allele is detected at the base pair positions of the chromosome intervals described herein, wherein said allele comprises, consists essentially of, or consists of: a G or GG at base pair (bp) position 14762443; a C or CC at base pair (bp) position 14765098; an A or AA at base pair (bp) position 14765012; an A or AA at base pair (bp) position 14764839; a G or GG at base pair (bp) position 14764763; a C or CC at base pair (bp) position 14764762; a G or GG at base pair (bp) position 14764658; a G or GG at base pair (bp) position 14764415; a G at base pair (bp) position 171748815; a C at base pair (bp) position 171752467; a G or GG at base pair (bp) position 171752311; a C or CC at base pair (bp) position 171749536; an A or AA at base pair (bp) position 171749318; an A or AA at base pair (bp) position 171749283; a C or CC at base pair (bp) position 171749273; an A or AA at base pair (bp) position 194932443; a T or TT at base pair (bp) position 194935353; a C or CC at base pair (bp) position 33363546; an A or AA at base pair (bp) position 33368983; a T or TT at base pair (bp) position 33363625; a C or CC at base pair (bp) position 164854921; a G or GG at base pair (bp) position 164858109; and/or an A or AA at base pair (bp) position 164855482. In some embodiments, the alleles defining the chromosome intervals can be independently heterozygous or homozygous.

In some embodiments, a method of producing a maize plant having increased yield under non-drought conditions, increased yield stability under drought conditions, and/or increased drought tolerance is provided, the method comprising: detecting, in a maize plant, the presence of a marker associated with increased yield under non-drought conditions, increased yield stability under drought conditions, and/or increased drought tolerance in a maize plant, wherein said marker is located within a chromosomal interval comprising, consisting essentially of, or consisting of: a chromosomal interval on chromosome 10 defined by and including a G or GG allele at base pair (bp) position 14762443 and a C or CC allele at base pair (bp) position 14765098; a G or GG allele at base pair (bp) position 14762443 and an A or AA allele at base pair (bp) position 14765012; a G or GG allele at base pair (bp) position 14762443 and an A or AA allele at base pair (bp) position 14764839; a G or GG allele at base pair (bp) position 14762443 and a G or GG allele at base pair (bp) position 14764763; a G or GG allele at base pair (bp) position 14762443 and a C or CC allele at base pair (bp) position 14764762; a G or GG allele at base pair (bp) position 14762443 and a G or GG allele at base pair (bp) position 14764658; a G or GG allele at base pair (bp) position 14762443 and a G or GG allele at base pair (bp) position 14764415; a G or GG allele at base pair (bp) position 14764415 and a C or CC allele at base pair (bp) position 14765098; a G or GG allele at base pair (bp) position 14764415 and an A or AA allele at base pair (bp) position 14765012; a G or GG allele at base pair (bp) position 14764415 and an A allele at base pair (bp) position 14764839; a G or GG allele at base pair (bp) position 14764415 and a G allele at base pair (bp) position 14764763; a G or GG allele at base pair (bp) position 14764415 and a C or CC allele at base pair (bp) position 14764762; a G or GG allele at base pair (bp) position 14764415 and a G or GG allele at base pair (bp) position 14764658; a G or GG allele at base pair (bp) position 14764658 and a C allele at base pair (bp) position 14765098; a G or GG allele at base pair (bp) position 14764658 and an A or AA allele at base pair (bp) position 14765012; a G or GG allele at base pair (bp) position 14764658 and an A or AA allele at base pair (bp) position 14764839; a G or GG allele at base pair (bp) position 14764658 and a G or GG allele at base pair (bp) position 14764763; a G or GG allele at base pair (bp) position 14764658 and a C or CC allele at base pair (bp) position 14764762; a C or CC allele at base pair (bp) position 14764762 and a C or CC allele at base pair (bp) position 14765098; a C or CC allele at base pair (bp) position 14764762 and an A or AA allele at base pair (bp) position 14765012; a C or CC allele at base pair (bp) position 14764762 and an A or AA allele at base pair (bp) position 14764839; a C or CC allele at base pair (bp) position 14764762 and a G or GG allele at base pair (bp) position 14764763; a G or GG allele at base pair (bp) position 14764763 and a C or CC allele at base pair (bp) position 14765098; G or GG allele at base pair (bp) position 14764763 and an A or AA allele at base pair (bp) position 14765012; a G or GG allele at base pair (bp) position 14764763 and an A or AA allele at base pair (bp) position 14764839; an A or AA allele at base pair (bp) position 14764839 and a C or CC allele at base pair (bp) position 14765098; an A or AA allele at base pair (bp) position 14764839 and an A or AA allele at base pair (bp) position 14765012, or any combination thereof, thereby producing a maize plant having increased yield under non-drought conditions, increased yield stability under drought conditions, and/or increased drought tolerance as compared to a control maize plant. In some embodiments, the alleles defining the chromosome intervals can be independently heterozygous or homozygous.

In some embodiments, a method of producing a maize plant having increased yield under non-drought conditions, increased yield stability under drought conditions, and/or increased drought tolerance is provided, the method comprising: detecting, in a maize plant, the presence of a marker associated with increased yield under non-drought conditions, increased yield stability under drought conditions, and/or increased drought tolerance in a maize plant, wherein said marker is located within a chromosomal interval comprising, consisting essentially of, or consisting of: a chromosomal interval on chromosome 3 defined by and including a G or GG allele at base pair (bp) position 171748815 and a C or CC allele at base pair (bp) position 171752467; a G or GG allele at base pair (bp) position 171748815 and a G or GG allele at base pair (bp) position 171752311; a G or GG allele at base pair (bp) position 171748815 and a C or CC allele at base pair (bp) position 171749536; a G or GG allele at base pair (bp) position 171748815 and an A or AA allele at base pair (bp) position 171749318; a G or GG allele at base pair (bp) position 171748815 and an A or AA allele at base pair (bp) position 171749283; a G or GG allele at base pair (bp) position 171748815 and a C or CC allele at base pair (bp) position 171749273; a C or CC allele at base pair (bp) position 171749273 and a C or CC allele at base pair (bp) position 171752467; a C or CC allele at base pair (bp) position 171749273 and a G or GG allele at base pair (bp) position 171752311; a C or CC allele at base pair (bp) position 171749273 and a C or CC allele at base pair (bp) position 171749536; a C or CC allele at base pair (bp) position 171749273 and an A or AA allele at base pair (bp) position 171749318; a C or CC allele at base pair (bp) position 171749273 and an A or AA allele at base pair (bp) position 171749283; an A or AA allele at base pair (bp) position 171749283 and a C or CC allele at base pair (bp) position 171752467; an A or AA allele at base pair (bp) position 171749283 a G or GG allele at base pair (bp) position 171752311; an A or AA allele at base pair (bp) position 171749283 and a C or CC allele at base pair (bp) position 171749536; an A or AA allele at base pair (bp) position 171749283 and an A or AA allele at base pair (bp) position 171749318; an A or AA allele at base pair (bp) position 171749318 and a C or CC allele at base pair (bp) position 171752467; an A or AA allele at base pair (bp) position 171749318 and a G or GG allele at base pair (bp) position 171752311; an A or AA allele at base pair (bp) position 171749318 and a C or CC allele at base pair (bp) position 171749536; a C or CC allele at base pair (bp) position 171749536 and a C or CC allele at base pair (bp) position 171752467; a C or CC allele at base pair (bp) position 171749536 and a G or GG allele at base pair (bp) position 171752311; or any combination thereof, thereby producing a maize plant having increased yield under non-drought conditions, increased yield stability under drought conditions, and/or increased drought tolerance as compared to a control maize plant. In some embodiments, the alleles defining the chromosome intervals can be independently heterozygous or homozygous.

In some embodiments, a method of producing a maize plant having increased yield under non-drought conditions, increased yield stability under drought conditions, and/or increased drought tolerance is provided, the method comprising: detecting, in a maize plant, the presence of a marker associated with increased yield under non-drought conditions, increased yield stability under drought conditions, and/or increased drought tolerance in a maize plant, wherein said marker is located within a chromosomal interval comprising, consisting essentially of, or consisting of: a chromosomal interval on chromosome 1 defined by and including an A or an AA allele at base pair (bp) position 194932443 and a T or TT allele at base pair (bp) position 194935353, thereby identifying and/or selecting a maize plant having increased yield under non-drought conditions, increased yield stability under drought conditions, and/or increased drought tolerance as compared to a control maize plant. In some embodiments, the alleles defining the chromosome intervals can be independently heterozygous or homozygous.

In some embodiments, a method of producing a maize plant having increased yield under non-drought conditions, increased yield stability under drought conditions, and/or increased drought tolerance is provided, the method comprising: detecting, in a maize plant, the presence of a marker associated with increased yield under non-drought conditions, increased yield stability under drought conditions, and/or increased drought tolerance in a maize plant, wherein said marker is located within a chromosomal interval comprising, consisting essentially of, or consisting of: a chromosomal interval on chromosome 8 defined by and including a C or CC allele at base pair (bp) position 33363546 and an A or AA allele at base pair (bp) position 33368983; a C or CC allele at base pair (bp) position 33363546 and a T or TT allele at base pair (bp) position 33363625; a T or TT allele at base pair (bp) position 33363625 and an A or AA allele at base pair (bp) position 33368983; or any combination thereof, thereby producing a maize plant having increased yield under non-drought conditions, increased yield stability under drought conditions, and/or increased drought tolerance as compared to a control maize plant. In some embodiments, the alleles defining the chromosome intervals can be independently heterozygous or homozygous.

In some embodiments, a method of producing a maize plant having increased yield under non-drought conditions, increased yield stability under drought conditions, and/or increased drought tolerance is provided, the method comprising: detecting, in a maize plant, the presence of a marker associated with increased yield under non-drought conditions, increased yield stability under drought conditions, and/or increased drought tolerance in a maize plant, wherein said marker is located within a chromosomal interval comprising, consisting essentially of, or consisting of: a chromosomal interval on chromosome 5 defined by and including a C or CC allele at base pair (bp) position 164854921 and a G or GG allele at base pair (bp) position 164858109; a C or CC allele at base pair (bp) position 164854921 and an A or AA allele at base pair (bp) position 164855482; an A or AA allele at base pair (bp) position 164855482 and a G or GG allele at base pair (bp) position 164858109; or any combination thereof, thereby providing a maize plant having increased yield under non-drought conditions, increased yield stability under drought conditions, and/or increased drought tolerance as compared to a control maize plant. In some embodiments, the alleles defining the chromosome intervals can be independently heterozygous or homozygous.

In some embodiments, detecting can comprise detecting one or more markers associated with increased yield under non-drought conditions, increased yield stability under drought conditions, and/or increased drought tolerance in maize as defined herein, in any combination. Thus, a combination of markers for detection can be any combination of markers identified on chromosome 3, markers identified on chromosome 10, markers identified on chromosome 1, markers identified on chromosome 8, and/or markers identified on chromosome 5. Thus, in some embodiments, a method of providing a maize plant having increased yield under non-drought conditions, increased yield stability under drought conditions, and/or increased drought tolerance is provided, comprising: detecting, in a maize plant, the presence of a combination of markers associated with increased yield under non-drought conditions, increased yield stability under drought conditions, and/or increased drought tolerance in a maize plant, wherein said combination of markers comprises, consists essentially of, or consists of: (a) a G allele at base pair (bp) position 14762443 and a C allele at base pair (bp) position 14765098; (b) a G allele at base pair (bp) position 14762443 and an A allele at base pair (bp) position 14765012; (c) a G allele at base pair (bp) position 14762443 and an A allele at base pair (bp) position 14764839; (d) a G allele at base pair (bp) position 14762443 and a G allele at base pair (bp) position 14764763; (e) a G allele at base pair (bp) position 14762443 and a C allele at base pair (bp) position 14764762; (f) a G allele at base pair (bp) position 14762443 and a G allele at base pair (bp) position 14764658; (g) a G allele at base pair (bp) position 14762443 and a G allele at base pair (bp) position 14764415; (h) a G allele at base pair (bp) position 14764415 and a C allele at base pair (bp) position 14765098; (i) a G allele at base pair (bp) position 14764415 and an A allele at base pair (bp) position 14765012; (j) a G allele at base pair (bp) position 14764415 and an A allele at base pair (bp) position 14764839; (k) a G allele at base pair (bp) position 14764415 and a G allele at base pair (bp) position 14764763; (l) a G allele at base pair (bp) position 14764415 and a C allele at base pair (bp) position 14764762; (m) a G allele at base pair (bp) position 14764415 and a G allele at base pair (bp) position 14764658; (n) a G allele at base pair (bp) position 14764658 and a C allele at base pair (bp) position 14765098; (o) a G allele at base pair (bp) position 14764658 and an A allele at base pair (bp) position 14765012; (p) a G allele at base pair (bp) position 14764658 and an A allele at base pair (bp) position 14764839; (q) a G allele at base pair (bp) position 14764658 and a G allele at base pair (bp) position 14764763; (r) a G allele at base pair (bp) position 14764658 and a C allele at base pair (bp) position 14764762; (s) a C allele at base pair (bp) position 14764762 and a C allele at base pair (bp) position 14765098; (t) a C allele at base pair (bp) position 14764762 and an A allele at base pair (bp) position 14765012; (u) a C allele at base pair (bp) position 14764762 and an A allele at base pair (bp) position 14764839; (v) a C allele at base pair (bp) position 14764762 and a G allele at base pair (bp) position 14764763; (w) a G allele at base pair (bp) position 14764763 and a C allele at base pair (bp) position 14765098; (x) a G allele at base pair (bp) position 14764763 and an A allele at base pair (bp) position 14765012; (y) a G allele at base pair (bp) position 14764763 and an A allele at base pair (bp) position 14764839; (z) an A allele at base pair (bp) position 14764839 and a C allele at base pair (bp) position 14765098; (aa) an A allele at base pair (bp) position 14764839 and an A allele at base pair (bp) position 14765012; (bb) a G allele at base pair (bp) position 171748815 and a C allele at base pair (bp) position 171752467; (cc) a G allele at base pair (bp) position 171748815 and a G allele at base pair (bp) position 171752311; (dd) a G allele at base pair (bp) position 171748815 and a C allele at base pair (bp) position 171749536; (ee) a G allele at base pair (bp) position 171748815 and an A allele at base pair (bp) position 171749318; (ff) a G allele at base pair (bp) position 171748815 and an A allele at base pair (bp) position 171749283; (gg) a G allele at base pair (bp) position 171748815 and a C allele at base pair (bp) position 171749273; (hh) a C allele at base pair (bp) position 171749273 and a C allele at base pair (bp) position 171752467; (ii) a C allele at base pair (bp) position 171749273 and a G allele at base pair (bp) position 171752311; (jj) a C allele at base pair (bp) position 171749273 and a C allele at base pair (bp) position 171749536; (kk) a C allele at base pair (bp) position 171749273 and an A allele at base pair (bp) position 171749318; (ll) a C allele at base pair (bp) position 171749273 and an A allele at base pair (bp) position 171749283; (mm) an A allele at base pair (bp) position 171749283 and a C allele at base pair (bp) position 171752467; (nn) an A allele at base pair (bp) position 171749283 a G allele at base pair (bp) position 171752311; (oo) an A allele at base pair (bp) position 171749283 and a C allele at base pair (bp) position 171749536; (pp) an A allele at base pair (bp) position 171749283 and an A allele at base pair (bp) position 171749318; (qq) an A allele at base pair (bp) position 171749318 and a C allele at base pair (bp) position 171752467; (rr) an A allele at base pair (bp) position 171749318 and a G allele at base pair (bp) position 171752311; (ss) an A allele at base pair (bp) position 171749318 and a C allele at base pair (bp) position 171749536; (tt) a C allele at base pair (bp) position 171749536 and a C allele at base pair (bp) position 171752467; (uu) a C allele at base pair (bp) position 171749536 and a G allele at base pair (bp) position 171752311; (vv) an A allele at base pair (bp) position 194932443 and a T allele at base pair (bp) position 194935353; (ww) a C allele at base pair (bp) position 33363546 and an A allele at base pair (bp) position 33368983; (xx) a C allele at base pair (bp) position 33363546 and a T allele at base pair (bp) position 33363625; (yy) a T allele at base pair (bp) position 33363625 and an A allele at base pair (bp) position 33368983; (zz) a C allele at base pair (bp) position 164854921 and a G allele at base pair (bp) position 164858109; (aaa) a C allele at base pair (bp) position 164854921 and an A allele at base pair (bp) position 164855482; (bbb) an A allele at base pair (bp) position 164855482 and a G allele at base pair (bp) position 164858109; or (ccc) any combination of (a) to (bbb) above, thereby producing a maize plant having increased yield under non-drought conditions, increased yield stability under drought conditions, and/or increased drought tolerance. In some embodiments, the alleles at the base pair positions defined herein can be independently heterozygous or homozygous.

In some embodiments, a method of producing a maize plant having increased yield under non-drought conditions, increased yield stability under drought conditions, and/or increased drought tolerance is provided, the method comprising: detecting, in a maize plant, the presence of an allele of at least one marker locus associated with increased yield under non-drought conditions, increased yield stability under drought conditions and/or increased drought tolerance in a maize plant, wherein said allele of at least one marker locus comprises, consists essentially of, or consists of: a G allele at base pair (bp) position 14762443; a C allele at base pair (bp) position 14765098; an A allele at base pair (bp) position 14765012; an A allele at base pair (bp) position 14764839; a G allele at base pair (bp) position 14764763; a C allele at base pair (bp) position 14764762; a G allele at base pair (bp) position 14764658; a G allele at base pair (bp) position 14764415; a G allele at base pair (bp) position 171748815; a C allele at base pair (bp) position 171752467; a G allele at base pair (bp) position 171752311; a C allele at base pair (bp) position 171749536; an A allele at base pair (bp) position 171749318; an A allele at base pair (bp) position 171749283; a C allele at base pair (bp) position 171749273; an A allele at base pair (bp) position 194932443; a T allele at base pair (bp) position 194935353; a C allele at base pair (bp) position 33363546; an A allele at base pair (bp) position 33368983; a T allele at base pair (bp) position 33363625; a C allele at base pair (bp) position 164854921; a G allele at base pair (bp) position 164858109; an A allele at base pair (bp) position 164855482; or any combination thereof, thereby producing a maize plant having increased yield under non-drought conditions, increased yield stability under drought conditions, and/or increased drought tolerance. In some embodiments, the alleles of the markers can be independently heterozygous or homozygous.

In representative embodiments, the detecting, in said maize plant, comprises, consists essentially of, or consists of detecting the presence of: a G or GG at base pair (bp) position 14762443; a C or CC at base pair (bp) position 14765098; an AA at base pair (bp) position 14765012; an AA at base pair (bp) position 14764839; a GG at base pair (bp) position 14764763; a CC at base pair (bp) position 14764762; a GG at base pair (bp) position 14764658; a GG at base pair (bp) position 14764415; a G or GG at base pair (bp) position 171748815; a C or CC at base pair (bp) position 171752467; a GG at base pair (bp) position 171752311; a CC at base pair (bp) position 171749536; an AA at base pair (bp) position 171749318; an AA at base pair (bp) position 171749283; a CC at base pair (bp) position 171749273; an AA at base pair (bp) position 194932443; a T or TT at base pair (bp) position 194935353; a C or CC at base pair (bp) position 33363546; an A or AA at base pair (bp) position 33368983; a TT at base pair (bp) position 33363625; a C or CC at base pair (bp) position 164854921; a G or CC at base pair (bp) position 164858109; an AA at base pair (bp) position 164855482, or any combination thereof.

In some embodiments, in the methods of producing a maize plant having increased yield under non-drought conditions, increased yield stability under drought conditions, and/or increased drought tolerance, the detecting can comprise detecting markers in a maize plant part, plant cell or plant germplasm, wherein said maize plant part, plant cell or plant germplasm in which said marker(s) is/are detected can be regenerated into a maize plant, thereby producing a maize plant having increased yield under non-drought conditions, increased yield stability under drought conditions, and/or increased drought tolerance as compared to a control maize plant.

In some embodiments, a method of selecting a maize plant or germplasm having increased yield under non-drought conditions, increased yield stability under drought conditions, and/or increased drought tolerance is provided, comprising: crossing a first maize plant or germplasm with a second maize plant or germplasm, wherein said first maize plant or germplasm comprises within its genome at least one marker associated with increased yield under non-drought conditions, increased yield stability under drought conditions, and/or increased drought tolerance in a maize plant, wherein said marker is located within a chromosomal interval comprising, consisting essentially of, or consisting of:

(a) a chromosome interval on chromosome 10 defined by and including base pair (bp) position 14762443 to base pair (bp) position 14765098; (b) a chromosome interval on chromosome 10 defined by and including base pair (bp) position 14762443 to base pair (bp) position 14765012; (c) a chromosome interval on chromosome 10 defined by and including base pair (bp) position 14762443 to base pair (bp) position 14764839; (d) a chromosome interval on chromosome 10 defined by and including base pair (bp) position 14762443 to base pair (bp) position 14764763; (e) a chromosome interval on chromosome 10 defined by and including base pair (bp) position 14762443 to base pair (bp) position 14764762; (f) a chromosome interval on chromosome 10 defined by and including base pair (bp) position 14762443 to base pair (bp) position 14764658; (g) a chromosome interval on chromosome 10 defined by and including base pair (bp) position 14762443 to base pair (bp) position 14764415; (h) a chromosome interval on chromosome 10 defined by and including base pair (bp) position 14764415 to base pair (bp) position 14765098; (i) a chromosome interval on chromosome 10 defined by and including base pair (bp) position 14764415 to base pair (bp) position 14765012; (j) a chromosome interval on chromosome 10 defined by and including base pair (bp) position 14764415 to base pair (bp) position 14764839; (k) a chromosome interval on chromosome 10 defined by and including base pair (bp) position 14764415 to base pair (bp) position 14764763; (l) a chromosome interval on chromosome 10 defined by and including base pair (bp) position 14764415 to base pair (bp) position 14764762; (m) a chromosome interval on chromosome 10 defined by and including base pair (bp) position 14764415 to base pair (bp) position 14764658; (n) a chromosome interval on chromosome 10 defined by and including base pair (bp) position 14764658 to base pair (bp) position 14765098; (o) a chromosome interval on chromosome 10 defined by and including base pair (bp) position 14764658 to base pair (bp) position 14765012; (p) a chromosome interval on chromosome 10 defined by and including base pair (bp) position 14764658 to base pair (bp) position 14764839; (q) a chromosome interval on chromosome 10 defined by and including base pair (bp) position 14764658 to base pair (bp) position 14764763; (r) a chromosome interval on chromosome 10 defined by and including base pair (bp) position 14764658 to base pair (bp) position 14764762; (s) a chromosome interval on chromosome 10 defined by and including base pair (bp) position 14764762 to base pair (bp) position 14765098; (t) a chromosome interval on chromosome 10 defined by and including base pair (bp) position 14764762 to base pair (bp) position 14765012; (u) a chromosome interval on chromosome 10 defined by and including base pair (bp) position 14764762 to base pair (bp) position 14764839; (v) a chromosome interval on chromosome 10 defined by and including base pair (bp) position 14764762 to base pair (bp) position 14764763; (w) a chromosome interval on chromosome 10 defined by and including base pair (bp) position 14764763 to base pair (bp) position 14765098; (x) a chromosome interval on chromosome 10 defined by and including base pair (bp) position 14764763 to base pair (bp) position 14765012; (y) a chromosome interval on chromosome 10 defined by and including base pair (bp) position 14764763 to base pair (bp) position 14764839; (z) a chromosome interval on chromosome 10 defined by and including base pair (bp) position 14764839 to base pair (bp) position 14765098; (aa) a chromosome interval on chromosome 10 defined by and including base pair (bp) position 14764839 to base pair (bp) position 14765012; (bb) a chromosome interval on chromosome 3 defined by and including base pair (bp) position 171748815 to base pair (bp) position 171752467; (cc) a chromosome interval on chromosome 3 defined by and including base pair (bp) position 171748815 to base pair (bp) position 171752311; (dd) a chromosome interval on chromosome 3 defined by and including base pair (bp) position 171748815 to base pair (bp) position 171749536; (ee) a chromosome interval on chromosome 3 defined by and including base pair (bp) position 171748815 to base pair (bp) position 171749318; (ff) a chromosome interval on chromosome 3 defined by and including base pair (bp) position 171748815 to base pair (bp) position 171749283; (gg) a chromosome interval on chromosome 3 defined by and including base pair (bp) position 171748815 to base pair (bp) position 171749273; (hh) a chromosome interval on chromosome 3 defined by and including base pair (bp) position 171749273 to base pair (bp) position 171752467; (ii) a chromosome interval on chromosome 3 defined by and including base pair (bp) position 171749273 to base pair (bp) position 171752311; (jj) a chromosome interval on chromosome 3 defined by and including base pair (bp) position 171749273 to base pair (bp) position 171749536; (kk) a chromosome interval on chromosome 3 defined by and including base pair (bp) position 171749273 to base pair (bp) position 171749318; (ll) a chromosome interval on chromosome 3 defined by and including base pair (bp) position 171749273 to base pair (bp) position 171749283; (mm) a chromosome interval on chromosome 3 defined by and including base pair (bp) position 171749283 to base pair (bp) position 171752467; (nn) a chromosome interval on chromosome 3 defined by and including base pair (bp) position 171749283 to base pair (bp) position 171752311; (oo) a chromosome interval on chromosome 3 defined by and including base pair (bp) position 171749283 to base pair (bp) position 171749536; (pp) a chromosome interval on chromosome 3 defined by and including base pair (bp) position 171749283 to base pair (bp) position 171749318; (qq) a chromosome interval on chromosome 3 defined by and including base pair (bp) position 171749318 to base pair (bp) position 171752467; (rr) a chromosome interval on chromosome 3 defined by and including base pair (bp) position 171749318 to base pair (bp) position 171752311; (ss) a chromosome interval on chromosome 3 defined by and including base pair (bp) position 171749318 to base pair (bp) position 171749536; (tt) a chromosome interval on chromosome 3 defined by and including base pair (bp) position 171749536 to base pair (bp) position 171752467; (uu) a chromosome interval on chromosome 3 defined by and including base pair (bp) position 171749536 to base pair (bp) position 171752311; (vv) a chromosome interval on chromosome 1 defined by and including base pair (bp) position 194932443 to base pair (bp) position 194935353; (ww) a chromosome interval on chromosome 8 defined by and including base pair (bp) position 33363546 to base pair (bp) position 33368983; (xx) a chromosome interval on chromosome 8 defined by and including base pair (bp) position 33363546 to base pair (bp) position 33363625; (yy) a chromosome interval on chromosome 8 defined by and including base pair (bp) position 33363625 to base pair (bp) position 33368983; (zz) a chromosome interval on chromosome 5 defined by and including base pair (bp) position 164854921 to base pair (bp) position 164858109; (aaa) a chromosome interval on chromosome 5 defined by and including base pair (bp) position 164854921 to base pair (bp) position 164855482; (bbb) a chromosome interval on chromosome 5 defined by and including base pair (bp) position 164855482 to base pair (bp) position 164858109; or (ccc) any combination of (a) to (bbb) above, and selecting a progeny maize plant or germplasm that comprises said at least one marker within its genome, thereby selecting a maize plant or germplasm having increased yield under non-drought conditions, increased yield stability under drought conditions, and/or increased drought tolerance.

In some embodiments, the allele at the base pair positions of said chromosome intervals comprises, consists essentially of, or consists of a G or GG at base pair (bp) position 14762443; a C or CC at base pair (bp) position 14765098; an A or AA at base pair (bp) position 14765012; an A or AA at base pair (bp) position 14764839; a G or GG at base pair (bp) position 14764763; a C or CC at base pair (bp) position 14764762; a G or GG at base pair (bp) position 14764658; a G or GG at base pair (bp) position 14764415; a G at base pair (bp) position 171748815; a C at base pair (bp) position 171752467; a G or GG at base pair (bp) position 171752311; a C or CC at base pair (bp) position 171749536; an A or AA at base pair (bp) position 171749318; an A or AA at base pair (bp) position 171749283; a C or CC at base pair (bp) position 171749273; an A or AA at base pair (bp) position 194932443; a T or TT at base pair (bp) position 194935353; a C or CC at base pair (bp) position 33363546; an A or AA at base pair (bp) position 33368983; a T or TT at base pair (bp) position 33363625; a C or CC at base pair (bp) position 164854921; a G or GG at base pair (bp) position 164858109; and/or an A or AA at base pair (bp) position 164855482. In some embodiments, the alleles defining the chromosome intervals can be independently heterozygous or homozygous.

In some embodiments, a method of selecting a maize plant or germplasm having increased yield under non-drought conditions, increased yield stability under drought conditions, and/or increased drought tolerance is provided, comprising crossing a first maize plant or germplasm with a second maize plant or germplasm, wherein said first maize plant or germplasm comprises within its genome a combination of genetic markers associated with increased yield under non-drought conditions, increased yield stability under drought conditions, and/or increased drought tolerance in a maize plant, wherein said combination of genetic markers comprises, consists essentially of or consists of: (a) a G allele at base pair (bp) position 14762443 and a C allele at base pair (bp) position 14765098; (b) a G allele at base pair (bp) position 14762443 and an A allele at base pair (bp) position 14765012; (c) a G allele at base pair (bp) position 14762443 and an A allele at base pair (bp) position 14764839; (d) a G allele at base pair (bp) position 14762443 and a G allele at base pair (bp) position 14764763; (e) a G allele at base pair (bp) position 14762443 and a C allele at base pair (bp) position 14764762; (f) a G allele at base pair (bp) position 14762443 and a G allele at base pair (bp) position 14764658; (g) a G allele at base pair (bp) position 14762443 and a G allele at base pair (bp) position 14764415; (h) a G allele at base pair (bp) position 14764415 and a C allele at base pair (bp) position 14765098; (i) a G allele at base pair (bp) position 14764415 and an A allele at base pair (bp) position 14765012; (j) a G allele at base pair (bp) position 14764415 and an A allele at base pair (bp) position 14764839; (k) a G allele at base pair (bp) position 14764415 and a G allele at base pair (bp) position 14764763; (l) a G allele at base pair (bp) position 14764415 and a C allele at base pair (bp) position 14764762; (m) a G allele at base pair (bp) position 14764415 and a G allele at base pair (bp) position 14764658; (n) a G allele at base pair (bp) position 14764658 and a C allele at base pair (bp) position 14765098; (o) a G allele at base pair (bp) position 14764658 and an A allele at base pair (bp) position 14765012; (p) a G allele at base pair (bp) position 14764658 and an A allele at base pair (bp) position 14764839; (q) a G allele at base pair (bp) position 14764658 and a G allele at base pair (bp) position 14764763; (r) a G allele at base pair (bp) position 14764658 and a C allele at base pair (bp) position 14764762; (s) a C allele at base pair (bp) position 14764762 and a C allele at base pair (bp) position 14765098; (t) a C allele at base pair (bp) position 14764762 and an A allele at base pair (bp) position 14765012; (u) a C allele at base pair (bp) position 14764762 and an A allele at base pair (bp) position 14764839; (v) a C allele at base pair (bp) position 14764762 and a G allele at base pair (bp) position 14764763; (w) a G allele at base pair (bp) position 14764763 and a C allele at base pair (bp) position 14765098; (x) a G allele at base pair (bp) position 14764763 and an A allele at base pair (bp) position 14765012; (y) a G allele at base pair (bp) position 14764763 and an A allele at base pair (bp) position 14764839; (z) an A allele at base pair (bp) position 14764839 and a C allele at base pair (bp) position 14765098; (aa) an A allele at base pair (bp) position 14764839 and an A allele at base pair (bp) position 14765012; (bb) a G allele at base pair (bp) position 171748815 and a C allele at base pair (bp) position 171752467; (cc) a G allele at base pair (bp) position 171748815 and a G allele at base pair (bp) position 171752311; (dd) a G allele at base pair (bp) position 171748815 and a C allele at base pair (bp) position 171749536; (ee) a G allele at base pair (bp) position 171748815 and an A allele at base pair (bp) position 171749318; (ff) a G allele at base pair (bp) position 171748815 and an A allele at base pair (bp) position 171749283; (gg) a G allele at base pair (bp) position 171748815 and a C allele at base pair (bp) position 171749273; (hh) a C allele at base pair (bp) position 171749273 and a C allele at base pair (bp) position 171752467; (ii) a C allele at base pair (bp) position 171749273 and a G allele at base pair (bp) position 171752311; (jj) a C allele at base pair (bp) position 171749273 and a C allele at base pair (bp) position 171749536; (kk) a C allele at base pair (bp) position 171749273 and an A allele at base pair (bp) position 171749318; (ll) a C allele at base pair (bp) position 171749273 and an A allele at base pair (bp) position 171749283; (mm) an A allele at base pair (bp) position 171749283 and a C allele at base pair (bp) position 171752467; (nn) an A allele at base pair (bp) position 171749283 a G allele at base pair (bp) position 171752311; (oo) an A allele at base pair (bp) position 171749283 and a C allele at base pair (bp) position 171749536; (pp) an A allele at base pair (bp) position 171749283 and an A allele at base pair (bp) position 171749318; (qq) an A allele at base pair (bp) position 171749318 and a C allele at base pair (bp) position 171752467; (rr) an A allele at base pair (bp) position 171749318 and a G allele at base pair (bp) position 171752311; (ss) an A allele at base pair (bp) position 171749318 and a C allele at base pair (bp) position 171749536; (tt) a C allele at base pair (bp) position 171749536 and a C allele at base pair (bp) position 171752467; (uu) a C allele at base pair (bp) position 171749536 and a G allele at base pair (bp) position 171752311; (vv) an A allele at base pair (bp) position 194932443 and a T allele at base pair (bp) position 194935353; (ww) a C allele at base pair (bp) position 33363546 and an A allele at base pair (bp) position 33368983; (xx) a C allele at base pair (bp) position 33363546 and a T allele at base pair (bp) position 33363625; (yy) a T allele at base pair (bp) position 33363625 and an A allele at base pair (bp) position 33368983; (zz) a C allele at base pair (bp) position 164854921 and a G allele at base pair (bp) position 164858109; (aaa) a C allele at base pair (bp) position 164854921 and an A allele at base pair (bp) position 164855482; (bbb) an A allele at base pair (bp) position 164855482 and a G allele at base pair (bp) position 164858109; or (ccc) any combination of (a) to (bbb) above; and selecting a progeny maize plant or germplasm that comprises said marker within its genome, thereby selecting a maize plant or germplasm having increased yield under non-drought conditions, increased yield stability under drought conditions, and/or increased drought tolerance. In some embodiments, the alleles at the base pair positions defined herein can be independently heterozygous or homozygous.

In some embodiments, a method of selecting a maize plant or germplasm having increased yield under non-drought conditions, increased yield stability under drought conditions, and/or increased drought tolerance is provided, comprising: crossing a first maize plant or germplasm with a second maize plant or germplasm, wherein said first maize plant or germplasm comprises within its genome a genetic marker associated with increased yield under non-drought conditions, increased yield stability under drought conditions, and/or increased drought tolerance in a maize plant, wherein said genetic marker comprises, consists essentially of, or consists of a G or GG at base pair (bp) position 14762443; a C or CC at base pair (bp) position 14765098; an A or AA at base pair (bp) position 14765012; an A or AA at base pair (bp) position 14764839; a G or GG at base pair (bp) position 14764763; a C or CC at base pair (bp) position 14764762; a G or GG at base pair (bp) position 14764658; a G or GG at base pair (bp) position 14764415; a G at base pair (bp) position 171748815; a C at base pair (bp) position 171752467; a G or GG at base pair (bp) position 171752311; a C or CC at base pair (bp) position 171749536; an A or AA at base pair (bp) position 171749318; an A or AA at base pair (bp) position 171749283; a C or CC at base pair (bp) position 171749273; an A or AA at base pair (bp) position 194932443; a T or TT at base pair (bp) position 194935353; a C or CC at base pair (bp) position 33363546; an A or AA at base pair (bp) position 33368983; a T or TT at base pair (bp) position 33363625; a C or CC at base pair (bp) position 164854921; a G or GG at base pair (bp) position 164858109; an A or AA at base pair (bp) position 164855482; and/or any combination thereof; and selecting a progeny maize plant or germplasm that comprises said marker within its genome, thereby selecting a maize plant or germplasm having increased yield under non-drought conditions, increased yield stability under drought conditions, and/or increased drought tolerance. In some embodiments, the alleles at the base pair positions as defined herein can be independently heterozygous or homozygous.

In representative embodiments, said genetic marker comprises, consists essentially of, or consists of a G or GG at base pair (bp) position 14762443; a C or CC at base pair (bp) position 14765098; an AA at base pair (bp) position 14765012; an AA at base pair (bp) position 14764839; a GG at base pair (bp) position 14764763; a CC at base pair (bp) position 14764762; a GG at base pair (bp) position 14764658; a GG at base pair (bp) position 14764415; a G or GG at base pair (bp) position 171748815; a C or CC at base pair (bp) position 171752467; a G at base pair (bp) position 171752311; a CC at base pair (bp) position 171749536; an AA at base pair (bp) position 171749318; an AA at base pair (bp) position 171749283; a CC at base pair (bp) position 171749273; an AA at base pair (bp) position 194932443; a T or TT at base pair (bp) position 194935353; a C or CC at base pair (bp) position 33363546; an A or AA at base pair (bp) position 33368983; a TT at base pair (bp) position 33363625; a C or CC at base pair (bp) position 164854921; a G or CC at base pair (bp) position 164858109; an AA at base pair (bp) position 164855482; or any combination thereof.

In some embodiments, the second maize plant or germplasm of this invention is of an elite variety of maize. In some embodiments, the genome of the second maize plant or germplasm is at least about 60%, 65%, 70%, 75%, 80%, 85%, 90%, 95%, 97%, 99% or 100% identical to that of an elite variety of maize.

In some embodiments of this invention, a method of introgressing a genetic marker associated with increased yield under non-drought conditions, increased yield stability under drought conditions, and/or increased drought tolerance in maize into a genetic background lacking said marker is provided, the method comprising: crossing a donor comprising said marker with a recurrent parent that lacks said marker; and backcrossing progeny comprising said marker with the recurrent parent, wherein said progeny are identified by detecting in their genome the presence of a marker associated with increased yield under non-drought conditions, increased yield stability under drought conditions, and/or increased drought tolerance in a maize plant, wherein said marker is located within (a) a chromosome interval on chromosome 10 defined by and including base pair (bp) position 14762443 to base pair (bp) position 14765098; (b) a chromosome interval on chromosome 10 defined by and including base pair (bp) position 14762443 to base pair (bp) position 14765012; (c) a chromosome interval on chromosome 10 defined by and including base pair (bp) position 14762443 to base pair (bp) position 14764839; (d) a chromosome interval on chromosome 10 defined by and including base pair (bp) position 14762443 to base pair (bp) position 14764763; (e) a chromosome interval on chromosome 10 defined by and including base pair (bp) position 14762443 to base pair (bp) position 14764762; (f) a chromosome interval on chromosome 10 defined by and including base pair (bp) position 14762443 to base pair (bp) position 14764658; (g) a chromosome interval on chromosome 10 defined by and including base pair (bp) position 14762443 to base pair (bp) position 14764415; (h) a chromosome interval on chromosome 10 defined by and including base pair (bp) position 14764415 to base pair (bp) position 14765098; (i) a chromosome interval on chromosome 10 defined by and including base pair (bp) position 14764415 to base pair (bp) position 14765012; (j) a chromosome interval on chromosome 10 defined by and including base pair (bp) position 14764415 to base pair (bp) position 14764839; (k) a chromosome interval on chromosome 10 defined by and including base pair (bp) position 14764415 to base pair (bp) position 14764763; (l) a chromosome interval on chromosome 10 defined by and including base pair (bp) position 14764415 to base pair (bp) position 14764762; (m) a chromosome interval on chromosome 10 defined by and including base pair (bp) position 14764415 to base pair (bp) position 14764658; (n) a chromosome interval on chromosome 10 defined by and including base pair (bp) position 14764658 to base pair (bp) position 14765098; (o) a chromosome interval on chromosome 10 defined by and including base pair (bp) position 14764658 to base pair (bp) position 14765012; (p) a chromosome interval on chromosome 10 defined by and including base pair (bp) position 14764658 to base pair (bp) position 14764839; (q) a chromosome interval on chromosome 10 defined by and including base pair (bp) position 14764658 to base pair (bp) position 14764763; (r) a chromosome interval on chromosome 10 defined by and including base pair (bp) position 14764658 to base pair (bp) position 14764762; (s) a chromosome interval on chromosome 10 defined by and including base pair (bp) position 14764762 to base pair (bp) position 14765098; (t) a chromosome interval on chromosome 10 defined by and including base pair (bp) position 14764762 to base pair (bp) position 14765012; (u) a chromosome interval on chromosome 10 defined by and including base pair (bp) position 14764762 to base pair (bp) position 14764839; (v) a chromosome interval on chromosome 10 defined by and including base pair (bp) position 14764762 to base pair (bp) position 14764763; (w) a chromosome interval on chromosome 10 defined by and including base pair (bp) position 14764763 to base pair (bp) position 14765098; (x) a chromosome interval on chromosome 10 defined by and including base pair (bp) position 14764763 to base pair (bp) position 14765012; (y) a chromosome interval on chromosome 10 defined by and including base pair (bp) position 14764763 to base pair (bp) position 14764839; (z) a chromosome interval on chromosome 10 defined by and including base pair (bp) position 14764839 to base pair (bp) position 14765098; (aa) a chromosome interval on chromosome 10 defined by and including base pair (bp) position 14764839 to base pair (bp) position 14765012; (bb) a chromosome interval on chromosome 3 defined by and including base pair (bp) position 171748815 to base pair (bp) position 171752467; (cc) a chromosome interval on chromosome 3 defined by and including base pair (bp) position 171748815 to base pair (bp) position 171752311; (dd) a chromosome interval on chromosome 3 defined by and including base pair (bp) position 171748815 to base pair (bp) position 171749536; (ee) a chromosome interval on chromosome 3 defined by and including base pair (bp) position 171748815 to base pair (bp) position 171749318; (ff) a chromosome interval on chromosome 3 defined by and including base pair (bp) position 171748815 to base pair (bp) position 171749283; (gg) a chromosome interval on chromosome 3 defined by and including base pair (bp) position 171748815 to base pair (bp) position 171749273; (hh) a chromosome interval on chromosome 3 defined by and including base pair (bp) position 171749273 to base pair (bp) position 171752467; (ii) a chromosome interval on chromosome 3 defined by and including base pair (bp) position 171749273 to base pair (bp) position 171752311; (jj) a chromosome interval on chromosome 3 defined by and including base pair (bp) position 171749273 to base pair (bp) position 171749536; (kk) a chromosome interval on chromosome 3 defined by and including base pair (bp) position 171749273 to base pair (bp) position 171749318; (ll) a chromosome interval on chromosome 3 defined by and including base pair (bp) position 171749273 to base pair (bp) position 171749283; (mm) a chromosome interval on chromosome 3 defined by and including base pair (bp) position 171749283 to base pair (bp) position 171752467; (nn) a chromosome interval on chromosome 3 defined by and including base pair (bp) position 171749283 to base pair (bp) position 171752311; (oo) a chromosome interval on chromosome 3 defined by and including base pair (bp) position 171749283 to base pair (bp) position 171749536; (pp) a chromosome interval on chromosome 3 defined by and including base pair (bp) position 171749283 to base pair (bp) position 171749318; (qq) a chromosome interval on chromosome 3 defined by and including base pair (bp) position 171749318 to base pair (bp) position 171752467; (rr) a chromosome interval on chromosome 3 defined by and including base pair (bp) position 171749318 to base pair (bp) position 171752311; (ss) a chromosome interval on chromosome 3 defined by and including base pair (bp) position 171749318 to base pair (bp) position 171749536; (tt) a chromosome interval on chromosome 3 defined by and including base pair (bp) position 171749536 to base pair (bp) position 171752467; (uu) a chromosome interval on chromosome 3 defined by and including base pair (bp) position 171749536 to base pair (bp) position 171752311; (vv) a chromosome interval on chromosome 1 defined by and including base pair (bp) position 194932443 to base pair (bp) position 194935353; (ww) a chromosome interval on chromosome 8 defined by and including base pair (bp) position 33363546 to base pair (bp) position 33368983; (xx) a chromosome interval on chromosome 8 defined by and including base pair (bp) position 33363546 to base pair (bp) position 33363625; (yy) a chromosome interval on chromosome 8 defined by and including base pair (bp) position 33363625 to base pair (bp) position 33368983; (zz) a chromosome interval on chromosome 5 defined by and including base pair (bp) position 164854921 to base pair (bp) position 164858109; (aaa) a chromosome interval on chromosome 5 defined by and including base pair (bp) position 164854921 to base pair (bp) position 164855482; (bbb) a chromosome interval on chromosome 5 defined by and including base pair (bp) position 164855482 to base pair (bp) position 164858109; or (ccc) any combination of (a) to (bbb) above; and producing a maize plant or germplasm having increased yield under non-drought conditions, increased yield stability under drought conditions, and/or increased drought tolerance and comprising said genetic marker associated with increased yield under non-drought conditions, increased yield stability under drought conditions, and/or increased drought tolerance in the genetic background of the recurrent parent, thereby introgressing the genetic marker associated with increased yield under non-drought conditions, increased yield stability under drought conditions, and/or increased drought tolerance into a genetic background lacking said marker. In some embodiments, the base pair positions defining the chromosomal intervals can comprise alleles, which can be heterozygous or homozygous, or any combination thereof.

In some embodiments of this invention, a method of introgressing a genetic marker associated with increased yield under non-drought conditions, increased yield stability under drought conditions, and/or increased drought tolerance in maize into a genetic background lacking said marker is provided, the method comprising: crossing a donor comprising said marker with a recurrent parent that lacks said marker; and backcrossing progeny comprising said marker with the recurrent parent, wherein said progeny are identified by detecting in their genome the presence of a marker associated with increased yield under non-drought conditions, increased yield stability under drought conditions, and/or increased drought tolerance in a maize plant, wherein said marker comprises, consists essentially of, or consists of a G or GG at base pair (bp) position 14762443; a C or CC at base pair (bp) position 14765098; an A or AA at base pair (bp) position 14765012; an A or AA at base pair (bp) position 14764839; a G or GG at base pair (bp) position 14764763; a C or CC at base pair (bp) position 14764762; a G or GG at base pair (bp) position 14764658; a G or GG at base pair (bp) position 14764415; a G at base pair (bp) position 171748815; a C at base pair (bp) position 171752467; a G or GG at base pair (bp) position 171752311; a C or CC at base pair (bp) position 171749536; an A or AA at base pair (bp) position 171749318; an A or AA at base pair (bp) position 171749283; a C or CC at base pair (bp) position 171749273; an A or AA at base pair (bp) position 194932443; a T or TT at base pair (bp) position 194935353; a C or CC at base pair (bp) position 33363546; an A or AA at base pair (bp) position 33368983; a T or TT at base pair (bp) position 33363625; a C or CC at base pair (bp) position 164854921; a G or GG at base pair (bp) position 164858109; an A or AA at base pair (bp) position 164855482; or any combination thereof; and selecting a progeny maize plant or germplasm that comprises said marker within its genome, thereby selecting a maize plant or germplasm having increased yield under non-drought conditions, increased yield stability under drought conditions, and/or increased drought tolerance. In some embodiments, the alleles at the base pair positions as defined herein can be independently heterozygous or homozygous.

The present invention provides maize plants and germplasms having increased yield under non-drought conditions, increased yield stability under drought conditions, and/or increased drought tolerance as compared to a control. As discussed above, the methods of the present invention can be utilized to identify, produce and/or select a maize plant or germplasm having increased yield under non-drought conditions, increased yield stability under drought conditions, and/or increased drought tolerance. In addition to the methods described above, a maize plant or germplasm having increased yield under non-drought conditions, increased yield stability under drought conditions, and/or increased drought tolerance may be produced by any method whereby a marker associated with increased yield under non-drought conditions, increased yield stability under drought conditions, and/or increased drought tolerance in a maize plant is introduced into the maize plant or germplasm. Such methods include, but are not limited to, transformation (including, but not limited to, bacterial-mediated nucleic acid delivery (e.g., via Agrobacteria)), viral-mediated nucleic acid delivery, silicon carbide or nucleic acid whisker-mediated nucleic acid delivery, liposome mediated nucleic acid delivery, microinjection, microparticle bombardment, electroporation, sonication, infiltration, PEG-mediated nucleic acid uptake, as well as any other electrical, chemical, physical (mechanical) and/or biological mechanism that results in the introduction of nucleic acid into the plant cell, or any combination thereof, protoplast transformation or fusion, a double haploid technique, embryo rescue, or by any other nucleic acid transfer system.

"Introducing" in the context of a plant cell, plant and/or plant part means contacting a nucleic acid molecule with the plant, plant part, and/or plant cell in such a manner that the nucleic acid molecule gains access to the interior of the plant cell and/or a cell of the plant and/or plant part. Where more than one nucleic acid molecule is to be introduced, these nucleic acid molecules can be assembled as part of a single polynucleotide or nucleic acid construct, or as separate polynucleotide or nucleic acid constructs, and can be located on the same or different nucleic acid constructs. Accordingly, these polynucleotides can be introduced into plant cells in a single transformation event, in separate transformation events, or, e.g., as part of a breeding protocol. Thus, the term "transformation" as used herein refers to the introduction of a heterologous nucleic acid into a cell.

Thus, a maize plant or maize plant part having a genetic marker associated with increased yield under non-drought conditions, increased yield stability under drought conditions, and/or increased drought tolerance, obtainable by the methods of the presently disclosed subject matter, are aspects of the presently disclosed subject matter. The maize plant, or maize plant parts, or maize germplasm of this invention having at least one genetic marker associated with increased yield under non-drought conditions, increased yield stability under drought conditions, and/or increased drought tolerance can be heterozygous or homozygous for the genetic marker.

In some embodiments, the maize plant or germplasm may be the progeny of a cross between an elite maize variety and a variety of maize that comprises an allele associated with increased yield under non-drought conditions, increased yield stability under drought conditions, and/or increased drought tolerance. In some embodiments, the maize plant or germplasm is at least about 60%, 65%, 70%, 75%, 80%, 85%, 90%, 95%, 97%, 99% or 100% identical to that of an elite variety of maize.

The maize plant or germplasm may be the progeny of an introgression wherein the recurrent parent is an elite variety of maize and the donor comprises a genetic marker associated (e.g., SNP, combination of SNPs, SNP located in a chromosome interval) with increased yield under non-drought conditions, increased yield stability under drought conditions, and/or increased drought tolerance in a maize plant as described herein.

The maize plant or germplasm may be the progeny of a cross between a first elite variety of maize (e.g., a tester line) and the progeny of a cross between a second elite variety of maize (e.g., a recurrent parent) and a variety of maize that comprises a genetic marker associated with increased yield under non-drought conditions, increased yield stability under drought conditions, and/or increased drought tolerance in a maize plant as described herein (e.g., a donor).

Another aspect of the presently disclosed subject matter relates to a method of producing seeds that can be grown into maize plants comprising increased yield under non-drought conditions, increased yield stability under drought conditions, and/or increased drought tolerance. In some embodiments, the method comprises providing a maize plant of this invention having increased yield under non-drought conditions, increased yield stability under drought conditions, and/or increased drought tolerance, crossing said maize plant with another maize plant, and collecting seeds resulting from the cross, which when planted, produce maize plants having increased yield under non-drought conditions, increased yield stability under drought conditions, and/or increased drought tolerance as compared to a control (e.g., the "another maize plant").

Accordingly, the present invention provides improved maize plants, seeds, and/or maize tissue culture produced by the methods described herein.

In some embodiments, the presently disclosed subject matter provides methods for analyzing the genomes of maize plants/germplasms to identify those that include desired markers associated with increased yield under non-drought conditions, increased yield stability under drought conditions, and/or increased drought tolerance. In some embodiments, the methods of analysis comprise amplifying subsequences of the genomes of the maize plants/germplasms and determining the nucleotides present in one, some, or all positions of the amplified subsequences.

Additional aspects of the invention include a harvested product produced from the plants and/or parts thereof of the invention, as well as a post-harvest product produced from said harvested product. A harvested product can be a whole plant or any plant part, as described herein, wherein said harvested product comprises a recombinant nucleic acid molecule/nucleotide sequence of the invention. Thus, in some embodiments, non-limiting examples of a harvested product include a seed, a fruit, a flower or part thereof (e.g., an anther, a stigma, and the like), a leaf, a stem, and the like. In other embodiments, a post-harvested product includes, but is not limited to, a flour, meal, oil, starch, cereal, and the like produced from a harvested seed of the invention, wherein said seed comprises in its genome a recombinant nucleic acid molecule/nucleotide sequence of the invention.

In some embodiments, the invention further provides a maize crop comprising a plurality of maize plants of the invention planted together in, for example, an agricultural field, a golf course, a residential lawn, a road side, an athletic field, and/or a recreational field.

In some embodiments, a method of improving the yield of a maize crop when said maize crop is exposed to drought conditions is provided, the method comprising cultivating a plurality of plants of the invention as the plant crop, wherein the plurality of plants of said maize crop have increased yield under non-drought conditions, increased yield stability under drought conditions, and/or increased drought tolerance, thereby improving the yield of said maize crop as compared to a control maize crop, wherein the control plant crop is produced from a plurality of maize plants lacking said genetic marker grown under the same environmental conditions.

The following examples are included to demonstrate various embodiments of the invention and are not intended to be a detailed catalog of all the different ways in which the present invention may be implemented or of all the features that may be added to the present invention. Persons skilled in the art will appreciate that numerous variations and additions to the various embodiments may be made without departing from the present invention. Hence, the following descriptions are intended to illustrate some particular embodiments of the invention, and not to exhaustively specify all permutations, combinations and variations thereof.

EXAMPLES

Example 1. Identification of Markers Associated with Increased Yield Under Non-Drought Conditions, Increased Yield Stability Under Drought Conditions, and/or Increased Drought Tolerance Several genome-wide association studies (GWAS) were performed to identify markers associated with three yield traits (yield under irrigation, yield under drought stress and the difference between them) using diverse inbred and hybrid panels of maize. The inbred panel consisted of 262,224 genic SNPs across 478 inbred lines. The hybrid panel was split between the two heterotic groups (294 non-stiff stalk lines crossed to a single tester and 210 stiff stalk lines crossed to a different single tester) and between two years. The first year (2008) consisted primarily of locations used for flowering-time drought stress and the second year (2009) consisted primarily of locations used for season-long drought stress. The non-stiff stalk panels consisted of approximately 230,000 SNPs and the stiff stalk panels consisted of approximately 150,000 SNPs. At least 4 lines contained the minor allele (less common allele) in the case of all the SNPs.

Best linear unbiased predictors (BLUPs) were calculated for yield under irrigation and yield under drought stress for each line in each panel according to the model: Trait=Line+Trial+Line×Trial+error. The BLUPs for yield under irrigation and yield under drought stress were then standardized and these values were used to calculate the difference between the two traits (standardized yield under irrigation−standardized yield under drought stress). Associations were conducted using the model: y=Pv+Sa+Iu+e. Where y is a vector of phenotypic values (BLUPs), v is a vector of fixed effects regarding population structure, a is the fixed effect for the candidate marker, u is a vector of the random effects pertaining to recent co-ancestry, and e is a vector of residuals. P is a matrix of principal component (PC) vectors defining population structure, S is the vector of genotypes at the candidate marker, and I is an identity matrix. The variances of the random effects are assumed to be $Var(u)=2KV_g$ and $Var(e)=IV_R$, where K is the kinship matrix consisting of the proportion of shared allele values.

All markers were extracted that fell within a set of 23 putative SWEET genes from maize in order to take a candidate gene-based approach for identifying potential associations. This resulted in 113 markers examined for yield under irrigation and yield under drought stress in the five testing panels described above (results attached below in Tables 2.1-2.4). In some cases a particular marker may not have been tested in a specific panel due to too few lines with the minor genotype which varied from panel to panel. A QQ-Plot was generated to look at the observed distribution of −log 10(P-values) (FIG. 1). Based on the QQ-Plot a −log 10(P-value) threshold of 2 was used to select marker-trait associations (MTAs) to be used to help prioritize construct leads. Those markers showing a significant association are provided in Table 1.

TABLE 2.1

Data for the 113 markers examined for yield under irrigation and yield under drought stress in the five testing panels described in Example 1.

| SNP | GeneModelID | Description | Chr | Gene begin | Gene end |
|---|---|---|---|---|---|
| 1 | GRMZM2G173669 | SWEET-13a | chr10 | 14762443 | 14765098 |
| 2 | GRMZM2G039365 | SWEET-1a | chr3 | 171748815 | 171752467 |
| 3 | GRMZM2G039365 | SWEET-1a | chr3 | 171748815 | 171752467 |
| 4 | GRMZM2G368827 | SWEET-11/MtN3 | chr1 | 194932443 | 194935353 |
| 5 | GRMZM2G039365 | SWEET-1a | chr3 | 171748815 | 171752467 |
| 6 | GRMZM2G039365 | SWEET-1a | chr3 | 171748815 | 171752467 |
| 7 | GRMZM2G039365 | SWEET-1a | chr3 | 171748815 | 171752467 |
| 8 | GRMZM2G173669 | SWEET-13a | chr10 | 14762443 | 14765098 |
| 9 | GRMZM2G173669 | SWEET-13a | chr10 | 14762443 | 14765098 |
| 10 | GRMZM2G111926 | SWEET-16b | chr8 | 33363546 | 33368983 |
| 11 | GRMZM2G173669 | SWEET-13a | chr10 | 14762443 | 14765098 |
| 12 | GRMZM5G872392 | SWEET-15b | chr5 | 164854921 | 164858109 |

TABLE 2.1-continued

Data for the 113 markers examined for yield under irrigation and yield under drought stress in the five testing panels described in Example 1.

| SNP | GeneModelID | Description | Chr | Gene begin | Gene end |
|---|---|---|---|---|---|
| 13 | GRMZM2G173669 | SWEET-13a | chr10 | 14762443 | 14765098 |
| 14 | GRMZM2G173669 | SWEET-13a | chr10 | 14762443 | 14765098 |
| 15 | GRMZM2G173669 | SWEET-13a | chr10 | 14762443 | 14765098 |
| 16 | GRMZM2G173669 | SWEET-13a | chr10 | 14762443 | 14765098 |
| 17 | GRMZM2G173669 | SWEET-13a | chr10 | 14762443 | 14765098 |
| 18 | GRMZM2G173669 | SWEET-13a | chr10 | 14762443 | 14765098 |
| 19 | GRMZM2G173669 | SWEET-13a | chr10 | 14762443 | 14765098 |
| 20 | GRMZM2G039365 | SWEET-1a | chr3 | 171748815 | 171752467 |
| 21 | GRMZM2G000812 | Sweet-4a | chr5 | 126816126 | 126819003 |
| 22 | GRMZM2G000812 | Sweet-4a | chr5 | 126816126 | 126819003 |
| 23 | GRMZM2G144581 | Sweet-4b | chr5 | 127602043 | 127605592 |
| 24 | GRMZM2G144581 | Sweet-4b | chr5 | 127602043 | 127605592 |
| 25 | GRMZM2G173669 | SWEET-13a | chr10 | 14762443 | 14765098 |
| 26 | GRMZM2G153358 | SWEET-1b | chr6 | 147913391 | 147916344 |
| 27 | GRMZM2G179349 | SWEET-13c | chr3 | 108706693 | 108708062 |
| 28 | GRMZM5G872392 | SWEET-15b | chr5 | 164854921 | 164858109 |
| 29 | GRMZM2G111926 | SWEET-16b | chr8 | 33363546 | 33368983 |
| 30 | GRMZM2G111926 | SWEET-16b | chr8 | 33363546 | 33368983 |
| 31 | GRMZM2G173669 | SWEET-13a | chr10 | 14762443 | 14765098 |
| 32 | GRMZM2G039365 | SWEET-1a | chr3 | 171748815 | 171752467 |
| 33 | GRMZM5G872392 | SWEET-15b | chr5 | 164854921 | 164858109 |
| 34 | GRMZM2G106462 | SWEET-16a | chr3 | 56812209 | 56820107 |
| 35 | GRMZM2G039365 | SWEET-1a | chr3 | 171748815 | 171752467 |
| 36 | GRMZM2G021706 | SWEET-13b | chr10 | 14642867 | 14645735 |
| 37 | GRMZM2G021706 | SWEET-13b | chr10 | 14642867 | 14645735 |
| 38 | GRMZM2G039365 | SWEET-1a | chr3 | 171748815 | 171752467 |
| 39 | GRMZM2G039365 | SWEET-1a | chr3 | 171748815 | 171752467 |
| 40 | GRMZM2G039365 | SWEET-1a | chr3 | 171748815 | 171752467 |
| 41 | GRMZM2G368827 | SWEET-11/MtN3 | chr1 | 194932443 | 194935353 |
| 42 | GRMZM2G173669 | SWEET-13a | chr10 | 14762443 | 14765098 |
| 43 | GRMZM2G173669 | SWEET-13a | chr10 | 14762443 | 14765098 |
| 44 | GRMZM2G173669 | SWEET-13a | chr10 | 14762443 | 14765098 |
| 45 | GRMZM2G039365 | SWEET-1a | chr3 | 171748815 | 171752467 |
| 46 | GRMZM2G106462 | SWEET-16a | chr3 | 56812209 | 56820107 |
| 47 | GRMZM2G021706 | SWEET-13b | chr10 | 14642867 | 14645735 |
| 48 | GRMZM2G021706 | SWEET-13b | chr10 | 14642867 | 14645735 |
| 49 | GRMZM2G039365 | SWEET-1a | chr3 | 171748815 | 171752467 |
| 50 | GRMZM2G153358 | SWEET-1b | chr6 | 147913391 | 147916344 |
| 51 | GRMZM5G872392 | SWEET-15b | chr5 | 164854921 | 164858109 |
| 52 | GRMZM2G111926 | SWEET-16b | chr8 | 33363546 | 33368983 |
| 53 | GRMZM2G153358 | SWEET-1b | chr6 | 147913391 | 147916344 |
| 54 | GRMZM2G039365 | SWEET-1a | chr3 | 171748815 | 171752467 |
| 55 | GRMZM2G173669 | SWEET-13a | chr10 | 14762443 | 14765098 |
| 56 | GRMZM2G111926 | SWEET-16b | chr8 | 33363546 | 33368983 |
| 57 | GRMZM2G039365 | SWEET-1a | chr3 | 171748815 | 171752467 |
| 58 | GRMZM2G000812 | Sweet-4a | chr5 | 126816126 | 126819003 |
| 59 | GRMZM2G153358 | SWEET-1b | chr6 | 147913391 | 147916344 |
| 60 | GRMZM2G111926 | SWEET-16b | chr8 | 33363546 | 33368983 |
| 61 | GRMZM5G872392 | SWEET-15b | chr5 | 164854921 | 164858109 |
| 62 | GRMZM2G021706 | SWEET-13b | chr10 | 14642867 | 14645735 |
| 63 | GRMZM2G173669 | SWEET-13a | chr10 | 14762443 | 14765098 |
| 64 | GRMZM2G173669 | SWEET-13a | chr10 | 14762443 | 14765098 |
| 65 | GRMZM2G144581 | Sweet-4b | chr5 | 127602043 | 127605592 |
| 66 | GRMZM2G144581 | Sweet-4b | chr5 | 127602043 | 127605592 |
| 67 | GRMZM2G153358 | SWEET-1b | chr6 | 147913391 | 147916344 |
| 68 | GRMZM2G173669 | SWEET-13a | chr10 | 14762443 | 14765098 |
| 69 | GRMZM2G173669 | SWEET-13a | chr10 | 14762443 | 14765098 |
| 70 | GRMZM2G368827 | SWEET-11/MtN3 | chr1 | 194932443 | 194935353 |
| 71 | GRMZM2G000812 | Sweet-4a | chr5 | 126816126 | 126819003 |
| 72 | GRMZM2G000812 | Sweet-4a | chr5 | 126816126 | 126819003 |
| 73 | GRMZM2G144581 | Sweet-4b | chr5 | 127602043 | 127605592 |
| 74 | GRMZM2G144581 | Sweet-4b | chr5 | 127602043 | 127605592 |
| 75 | GRMZM2G153358 | SWEET-1b | chr6 | 147913391 | 147916344 |
| 76 | GRMZM2G153358 | SWEET-1b | chr6 | 147913391 | 147916344 |
| 77 | GRMZM5G872392 | SWEET-15b | chr5 | 164854921 | 164858109 |
| 78 | GRMZM2G039365 | SWEET-1a | chr3 | 171748815 | 171752467 |
| 79 | GRMZM2G039365 | SWEET-1a | chr3 | 171748815 | 171752467 |
| 80 | GRMZM5G872392 | SWEET-15b | chr5 | 164854921 | 164858109 |
| 81 | GRMZM5G872392 | SWEET-15b | chr5 | 164854921 | 164858109 |
| 82 | GRMZM2G039365 | SWEET-1a | chr3 | 171748815 | 171752467 |
| 83 | GRMZM2G039365 | SWEET-1a | chr3 | 171748815 | 171752467 |
| 84 | GRMZM2G021706 | SWEET-13b | chr10 | 14642867 | 14645735 |
| 85 | GRMZM2G021706 | SWEET-13b | chr10 | 14642867 | 14645735 |
| 86 | GRMZM2G179679 | SWEET-3a | chr8 | 112530662 | 112532375 |
| 87 | GRMZM2G000812 | Sweet-4a | chr5 | 126816126 | 126819003 |

TABLE 2.1-continued

Data for the 113 markers examined for yield under irrigation and yield under drought stress in the five testing panels described in Example 1.

| SNP | GeneModelID | Description | Chr | Gene begin | Gene end |
|---|---|---|---|---|---|
| 88 | GRMZM2G153358 | SWEET-1b | chr6 | 147913391 | 147916344 |
| 89 | GRMZM2G153358 | SWEET-1b | chr6 | 147913391 | 147916344 |
| 90 | GRMZM2G368827 | SWEET-11/MtN3 | chr1 | 194932443 | 194935353 |
| 91 | GRMZM2G021706 | SWEET-13b | chr10 | 14642867 | 14645735 |
| 92 | GRMZM2G039365 | SWEET-1a | chr3 | 171748815 | 171752467 |
| 93 | GRMZM2G039365 | SWEET-1a | chr3 | 171748815 | 171752467 |
| 94 | GRMZM2G153358 | SWEET-1b | chr6 | 147913391 | 147916344 |
| 95 | GRMZM2G021706 | SWEET-13b | chr10 | 14642867 | 14645735 |
| 96 | GRMZM2G168365 | SWEET-15a | chr4 | 96310951 | 96312854 |
| 97 | GRMZM5G872392 | SWEET-15b | chr5 | 164854921 | 164858109 |
| 98 | GRMZM2G021706 | SWEET-13b | chr10 | 14642867 | 14645735 |
| 99 | GRMZM2G368827 | SWEET-11/MtN3 | chr1 | 194932443 | 194935353 |
| 100 | GRMZM2G021706 | SWEET-13b | chr10 | 14642867 | 14645735 |
| 101 | GRMZM2G106462 | SWEET-16a | chr3 | 56812209 | 56820107 |
| 102 | GRMZM2G173669 | SWEET-13a | chr10 | 14762443 | 14765098 |
| 103 | GRMZM2G173669 | SWEET-13a | chr10 | 14762443 | 14765098 |
| 104 | GRMZM2G144581 | Sweet-4b | chr5 | 127602043 | 127605592 |
| 105 | GRMZM2G173669 | SWEET-13a | chr10 | 14762443 | 14765098 |
| 106 | GRMZM2G368827 | SWEET-11/MtN3 | chr1 | 194932443 | 194935353 |
| 107 | GRMZM2G039365 | SWEET-1a | chr3 | 171748815 | 171752467 |
| 108 | GRMZM2G021706 | SWEET-13b | chr10 | 14642867 | 14645735 |
| 109 | GRMZM2G153358 | SWEET-1b | chr6 | 147913391 | 147916344 |
| 110 | GRMZM2G173669 | SWEET-13a | chr10 | 14762443 | 14765098 |
| 111 | GRMZM2G021706 | SWEET-13b | chr10 | 14642867 | 14645735 |
| 112 | GRMZM2G368827 | SWEET-11/MtN3 | chr1 | 194932443 | 194935353 |
| 113 | GRMZM2G106462 | SWEET-16a | chr3 | 56812209 | 56820107 |

TABLE 2.2

Data for the 113 markers examined for yield under irrigation and yield under drought stress in the five testing panels described in Example 1, continued.

| SNP | Marker | Site | hyb_irr_nss_2008_NegLogP | hyb_irr_nss_2009_NegLogP |
|---|---|---|---|---|
| 1 | PZE1014822710 | 14764762 | 2.48339402 | 1.93998254 |
| 2 | PZE03170079889 | 171752311 | 0.80951454 | 3.08080659 |
| 3 | PZE03170077114 | 171749536 | 0.01915102 | 0.37952685 |
| 4 | PZE01194799632 | 194932443 | 0.85943617 | 1.17238029 |
| 5 | S_7767530 | 171749273 | 1.29880915 | 2.55131038 |
| 6 | S_7767535 | 171749283 | 1.29880915 | 2.55131038 |
| 7 | S_7767546 | 171749318 | 1.29880915 | 2.55131038 |
| 8 | PZE1014822787 | 14764839 | 0.42135623 | 0.26547596 |
| 9 | PZE1014822363 | 14764415 | 0.17635983 | 0.18174604 |
| 10 | PZE0833363225 | 33363625 | 0.06956905 | 1.13162812 |
| 11 | PZE1014822960 | 14765012 | 0.85169843 | 0.91924154 |
| 12 | S_25177407 | 164855482 | 0.69820466 | 0.67099443 |
| 13 | S_3355011 | 14764763 | 1.1780373 | 1.57865605 |
| 14 | PZE1014822606 | 14764658 | 0.56943117 | 0.08699943 |
| 15 | PZE1014822564 | 14764616 | 0.49697049 | 0.33590677 |
| 16 | S_3354810 | 14764696 | 0.44083186 | 0.38491027 |
| 17 | PZE1014822691.S_3354951 | 14764743 | 0.99690825 | 1.20836387 |
| 18 | PZE1014822841.S_3355363 | 14764893 | 0.79186145 | 0.91622315 |
| 19 | PZE1014822866.S_3355438 | 14764918 | 0.79186145 | 0.91622315 |
| 20 | PZE03170076681.S_7767421 | 171749103 | 0.11900814 | 0.00865314 |
| 21 | PZE05126115268.S_11834715 | 126816519 | 0.2079189 | 0.13401627 |
| 22 | S_11834745 | 126816572 | 0.2079189 | 0.13401627 |
| 23 | PZE05126891291 | 127605008 | 0.83345758 | 1.6839096 |
| 24 | PZE05126891427.S_11835752 | 127605144 | 0.83345758 | 1.6839096 |
| 25 | PZE1014822809.S_3355271 | 14764861 | 0.01245327 | 0.74596913 |
| 26 | S_14101102 | 147913800 | 0.32257144 | 0.13757348 |
| 27 | PZE0386521032.S_7281790 | 108707214 | 1.5683837 | 1.31891826 |
| 28 | S_12049233 | 164855895 | | |
| 29 | PZE0833363158.S_16494064 | 33363558 | 0.08469174 | 0.86221774 |
| 30 | PZE0833363197.S_16494076 | 33363597 | 0.08469174 | 0.86221774 |
| 31 | S_3354602 | 14764622 | 0.65441341 | 0.16214315 |
| 32 | PZE03170079878.S_7768070 | 171752300 | 1.35406698 | 0.1877092 |
| 33 | S_25177376 | 164855387 | 0.2351574 | 0.29429341 |
| 34 | PZE0356470659.S_7124418 | 56812375 | | |
| 35 | PZE03170077201.S_7767630 | 171749623 | 0.38453167 | 0.28107766 |
| 36 | PZE1014702229 | 14644281 | 1.13164967 | 0.51957672 |
| 37 | S_3349719 | 14644977 | 1.14601099 | 1.25251975 |

TABLE 2.2-continued

Data for the 113 markers examined for yield under irrigation and yield under drought stress in the five testing panels described in Example 1, continued.

| SNP | Marker | Site | hyb_irr_nss_2008_NegLogP | hyb_irr_nss_2009_NegLogP |
|---|---|---|---|---|
| 38 | PZE03170076798 | 171749220 | 0.78567606 | 0.82631165 |
| 39 | PZE03170078108.S__7767931 | 171750530 | 0.23477054 | 1.23784226 |
| 40 | S__55135874 | 171749906 | | 0.14198191 |
| 41 | PZE01194801358 | 194934169 | | 0.79314162 |
| 42 | PZE1014822786.S__3355207 | 14764838 | 0.24523972 | 1.1831317 |
| 43 | PZE1014822819.S__3355299 | 14764871 | 0.24523972 | 1.1831317 |
| 44 | PZE1014822928 | 14764980 | 0.24523972 | 1.1831317 |
| 45 | PZE03170076953.S__7767584 | 171749375 | 0.12667685 | 1.18035898 |
| 46 | PZE0356471257 | 56812973 | | |
| 47 | PZE1014702037 | 14644089 | 0.38125336 | 0.28426884 |
| 48 | S__3348847 | 14643477 | 0.16215297 | 0.6734687 |
| 49 | PZE03170077026 | 171749448 | 0.2181933 | 0.07603965 |
| 50 | PZE06148080134 | 147915823 | 0.06038515 | 0.54062193 |
| 51 | S__25177378 | 164855388 | 0.23544921 | 0.2283158 |
| 52 | PZE0833363578 | 33363978 | 0.23143252 | 1.07639439 |
| 53 | PZE06148080313 | 147916002 | 0.61740718 | 0.46596029 |
| 54 | S__23029935 | 171752133 | 1.06640515 | 0.51746593 |
| 55 | PZE1014821787.S__3353035 | 14763839 | 1.05948751 | 0.2107891 |
| 56 | S__16494954 | 33368521 | 0.38046935 | 1.02758367 |
| 57 | PZE03170076625.S__7767384 | 171749047 | 0.38453167 | 0.46470533 |
| 58 | PZE05126115149.S__25071732 | 126816400 | 0.41281548 | 0.28286337 |
| 59 | PZE06148078578 | 147914267 | 0.32958285 | 1.04140018 |
| 60 | S__16494695 | 33367991 | 1.0281558 | 0.64993946 |
| 61 | S__33794968 | 164856230 | 1.01816406 | 0.35236426 |
| 62 | PZE1014701114 | 14643166 | 0.08155626 | 0.43892973 |
| 63 | PZE1014822003.S__3353589 | 14764055 | 0.03416064 | 0.53398819 |
| 64 | S__3353692 | 14764202 | | |
| 65 | PZE05126891289 | 127605006 | 0.36125549 | 0.24063273 |
| 66 | PZE05126891675 | 127605392 | 0.36125549 | 0.20252672 |
| 67 | PZE06148077991.S__14100829 | 147913680 | 0.09065364 | 0.02898161 |
| 68 | S__3355358 | 14764891 | | |
| 69 | S__3355625 | 14765003 | | |
| 70 | PZE01194801561 | 194934372 | 0.94554625 | 0.84000889 |
| 71 | PZE05126116874 | 126818125 | | |
| 72 | PZE05126117144 | 126818395 | | |
| 73 | PZE05126889656.S__11835494 | 127603373 | 0.71174015 | 0.44459382 |
| 74 | PZE05126889836.S__11835524 | 127603553 | 0.71174015 | 0.44459382 |
| 75 | S__14100779 | 147913649 | 0.07955528 | 0.15616572 |
| 76 | S__14101249 | 147913892 | 0.00902683 | 0.34687826 |
| 77 | S__12049219 | 164855078 | 0.91412257 | 0.61446207 |
| 78 | PZE03170076986.S__7767599 | 171749408 | 0.30600068 | 0.03369069 |
| 79 | PZE03170076676.S__7767416 | 171749098 | 0.4951291 | 0.32049511 |
| 80 | S__25177445 | 164855596 | 0.30128326 | 0.133377 |
| 81 | S__33794965 | 164856183 | 0.22150278 | 0.48601471 |
| 82 | PZE03170076989.S__7767600 | 171749411 | 0.82255903 | 0.0083933 |
| 83 | PZE03170077032 | 171749454 | 0.82255903 | 0.0083933 |
| 84 | PZE1014702682.S__3349436 | 14644734 | 0.86440975 | 0.22637006 |
| 85 | PZE1014702775.S__3349611 | 14644827 | 0.86440975 | 0.22637006 |
| 86 | PZE08111162512 | 112532312 | | |
| 87 | PZE05126115152.S__11834667 | 126816403 | 0.0251784 | 0.81197321 |
| 88 | S__14101038 | 147913767 | 0.21532276 | 0.20231402 |
| 89 | S__14101413 | 147914335 | 0.07852808 | 0.16386486 |
| 90 | S__49741167 | 194933875 | | 0.21886861 |
| 91 | PZE1014702114 | 14644166 | | |
| 92 | PZE03170078386 | 171750808 | | |
| 93 | PZE03170078405 | 171750827 | | |
| 94 | PZE06148079640 | 147915329 | 0.10227987 | 0.00545827 |
| 95 | PZE1014703058.S__3349905 | 14645110 | 0.72205718 | 0.05191929 |
| 96 | PZE04103664044 | 96311232 | 0.16240214 | 0.0892337 |
| 97 | S__33794964 | 164856180 | 0.01683392 | 0.07885298 |
| 98 | PZE1014703254.S__3350242 | 14645306 | 0.32558755 | 0.51510299 |
| 99 | PZE01194799750.S__20076659 | 194932561 | 0.29531278 | 0.00565575 |
| 100 | PZE1014701102 | 14643154 | 0.37088935 | 0.62915452 |
| 101 | S__7124415 | 56812284 | | |
| 102 | S__3354083 | 14764448 | | |
| 103 | S__3354105 | 14764455 | | |
| 104 | PZE05126889689 | 127603406 | | |
| 105 | PZE1014821892.S__3353328 | 14763944 | | |
| 106 | PZE01194800515.S__20076953 | 194933326 | 0.48477092 | 0.03444593 |
| 107 | PZE03170079877.S__7768069 | 171752299 | 0.37278741 | 0.45828978 |
| 108 | S__3350152 | 14645275 | | |
| 109 | PZE06148077958.S__14100776 | 147913647 | 0.21745347 | 0.23155189 |
| 110 | S__3353995 | 14764418 | | |
| 111 | PZE1014700929 | 14642981 | | |

TABLE 2.2-continued

Data for the 113 markers examined for yield under irrigation and yield under drought stress in the five testing panels described in Example 1, continued.

| SNP | Marker | Site | hyb_irr_nss_2008_NegLogP | hyb_irr_nss_2009_NegLogP |
|---|---|---|---|---|
| 112 | S_20077149 | 194935223 | | |
| 113 | PZE0356471931 | 56813647 | | |

TABLE 2.3

Data for the 113 markers examined for yield under irrigation and yield under drought stress in the five testing panels described in Example 1, continued.

| SNP | hyb_irr_ss_2008_NegLogP | hyb_irr_ss_2009_NegLogP | hyb_str_nss_2008_NegLogP | hyb_str_nss_2009_NegLogP |
|---|---|---|---|---|
| 1 | | | 3.39143188 | 1.4803721 |
| 2 | 0.17035041 | 0.15083801 | 0.04265472 | 1.38336068 |
| 3 | 2.60149002 | 0.46241344 | 0.10046913 | 0.45416226 |
| 4 | 0.24142934 | 0.37040433 | 0.42821394 | 0.28761583 |
| 5 | 1.24732304 | 1.34656524 | 0.47643233 | 1.12107774 |
| 6 | 1.24732304 | 1.34656524 | 0.47643233 | 1.12107774 |
| 7 | 1.24732304 | 1.34656524 | 0.47643233 | 1.12107774 |
| 8 | 0.08226949 | 0.69270568 | 0.76344493 | 0.20260388 |
| 9 | 0.0394166 | 0.6487939 | 0.0324467 | 0.17463126 |
| 10 | 0.66515757 | 0.33654449 | 0.69628303 | 2.31572792 |
| 11 | | | 2.31533522 | 1.01516461 |
| 12 | 0.89221201 | 1.41575634 | 0.00794551 | 0.26033852 |
| 13 | | | 2.20181199 | 1.86373415 |
| 14 | 0.01009048 | 0.5880692 | 0.66912419 | 0.6967561 |
| 15 | 0.03978049 | 0.66876859 | 0.68017307 | 0.28246053 |
| 16 | 0.11586244 | 0.56134977 | 0.52037422 | 0.33815468 |
| 17 | | | 1.87979971 | 0.94138623 |
| 18 | | | 1.80179111 | 0.9850086 |
| 19 | | | 1.80179111 | 0.9850086 |
| 20 | 0.90166818 | 0.14862839 | 0.42571055 | 0.16682025 |
| 21 | 0.07171003 | 0.2249717 | 0.11157745 | 1.75450587 |
| 22 | 0.07171003 | 0.2249717 | 0.11157745 | 1.75450587 |
| 23 | | | 0.1680075 | 0.3179246 |
| 24 | | | 0.1680075 | 0.3179246 |
| 25 | 0.21064378 | 0.55333316 | 0.38183604 | 0.7257265 |
| 26 | | | 0.27214435 | 0.01218352 |
| 27 | | | 0.36668521 | 1.0273156 |
| 28 | 0.06916874 | 0.92722315 | | |
| 29 | 0.54143235 | 0.62092881 | 0.24379132 | 1.46841459 |
| 30 | 0.47882086 | 0.72908185 | 0.24379132 | 1.46841459 |
| 31 | 1.40942615 | 0.2525479 | 0.33747166 | 0.17561225 |
| 32 | | | 0.22775511 | 0.20636099 |
| 33 | | | 0.16613632 | 0.07044957 |
| 34 | | | | |
| 35 | | | 0.00674386 | 0.21213239 |
| 36 | | | 1.27178032 | 0.52889891 |
| 37 | | | 0.70339154 | 0.67286045 |
| 38 | 0.00880482 | 0.37389168 | 0.98180881 | 1.23848499 |
| 39 | | | 0.27464134 | 0.1701788 |
| 40 | 0.60955534 | 0.10276846 | | 0.13080242 |
| 41 | | | | 0.14467926 |
| 42 | | | 0.58093681 | 0.49845824 |
| 43 | | | 0.58093681 | 0.49845824 |
| 44 | | | 0.58093681 | 0.49845824 |
| 45 | | | 0.02818854 | 0.11809184 |
| 46 | 0.2603309 | 0.54498871 | | |
| 47 | 0.07871399 | 0.15019633 | 0.84039179 | 1.16318697 |
| 48 | 0.21488713 | 0.00364405 | 0.6531258 | 1.16156555 |
| 49 | 0.32048789 | 0.03471632 | 0.09529312 | 0.01989565 |
| 50 | | | 0.17180631 | 0.01684251 |
| 51 | | | 0.372673 | 0.15935658 |
| 52 | 0.18352772 | 0.60785611 | 0.17161956 | 0.78005224 |
| 53 | 0.09885423 | 0.70315714 | 0.85810591 | 0.09850591 |
| 54 | | | 0.14280239 | 1.0603578 |
| 55 | | | 0.00214107 | 0.26888295 |
| 56 | | | 0.11795649 | 0.304178 |
| 57 | | | 0.00674386 | 0.09139199 |
| 58 | | | 0.20615436 | 1.04273075 |
| 59 | | | 0.07559816 | 0.41486199 |
| 60 | | | 0.50471775 | 0.31009355 |

TABLE 2.3-continued

Data for the 113 markers examined for yield under irrigation and yield under drought stress in the five testing panels described in Example 1, continued.

| SNP | hyb_irr_ss_2008_ NegLogP | hyb_irr_ss_2009_ NegLogP | hyb_str_nss_2008_ NegLogP | hyb_str_nss_2009_ NegLogP |
|---|---|---|---|---|
| 61 | | | 0.32385166 | 0.43967138 |
| 62 | 0.10343422 | 0.19339268 | 0.16128381 | 0.24096409 |
| 63 | | | 0.08954728 | 0.4201517 |
| 64 | | | | |
| 65 | 0.39490445 | 0.86126817 | 0.06464071 | 0.54750432 |
| 66 | 0.39490445 | 0.86126817 | 0.06464071 | 0.64083061 |
| 67 | | | 0.1292642 | 0.08327594 |
| 68 | 0.70286357 | 0.01891023 | | |
| 69 | 0.70286357 | 0.01891023 | | |
| 70 | | | 0.30345124 | 0.89740677 |
| 71 | | | | |
| 72 | | | | |
| 73 | | | 0.70017186 | 0.24389019 |
| 74 | | | 0.70017186 | 0.24389019 |
| 75 | 0.8337981 | 0.32359724 | 0.20778395 | 0.74528403 |
| 76 | 0.8337981 | 0.32359724 | 0.14437167 | 0.6873758 |
| 77 | 0.60321326 | 0.01628966 | 0.23165403 | 0.22630309 |
| 78 | 0.17164071 | 0.64915989 | 0.15059474 | 0.51382078 |
| 79 | | | 0.09857463 | 0.05819587 |
| 80 | 0.76351467 | 0.18058756 | 0.11714046 | 0.32463538 |
| 81 | 0.25865768 | 0.25946203 | 0.18284056 | 0.08950717 |
| 82 | 0.29490762 | 0.33754669 | 0.33860049 | 0.34734388 |
| 83 | 0.29490762 | 0.33754669 | 0.33860049 | 0.34734388 |
| 84 | | | 0.72135738 | 0.34154198 |
| 85 | | | 0.72135738 | 0.34154198 |
| 86 | | | | |
| 87 | | | 0.10947197 | 0.56609322 |
| 88 | | | 0.20347512 | 0.80043395 |
| 89 | | | 0.19501085 | 0.79763293 |
| 90 | | | | 0.21436624 |
| 91 | 0.36200708 | 0.61187712 | | |
| 92 | | | | |
| 93 | | | | |
| 94 | | | 0.18954134 | 0.74141519 |
| 95 | | | 0.66093211 | 0.12520398 |
| 96 | 0.23307677 | 0.67286986 | 0.25142866 | 0.03662018 |
| 97 | 0.43441612 | 0.34207415 | 0.00147716 | 0.57908725 |
| 98 | 0.0146588 | 0.28840556 | 0.12406035 | 0.63250236 |
| 99 | | | 0.14284817 | 0.63099133 |
| 100 | 0.56137911 | 0.27352189 | 0.07446952 | 0.19202566 |
| 101 | | | | |
| 102 | | | | |
| 103 | | | | |
| 104 | | | | |
| 105 | | | | |
| 106 | | | 0.03055306 | 0.2105521 |
| 107 | | | 0.07977212 | 0.18803518 |
| 108 | 0.42740335 | 0.03697505 | | |
| 109 | | | 0.14762923 | 0.30591534 |
| 110 | | | | |
| 111 | 0.05763862 | | | |
| 112 | | | | |
| 113 | 0.14662528 | | | |

TABLE 2.4

Data for the 113 markers examined for yield under irrigation and yield under drought stress in the five testing panels described in Example 1, continued.

| SNP | hyb_str_ss_2008_ NegLogP | hyb_str_ss_2009_ NegLogP | inb_irr_NegLogP | inb_str_NegLogP |
|---|---|---|---|---|
| 1 | | | 0.373054399 | 0.076996764 |
| 2 | 0.20384843 | 0.279931 | 1.500484195 | 0.670790029 |
| 3 | 0.4399636 | 0.59132297 | 0.62228643 | 0.656175758 |
| 4 | 0.31037268 | 2.55740394 | 0.120744517 | 0.986680896 |
| 5 | 0.80420835 | 0.491335 | 0.499833323 | 0.636127781 |
| 6 | 0.80420835 | 0.491335 | 0.499833323 | 0.636127781 |
| 7 | 0.80420835 | 0.491335 | 0.499833323 | 0.636127781 |
| 8 | 2.40231752 | 1.26800461 | 0.295774098 | 0.009709508 |
| 9 | 2.37737739 | 0.56688203 | 0.43065048 | 0.452683321 |

TABLE 2.4-continued

Data for the 113 markers examined for yield under irrigation and yield under drought stress in the five testing panels described in Example 1, continued.

| SNP | hyb_str_ss_2008_NegLogP | hyb_str_ss_2009_NegLogP | inb_irr_NegLogP | inb_str_NegLogP |
|-----|---|---|---|---|
| 10 | 0.59938658 | 0.66878475 | 0.114010795 | 0.005951511 |
| 11 | | | 0.221808508 | 1.379449511 |
| 12 | 0.12046294 | 2.25430347 | 0.50578442 | 0.043683773 |
| 13 | | | 0.285182163 | 0.355048953 |
| 14 | 2.12591997 | 0.82126335 | 0.220915086 | 0.062437492 |
| 15 | 1.99301641 | 1.0064282 | 0.266411049 | 0.165332726 |
| 16 | 1.9395473 | 0.41006296 | 0.534310238 | 0.03807785 |
| 17 | | | 0.079928948 | 0.817674324 |
| 18 | | | 0.088895297 | 1.373614984 |
| 19 | | | 0.088895297 | 1.373614984 |
| 20 | 0.92387922 | 1.75651396 | 0.324044082 | 0.093021432 |
| 21 | 0.46952224 | 0.18876057 | 0.114311589 | 0.013256512 |
| 22 | 0.46952224 | 0.18876057 | 0.114311589 | 0.013256512 |
| 23 | | | 0.836334763 | 0.087089228 |
| 24 | | | 0.539590869 | 0.084772044 |
| 25 | 1.61522161 | 1.1499741 | 0.571634535 | 0.507395516 |
| 26 | | | 0.329899175 | 1.569756551 |
| 27 | | | 0.03812525 | 0.004129948 |
| 28 | 0.39220084 | 0.00338498 | 1.48318061 | 0.732881644 |
| 29 | 0.55694877 | 0.37947032 | 0.567011759 | 0.08501641 |
| 30 | 0.6647357 | 0.37074831 | 0.306606148 | 0.014619638 |
| 31 | 1.21178291 | 0.08659301 | 0.661369831 | 1.128088593 |
| 32 | | | 0.196916201 | 0.318886372 |
| 33 | | | 1.123148402 | 1.339399124 |
| 34 | | | 0.435339592 | 1.304043311 |
| 35 | | | 1.275031713 | 1.000595196 |
| 36 | | | 0.053296334 | 0.366012088 |
| 37 | | | 0.111741885 | 1.035595681 |
| 38 | 0.05943094 | 0.34197826 | 0.244403507 | 0.394698158 |
| 39 | | | 0.614657472 | 0.828193448 |
| 40 | 0.57384751 | 1.22686808 | 0.617441001 | 0.369195761 |
| 41 | | | 0.898600064 | 1.192877118 |
| 42 | | | 0.635189751 | 0.031774589 |
| 43 | | | 0.462109042 | 0.215332784 |
| 44 | | | 0.462109042 | 0.215332784 |
| 45 | | | 0.75070662 | 0.884372283 |
| 46 | 1.17308179 | 0.34275546 | 0.07392808 | 0.084881527 |
| 47 | 0.09087783 | 0.38867158 | 0.500719704 | 0.329135138 |
| 48 | 1.0650841 | 0.40541214 | 0.498098923 | 0.667240935 |
| 49 | 0.31924899 | 1.13040968 | 0.740420949 | 0.049688845 |
| 50 | | | 0.280607024 | 1.119239292 |
| 51 | | | 0.880406377 | 1.08889322 |
| 52 | 0.11788978 | 0.47142233 | 0.991926824 | 0.759895665 |
| 53 | 0.54691989 | 0.64743411 | 1.069873955 | 0.093545818 |
| 54 | | | 0.099635146 | 0.046375319 |
| 55 | | | 0.054219933 | 0.02205439 |
| 56 | | | 1.058658119 | 0.439031785 |
| 57 | | | 0.923674412 | 1.046945321 |
| 58 | | | 0.601254631 | 0.497986267 |
| 59 | | | 0.923313767 | 0.949017422 |
| 60 | | | 0.106412931 | 0.31940991 |
| 61 | | | 0.118543162 | 0.035742647 |
| 62 | 1.01322275 | 0.20034712 | 0.574197909 | 0.317530916 |
| 63 | | | 0.315598219 | 1.007936407 |
| 64 | | | 0.902677655 | 0.978997285 |
| 65 | 0.976811 | 0.81332864 | 0.751278108 | 0.029576463 |
| 66 | 0.976811 | 0.81332864 | 0.813942695 | 0.150877497 |
| 67 | | | 0.530561112 | 0.965785588 |
| 68 | 0.95496493 | 0.24304959 | 0.031225577 | 0.139501054 |
| 69 | 0.95496493 | 0.24304959 | 0.005118358 | 0.126327378 |
| 70 | | | 0.13507934 | 0.300988246 |
| 71 | | | 0.381404942 | 0.941261233 |
| 72 | | | 0.381404942 | 0.941261233 |
| 73 | | | 0.367861331 | 0.928155204 |
| 74 | | | 0.367861331 | 0.928155204 |
| 75 | 0.91902831 | 0.3474665 | 0.321751596 | 0.238776131 |
| 76 | 0.91902831 | 0.3474665 | 0.328244125 | 0.006892388 |
| 77 | 0.26628927 | 0.30360471 | 0.172661772 | 0.094141347 |
| 78 | 0.08720609 | 0.90116286 | 0.363779149 | 0.260174022 |
| 79 | | | 0.754839994 | 0.889639553 |
| 80 | 0.55842804 | 0.88741576 | 0.189868222 | 0.442479239 |
| 81 | 0.43630846 | 0.88582055 | 0.738200969 | 0.103855159 |
| 82 | 0.53951015 | 0.87508174 | 0.419856631 | 0.025420967 |
| 83 | 0.53951015 | 0.87508174 | 0.419856631 | 0.025420967 |

TABLE 2.4-continued

Data for the 113 markers examined for yield under irrigation and yield under drought stress in the five testing panels described in Example 1, continued.

| SNP | hyb_str_ss_2008_ NegLogP | hyb_str_ss_2009_ NegLogP | inb_irr_NegLogP | inb_str_NegLogP |
|---|---|---|---|---|
| 84 | | | | |
| 85 | | | | |
| 86 | | | 0.839293909 | 0.196563596 |
| 87 | | | 0.216988836 | 0.022491942 |
| 88 | | | 0.321896287 | 0.323990061 |
| 89 | | | 0.141113753 | 0.344734649 |
| 90 | | | 0.782004637 | 0.403715325 |
| 91 | 0.42557976 | 0.16817132 | 0.694102707 | 0.754336779 |
| 92 | | | 0.313314916 | 0.747050149 |
| 93 | | | 0.313314916 | 0.747050149 |
| 94 | | | 0.106311353 | 0.053774493 |
| 95 | | | 0.595745125 | 0.652391602 |
| 96 | 0.33750562 | 0.35698415 | 0.080388865 | 0.02798058 |
| 97 | 0.26156448 | 0.60952707 | 0.637038663 | 0.157100172 |
| 98 | 0.15963718 | 0.28587802 | 0.361150032 | 0.061883957 |
| 99 | | | 0.334722878 | 0.415136614 |
| 100 | 0.04369916 | 0.07755263 | 0.213980447 | 0.053872558 |
| 101 | | | 0.428339218 | 0.610827375 |
| 102 | | | 0.537479086 | 0.609312506 |
| 103 | | | 0.537479086 | 0.609312506 |
| 104 | | | 0.186312847 | 0.579248188 |
| 105 | | | 0.267221962 | 0.509327867 |
| 106 | | | 0.023529605 | 0.046735768 |
| 107 | | | 0.04557972 | 0.078764555 |
| 108 | 0.15789273 | 0.02014709 | 0.073885391 | 0.260104342 |
| 109 | | | 0.074211147 | 0.360438138 |
| 110 | | | 0.202889986 | 0.005580223 |
| 111 | 0.19986353 | | | |
| 112 | | | 0.097822876 | 0.194000286 |
| 113 | 0.16996956 | | 0.07392808 | 0.084881527 |

Example 2. Identification of Markers Associated with Increased Yield Under Non-Drought Conditions, Increased Yield Stability Under Drought Conditions, and/or Increased Drought Tolerance Several family based association studies (FBAM) were performed to identify markers associated with three yield traits (yield under irrigation, yield under drought stress and the difference between them) using diverse inbred and hybrid panels of maize. Populations from 24 parental lines were used to generate the families (progeny lines) used in the NSS analyses. In total these parents had 167,854 variants segregating among them. The 24 parental lines were sequenced using a reduced genomic next generation sequencing approach and used to project the next generation sequencing variants onto the families within each population (or cross). Merging the genotypic and phenotypic data from the NSS-MSE analysis resulted in 24 parental lines crossed to generate 45 populations which had a grand total of 1040 families. These families were then crossed to two testers. Populations with less than 10 families were excluded from the analysis since they would provide little additional value.

Twenty parental lines were used to generate the populations and families for the SS datasets. Across these twenty parents 112,466 variants were segregating. Similar to the NSS datasets, parental lines were sequenced using a reduced genomic next generation sequencing approach and used to project the next generation sequencing variants onto the families within each population (or cross). Upon merging this genotypic data with the phenotypic data there were 23 populations and a grand total of 553 families that had genotypic and phenotypic data available. Replicates from these families were then crossed to two testers to generate the hybrids that were phenotyped.

The two initial models tested were the fixed effect model with interaction term (1) tested using PROC GLM in SAS and a random effect model with interaction term (2) tested using PROC Mixed REML in SAS.

$$y=\text{Population (fixed)}+\text{SNP(fixed)}+\text{Population}\times\text{SNP (fixed)}+\varepsilon \quad (1)$$

$$y=\text{Population (random)}+\text{SNP(fixed)}+\text{Population}\times\text{SNP (random)}+\varepsilon \quad (2)$$

Those markers showing a significant association with yield (YGSMN) when grown under irrigated conditions (non-drought) are provided in Table 3.

Nucleotide Sequences
Genomic Sequences B73 Maize

```
ZmSWEET13a [GRMZM2G173669]
Genomic sequence/Gene region- >lcl|GRMZM2G173669 seq = gene;
   coord = 10: 14762443 . . . 14765098: 1
                                                          SEQ ID NO: 1
GCCTATATAAAGCCACCCACAGCCCTGCCTATCATTGCAAGAGTTTGAGCCAACACACACAGAGAGAGGACAACTCCTCA CAACTCTCCCTTCCCTCCTGTAGGGGCCAAAAGGGTTAGAGAGTAGGAGAAGTAGTTCCCTAGCCCAACACAAGAAAAAC
```

-continued

```
AAGCTCGATCTCCTCATCACCCTAATCCAAGCAACTGCTTTGTGTGTTGGGAAATTCTTGTGACCCCTGTTATATTATTA

TCCGTGTAGCTACTAGCTTCATTCCCCCCTTTGTACCCATCAAATGGCTGGCATGTCTCTGCAACACCCCTGGGCGTTTG

CTTTCGGTCTACTAGGTACATACTACACCTTCACTAATAGCTAAACAAGCGCCCGCCGCAAAGCTATGAATTAAGGGCAG

GCATGTTTGGTTTGCTACCTATTTTACCATACTTTGTCTAACTTTTCTGTCTAAGGTTATAGTTCTTCAATTCGAACGAT

TAATCTTAGCCAAAGTGTGACATGGTTAGCCACGAACTAAGCAGGCCCTTAATTATTGCGCATGTATATATTATATATTT

ATCTTTCTATTCTGTTTAATTTGTTTTCTCTTTACATATATATACTACTATGTAAGTATATATTATATGCACAACAAGCA

GGCCTCCTTCGTGCACATATGCATAGAATCAATCTATACCCTTCATAGAAGCCACTTTGAGATATACCTTCCAAAACAAT

CCCAAAAACAAGACGCTCGATCTTGCGCTCACAATCACTTAGTTTTGCACCAGATTAAGCATGCACCACTAGATTTTATG

TACTGTATTACCTCTGCCATCCATGGTCGATCCTTTAGTTTATCCTATTCATTTCCGTCATGAACTACCTGTCGAGCTAG

CAATCGGTCCTTTATTTAGAGTGTTCAGATAGGCATCTGTCTTTATACAAACAATAAAGCCTCACGAATCTTTAGTCACA

AAACAAGGCAAATTAGACAGGCCACGGAGGTGTAAAGTGTCAGCTCTGCTTATCACAACTTATCTCTGCTTTATTTGGGC

ACACTTTTGCCATACAAATGGCTGATCTTGGCGCCTTTTTTTTCTCCTTGCTTTGCAGGTAACGTCATCTCCTTCATGAC

CTTCCTGGCCCCGATGTAAGTGACATATATATATATATATTGCTTAATTAATTATCACTGCTTCTTCAGATATATATT

CATCGGTTATTTTAATTAATTATGTGGATATGTATGCATCGTATAACAGACCGACGTTCTACCGCATCTACAAGAGCAAG

TCGACGGAAGGCTTCCAGTCGGTTCCCTACGTGGTTGCCCTGTTCAGCGCCATGCTGTGGATCTTCTACGCACTGATCAA

GTCCAACGAGACCTTCCTCATCACCATCAACGCCGCCGGCTGCGTCATCGAGACCATCTACGTCGTCATGTACTTCGTCT

ACGCGCCCAAGAAAGCCAAGCTGTTCACGGCCAAGATCATGGTCCTCCTCAATGGCGGCGTCTTTGGGGTCATCCTCCTG

CTCACCCTTCTCCTCTTCAAGGGCAGTAAGCGCGTTGTGCTGCTTGGCTGGATCTGCGTCGGCTTCTCCGTCAGTGTCTT

CGTCGCGCCACTCAGCATCATGGTGAGCCCTGAGCACGCGTATAAAACTGTGCCAAGATGCATGGACGACAGATCGATCA

ACCCAATCAGTTTTGATCCATGTGTATCGTTTCTAATGCACCGTGTTTATATATGTGTGCAGAGACGAGTGATCCAGACG

AAGAGCGTGGAGTACATGCCCTTCTCCCTCTCCCTCTCGCTCACCCTCAGCGCCGTCGTCTGGTTCCTCTACGGCCTCCT

CATCAAGGACAAATACGTCGCGGTAATTGTTTCATCTAATCTGCTGCAACCGCCATGGTATTGGTATCTCTCACTGGTCT

TTACTGATAAACTACATACGATCTCTGTACGTATGCAGCTTCCAAACATCCTGGGGTTCACCTTCGGCGTGGTCCAGATG

GTGCTCTACGTGTTGTACATGAACAAGACGCCGGTGGCGGCGACTGCCGAGGGCAAGGATGCCGGCAAGCTTTCCTCAGC

TGCAGACGAGCACGTCCTCGTCAACATCGCCAAGCTCAGCCCAGCCCTCCCGGAGAGGAGCTCCGGGGTGCACCCAGTCA

CCCAGATGGCGGGCGTTCCTGTCAGGAGCTGCGCTGCTGAAGCAACCGCGCCGGCGATGCTGCCCAACAGGGACGTGGTC

GACGTCTTCGTCAGCCGACACAGCCCCGCCGTCCACGTGGCATAGATTCTCGATCGATCGCGTGCATGGCCCATGCATGC

GCCCGCCACACGTACGCTAGCTTTTATATATTCGAAGGACGACTTGCTGCTGGTCGTGAGCATATATATGATGGAGAAAA

TGATTAAGTAGTATATATATAAGTAATTAACTGCCATGCATGGAAGCTAGCTAATGGATGGAGGCAGAGGCCAGAACGAT

GAAGGGGGAAGCTATACATATATGTGTGTAATTAATATAGATATATGGGCTTTGTGTTCATCTTTGCAGCTATGTATTAA

TTTGCATGGATATCTGTTATTCCTTTTTATGTGTAACGTCTTCTAATAAAATGTAATTGAACCCACACTACTGTTGTTAG

CTACCACAAGTTTCCC
```

ZmSWEET1a [IGRMZM2G039365]
>1c1|GRMZM2G039365 seq = gene; coord = 3: 171748815 . . . 171752467: -1

SEQ ID NO: 2

```
GGCTCTCTTCTCCACCGGTCCTACCCCTTACCTCCCAAGATCACAATCCTCTGCTCCTTATATATTAGCCACACCGCTCG

TTCCCTGCTGCACCGGGTGACACACAGGCACAAAGACACCGCCCGTACACAGGCTCGTTGGCTTGGCTGCTGTGTGTTGC

GCTCAGCCATTCAGACTTGAGAGCTACTAGCTAACTGCTCGTTGGGTGTGGGTGCGCTCCCGGCCTAGACCGTGGAGGAA

AGGAGTCCAGTCCACTCACTACCCCCTCTGCTCCGTTCGGGTTCCAGGCCAGCACAGCCGAGGGTTCCGCACAGCGATAA

GCGCGAAGCGGAAGAGATGGAGCATATCGCCAGGTTCTTCTTCGGAGTTTCTGGTCAGTATCACCATGCCATTCCTGCCT

CTGCTGCATGCCTACCTGATGGTCTTCTTCTTGCCTCGCCTAATCTCTGTTAGATCTGTCTCCCCAGGGAATGTCATTGC

GCTCTTCCTCTTCCTGTCGCCTGTGTAAGTTTTTGATTCCACGTACCTGAATCCTTCTGTTCCTCACTGCCCGCGTCCAT
```

-continued

```
GCTTTAAAAAAAAAATCGAAAACAGAGAAGCAATGATATAGTACTTACTTCTACTATATGACAAAGACTAGAACATGGGG
AGAATCAGTGTGGAGAGAAAGGCTATAGCATCTTTTAGGTTCAATCCTTTCCAGCGAAACACTGAAATTTCATACATATA
TAATTTTTTTCTAAAAAAAGCAAGTAGCTTTTCCCCATCCGAAATGCTTCTTCTTCCCAACCACGCCGCACCTTTTTTCT
TGCGTCTTGCCTCAGCAGCCTTCAGGGGCAGCAGCGCAGTGCGTGTGTTCCTCTGACGGGTGAGAAATCTCTTTGCAGTG
TCACCTTCTGGAGGGTCATCAGGAAGCGGTCGACGGAGGACTTCTCCGGCGTGCCCTACAACATGACGCTGCTCAACTGC
CTCCTATCGGCTTGGTAACGAACCGCTCTCTCTCTCTCTCTCCCTGAGAGACACGGCCTTTTGATGAGCACTCCACAC
CATTTCTGTTTCTGTCTCTTCAGAAAATTAAATCGCATCGCAGATTTATGGAGTGGCCGTAAAGCAGTAAAACCGGCGTG
GTGGTGTAGTTTGTTTTACTTAGATTTCGGAAATGCTGCATGGTTTGCTGGCCTGGGTGAAGCAAACGCTTGGCTCCTAG
CGTAGCCTCTGCCCAACCCGGCCTGTCCTGTAGATAGAGTACTACCCGTGGACCCACTCGCTAGACGCTAGCACTGTAAG
TCTGTGACAACGACTGCAATGAAGGGGGAAAAGCTTATTGCACTGCACCACTGCCCGTGGGAGCAGAGCCTACCTGTTGG
CATTGCCAGGACGGAGATGACGACCTGTGGGCCTCGCGGCCCTTGAGCCCGCACATGCAGCGTCACGTTCAAGTGTTCGT
ACCTCCAAACAAAAAAGTCTTGACGCTTTTTTTTTCTTTTGGTTATTATGATGACGGACGATTCTGGTCAGGGCATC
CACATAAATATCTTAAAAGGTATTAACGACGTAAGTGCAAAAAAAAGACAGTCTCTAGCACTACCACGGTTTTATCCAT
ACAACTCACGTACATGAATCATATCATGAGATCTTCTAGTGGAATAAGATATAAAACTTAAATATATTGGGCTATATGAA
AGAGTTTTTTAGATGTATTTAGTGCTTAAAGAACTGAAACGTAGTATCTAGATTGTACATGTCTTTATGACTATATGGAT
GAGTTGGTGTCCCGTTTGATTTTTCACGCGCCTTTGAATCCATGTGAAGATCGATGTGCTAGCTAGCTAGCTCGCTCTTC
ATGCGTTCGTCTGGATTTTGTTTGAAATTCACGCAGCATATATGTGTGGAATATAATCTGTATGCACATACAGGTACGGC
CTGCCGTTCGTGTCCCCGAACAACATCCTGGTGTCGACGATCAACGGGACGGGGTCGGTGATCGAGGCCATCTACGTGGT
GATCTTCCTCATCTTCGCGGTGGACCGGCGGGCCAGGCTCAGCATGCTGGGCCTCCTGGGCATCGTCGCCTCCATCTTCA
CCACCGTGGTGCTCGTCTCGCTGCTGGCCCTCCACGGCAACGCCCGCAAGGTCTTCTGCGGCCTCGCCGCCACCATCTTC
TCCATCTGCATGTACGCCTCGCCGCTCTCCATCATGGTACGTGAGCGATGATGATTGGTTGTTGCTGCCTTGCTGGGTAG
CTAGCTCCAGCGGGTCCCCTTCTGGGCGTGTACGTGCGTCCTTGCTGTCAACGTACGGCATCAGTTAACAAGCTAAGCGT
GTGCTTGGTGTGTGCAGAGGCTGGTGATCAAGACGAAGAGCGTGGAGTTCATGCCGTTCCTGCTCTCCCTGGCCGTGTTC
CTGTGCGGCACCTCCTGGTTCATCTACGGCCTCCTCGGCCGCGACCCCTTCATTATTGTACGCACACGGTTCTCTCTCTA
GTCTAGATCCTGAGCCGCACTCACCGCCCGGCCGTACGCACGTGCTATCCGCGCATGTTGTCCGATTGGCACTCGGAAAC
CACTGTAGCAGCACTGTATCACTAGCTGTTGGGACTGGACGTAACTGCATCTGATCTGGCCAGCACAGTACCCCCGGGCT
GGGCGTCGGTTGCCCTTTCGATGTCCCGCCCAAGCCCAACCAGGCGCACATGCCTGCCGCTGCCGCAGCCGATGCACGGG
CATGGGCGCCGGTAGCGTCTAGCAGCGTGGGCGTGGCCACCCACAGGCAGCGCACGCCGGTGCTAGCTGCCGATGGGCCG
CCGTGCCCATGTCCATGCAGCTGGATTGGACCCGGCACAGGCAGAAGCAACAGCGCCCGCGCTCTTTCTTGTCGCAATGC
TAGTTAGCAAACTGCACGGTGCACTCCACTTCAGTACACACCAACGCGACAGACTGCGATGAAATATCTAAGGCCGAGTT
TTTTTTTTTGCAAATCTCATCATGTCGGAATGATTCATGCGGTCCAAACTTCAGCACACCCCCACTGTCGCTAAACCCG
CGCTGTCTGTGCATGCGTGCAGATCCCGAACGGGTGCGGGAGCTTCCTGGGCCTGATGCAGCTCATCCTGTACGCCATCT
ACCGGAAAAACAAGGGCCCCGCCGCGCCGGCCGGCAAGGGAGAGGCCGCCGCCGCCGCGGAGGTGGAGGACACCAAG
AAGGTGGCCGCTGCCGTGGAGCTGGCCGATGCCACGACCAACAAGGCAGCGGACGCCGTCGGCGGCGACGGCAAGGTCGC
CAGCCAGGTGTAGGCGGGCAAGGCTTATTTGCTGTCTGGGACTGGGAGGAACATCCTAAACGAGGCTGCCTTAGTTTGTC
GGTGGAGCAGATTGGTGTTGGTTTCTGTGGGCTTTTACGGTTGTTGTTACTCTCATCTCCATCTCTCCCAGGAGGCTACC
CCAAGCATGTAGTAGCTTCCATTCTGATTCTGGGACGGTGTTGCACGTTACAGTGCTCTCAAGCTGTCTCTGCAAAGTGT
```

```
GTTTTTTTATTCCATTTCCCTCCTGCTCTTGTTCTCCAACTGCGCTTACCTGCCCCCGATTTCTCTAAAAAATGTATTAA

ACTATCTGAGAAATTCATCCAACTGCGAGTACTGTGCTGTGCGTGAGCAATGC

ZmSWEET11/MtN3 [GRMZM2G368827]
>lcl|GRMZM2G368827 seq = gene; coord = 1: 194932443 . . . 194935353: -1
                                                              SEQ ID NO: 3
ACACACAAACACATCAGCATTCAGCAATAGCTAATCGAGCATCGTCGCCTTAGCTCCTCTCCTCTCCTCTCCGTCGTCGT

GGAACTTCTCTCCGCCGGCTGTCATATATATAAAGGAGAAGAAGAGAACAGCAACTCTAGCTAGCCGGCCGGCCTCCGTC

GTCGCCGGCGTCGTCGACTAGCTAGCTAACTCTCGATCTCCAGTTCCTGCCCCCGCGCCCCACGCCCGGCCGTCGTCGTC

AGCAATGGCAGGAGGCTTCTTCTCCATGGCTCACCCGGCCGTCACCCTCTCCGGCATCGCAGGTACGTACGCGCCAATGA

AACAACAACGTCGTCTCGAGCTAGATCGATCCATGCATGACGCCGGCCGGGACCGGCCGGATAGATAGGCGGAGATCGAC

TTGCATAATGCTTCGCGTGTTTGGCCTTTTCCTGGTGCTTCTTTTTTTTTTAAAAAAAATCTTATGGGACCTTGATGAC

ATGCTTTTCATGTGGTTTTCATTCATTCTGTTGCCGTACTACGTTCTTCTAGATTTTGTTTATTCCGACATGACGACTGT

CTTGTCCATCCTTGTATCATCGATCCGTCCTTTGCATGCATGCATCCACCAGTCGTCAGCCTTCCTTTTTGCCGTTTGTG

CCATTGCACTGTAGAGCACGCACGCACTCTCTAGCTGTAGAGAGGCGCGGCAGTAGGCATGCATGCAGCAGCTAGTCACA

CTGGACAACCAACTGTCTTGTCCATCATCTATCAACAATACTTGCATATCAGAATACGTAGTATGTAGCTTTAGCATTTT

TTTTTCTTCACCTATACTACTGCTAGCTGCATCTTCTTGAACTTTCTCTGATGCTCCCCGCGGCCCATTGAGACGACGAT

GCACTCTTTCTCCAATTCGTTAGCTGCGATCATGGCACAGGCCTTTAATTTGTTGCTAGCTAGAACACACATGCATGCAT

CGCCGAGGTATAGCAACTTTTCCACTCAAGAATAATGGTAATAAGCAGTGCAGATCAGATCCACATATTGGGCATTAGAT

CACGAAATACAGTTGCAAATAGCTGCTCACAACGTAACGCACTATCTAAGAATCATTTCTATATACGTGTATTTTTGCT

GGAATGGTTATGATCGATCGGTTGGGCATGCAGCAGGGAAGGCGTGTGCGTGTGCATGCAGCTACCTAGCTTTTTGCCAT

ATCAGCGTTTCCTTAACCTAATCACCACGCTTCTCTCTGTTAGTGGACGCACACGCATTGTACATATATATGTGTATAGT

ATTGTACTCCTACCACTTTTACTGAAAATGACGACACTGACGCGTAGTTACCCTCTTCTCTCTTGTTTCTTCGATTTGGA

TTGTGCAGGAAACATCATCTCCTTCCTGGTGTTCCTTGCACCAGTGTAAGTAGCTAGCTATAGCCACCTTTCTTCGTTCC

CTTACTGTCTCAATTTCAGACCGACTCGGATTCATGCGTGAATCGATGGATGATCCAAGACTGACATGGCATGCCTCTTG

TACGCACCGTACCAAAAACAGGGCGACGTTCCTGCAGGTGTACCGGAAGAAGTCGACGGGCGGGTTCAGCTCGGTGCCGT

ACGTGGTGGCGCTCTTCAGCTCGGTGCTGTGGATCTTCTACGCGCTGGTGAAGACCAACTCGAGGCCGCTGCTGACCATC

AACGCCTTCGGCTGCGGCGTGGAGGCGGCCTACATAGTCCTCTACCTGGCGTACGCGCCGCGGCGGGCGCGCCTGCGGAC

TCTGGCCTACTTCTTCCTGCTGGACGTGGCGGCCTTCGCGCTCGTCGTCGCCGTCACGCTCTTCGCCGTCCGCGAGCCCC

ACCGCGTCAAGTTCCTCGGCAGCGTCTGCCTCGCCTTCTCCATGGCCGTCTTCGTCGCGCCGCTCAGCATCATCGTCAAG

GTGGTCAAGACCAAGAGCGTCGAGTTCCTGCCCATCAGCCTCTCCTTCTGCCTCACGCTCAGCGCCGTCGCCTGGTTCTG

CTACGGCCTCTTCACCAAGGACCCCTTTGTCATGGTAACGACTGATCAATAATGTAATATATGGTTAACTGATCCATATA

TATATATAAAATGGTAACTGAATAATGCTGGGGATGTTTCTCGATTATATATCTATTCAGTACCCCAACGTCGGCGGC

TTCTTCTTCAGCTGCGTCCAGATGGGCCTCTACTTCTGGTACCGCAAGCCCCGCCCGGCGGCCAAGAACAACGCCGTGCT

GCCGACGACCACGGACGGCGCCAACGCGGTGCAGGTGCAGGGGCAGGTCATCGAGCTGGCGCCCAACACGGTGGCCATCC

TGTCGGTGAGCCCCATCCCCATCGTGGGCGTGCACAAGATCGAGGTGGTGGAGCAGCAGCACAAGGAGGCCGCCGTGGCC

GCCGAGACCCGCCGGATGGCCGCCGCAAACCCGGACGGCGCCATGCCGGAGGTCATCGAGATCGTCCCCGCCGCCGCCGC

GGTGTGACCCAACGCCAATCACCATGCACCGTACACACCCTGCTAGCTTCTTATTAGCTAGCTCGGATGACGTACGACAG

TTTGGTGGCAAGTGGCTGGCAGCTCAAGCATGCAGATGCAGGCATCGTCGTCTGCTAGTTGATCGTTTAGTTGGTTAATT

GTTGGATTATTATTGCGTGTCTCTCGTGTGCGTAGTCTTGTCAGTTCAGTTCAGTTCAGTGTCGAATCAAGTAGTAGT

AGCTGTTGTTTGCATTGGATCTGACAATGCATGCTAATAATTATGGTGGTGTGATGGTCTTGGTCGGTACGTGCGTAGTC

GTCTACGTACGCCGTGTCAACGTCGTAGATCTCTACGGGAAGATGATAAGACTGTAACATGCAGGGCATGCATCTATTTA

TACTTAACATATTCTTTGTGTGCTTAATTTT
```

-continued

ZmSWEET16b [GRMZM2G111926]
>lcl|GRMZM2G111926 seq = gene; coord = 8: 33363546 . . . 33368983: -1

SEQ ID NO: 4

```
CTGAGCTGACTGTGGATCTCATCCGTATCGTATATACGTCGTCCTGTTTGGATCCACCGCGTTTTGCTAATTCCCTTCGA

ACCGGCCGGTGGCCTTCGTTCTCCCACCAGGCCTGTCTGTCTGCTGTATCCGCCAGAGCTTCCATGGATTCCACCCTCTT

CATCATCGGCGTCATAGGTAAGCTTGTGTATCATTCTGAACTGCTTTGTTATTATTATTAGTCTTCATTCGTCCAGCTTT

CCTTATCTTCTTCTTCTACATTGAAATAGGCAACATCATCTCAGTTCTCGTCTTCATATCGCCTATGTAAGTGTCTTTCT

CCATATATATGGTTTCCCTGTCGTCGCTGTTGCTAGCTAGCTTTCTTTCTGAACACCACCACGGGCACCAATCCATGCAT

GGATACAGCAAGACGTTCTGGAGGATCGTGCGGGGCGGGACGACGGAGGAGTTCGAGCCGGCGCCGTACGTGTTGACGCT

GCTCAACGCGCTGCTGTGGCTCTACTACGGCCTCACCAAGCCTGACGGCTTCCTCGTCGCCACCGTCAATGGCTTTGGGG

CTGTCATGGAGGCCATCTACGTCGTCCTCTTCATCGTCTACGCCGCCAACCATGCCACAAGGGTGAGGGGTCGGAGCAGC

TGGGGCCAGTATATATAGTTCACTCACACAATCCGTTGCTTAATTCTGCATAATTCTTTCTTCAAGCACTTGAGTCTTAG

GAATTACGGAGTATATAGTTAAAGAAAAGCACAACCACCATTCGTTTATTAAAGAAAAGCATGTGTTGCCTTATATTATA

GTTTGTTCCTTTATCGCAATTATGATTATGCAGGTTAAGACCGCGAAGCTGGCAGCAGCGTTGGACATCGGTGGCTTCGG

AGTCGTGTTTGCGGCCACCACATTCGCCATCAGTGAATTTGAATTGAGAATTATGGTGATAGGAATGATATGTGCCTGCC

TCAATGTGCTCATGTACGGGTCACCCCTTGCTTCTATGGTAAGTTTTTTTCCTCACATGCATATTTATACACTATTCCT

CTTTTCTTTCCTTTTTTGGTTATTTTAGAAACTTAAATCCCCTCTGGTATTAATTCCCGAGAATTTCACTTAATTCCCAA

GAATCCCAAAAAAAATTAAGTTTCTAAACTAGCCCTTAGTGAGACTTAATTTATTTGTTCGCCGTAAGTCGATTTTGAGA

TGCACATTTCTCCTTAATTTTCCTTTTATAGCTGACCGTGCACGGCCTTGAAACATCACGATCTTTTCAGTTAAATTTAA

TTAGCACGGGCTAAATTTTTACATTGCAAAGAAAATAAACTAATTTCACACACACATATATAGTATATAGCTAGCAAAC

TGCTAATGGGCCAGCAAAACTTATGGATGATAACATTGAGCAATGAAATTATTGTCATGTAACGGTAACTATATTATAAT

AGTGAGTTTCGATCCATGATCTAATATATACCATATAATAATATTGATGCCACTTGGCCCCACAGACAAAGTAGAGTATA

GTTCAAGTTTGGAGATATATAAATGATAATAATAATAATAAAGCTGCTCAAGATATTTTCATTCTGGCGATCCATGTCTG

TCCACGATGGATCGACGATAAAATACTCGGTGTTTATTATAATGGACAGGGCGCTTTGTGGGGCGATTATTTTATGTTGT

GTTGTCCCTTTCATGATTATTTATTAAATATAAGGACAGAAGTCCAAGCAAAACACATGTGCCCCAAGCAATAGGGATAT

ATAGTGACATATTGTGGAAATAGTTATATATTTTGGGGGAGAATCATGTGTCAGGGATATTGTACAATAGAAAAACATTT

CTTAGTATGTAGGTCCTCAACTGCCCCTGTTTTTTCTCTTATTTTTAGCAGATGTTCGATCCACTTCCACAATTCCACTT

GCAGGAATAATATAATAAATATAGATATATATGGTACATAAGCTGTATGTAAAATCCATATAATAATATTAATATTACAT

TATATACCTCAACGAATCATTTCTAAAGCTTTTATTAGGTATAATAAAAAGTAAATTTATATTTTGGTGCTTGTAGCTAG

GTGTGGCCGTGTGGGCACGTGCAAGCAACCTTACTCGTTCCACCTCCTATCTTTTGCTCCACTTTGTAAATAATACATA

TTACAGCGTAAAACTGTGTAGAAAGTATGATTTTACGGCTATATACACGGTGTGCTACGACTAAAAGTTAGGGACGACCT

CACGCCGATAATTGGATGACAGATTTTTTCCTTTGATATCTTTCTTCTCTGGCATGCCAAATCGAATTCCTCCCTCTGC

CTTTAATTTCTATTTGTTAGGATTATATGAAACTATTTCCACAAGTATAGTTAGAGACTCAAATTCAGATACTAGAAATT

AATGATGGTTTACAAGCCATAAATAAATAAATTAAAAATAAACATATTTAGATTTTAATTTGAATGAAAAGAGAACATTG

CTTCGGTTTGATGCAGATTAACTTATACAGAAATCATATATTATGTCATGAGAGACAAGCAAAGATTGGTCAACTTATTA

CCATTTCTTGCAAAATCAAGTTTGCCGTATTATTATTTTGTCCTTTTCTTTTTAAAAGATTATTAGCTGGTTATTGGTT

CTCTGGGCAGTTAACGGGGTAGAGTATTCCACAGAATTAAATAATCACCATGCAAGGAACACGCGTTGTCCTCTACATAC

GATTCTTTATTTACTTAATTCTACATCACACATTTTGTGCAAGAACAGTAGCTATTAGAAAAAAATGTGAGCATCGGTT

CACAACCGGCTATAGTACTGGATTATCAACTGATATTAGACAATCGAATTAAAGACCTTATTTTTGAAGGACCGGTGAA

ATGACCAGAAGGGGTGAATTAGAGCCAATCAAATTTTATTGTTAAAAACTTAAATTTAGACCTTATTTGTGAAGGACCAG

AAGAGGTGAATGAGAGCCAATCAAATTTTATTACAAAAAACTAAAATTTAGCACTTAACTTCAATTGAGATGAAGAAATC

GTTCAAACCAGAAGCACATCGGCCAAATAGTAATCTTACGATTTCAAAATGGTACCCCTAGATACATTTGGTTTTTTGTT
```

-continued

```
TAGAATACCGGTATTCTTTGGCTAAGTTCATTTGGTTTATTGGTTTTTGTTTAGAATATGGGTATTCTAAACAAAAACCA
AATGAATTTTGCCAAAAGAGATGGATGTCAATAAAAGCCCACATATCTATTTATAGAGGTGATGGATACATCATATCCAC
TTAGCCGGGGCAAAATGGATCAACTCCTAGGATTTTGATCAGACGACCACGCGCTCTACACAAAGTTGCTTCGCCTCGAC
ACACCCTTTGTGATGATGTCATGTGCCACCTCTGATTCCTGCCGAAACCGCCACCGTCAAGTTTTGAGGCCCAAACTCAG
CAAAACCAGCAGATGGGTGGTTTTGAGGCTCAACCACAAAACCACCGCGAGTAGTGCATCGCATGCGCGTCCCCACGTCC
TGGACACATGTCCCATTAGTCCTTGACCGCATCGGCGACAGTGCGACACAAGCCACTCTGTCATGTCCTCGCGCTAGTGC
GTGTCCTAGGTGTGAGCCACCACAACTTGTCAACCGGCTCCTCCGACCCCTTGGTCAAGTCCTAGTGCTCGTCTTTCATC
ACTCTCCGTCTATCGGCATAAACCCTCGTGTGACCTTCACATTCGCCATTGAACAACATACATGTACTTCACACCTGCAC
ACCATAAGCCGAGAGACATGGTTGCACAATACATAACTCATACTCTGGTCAGTCCACCGACTACATCAAAATACTATCCG
TTGACAATCACTTATCATCAACTCGAACCACAAGGGACAAATCAACTTGTGTTCACAATTGTTTGCCATAGAGAGAAAGA
AAGCGTACTCCGTGTGTTGCTTGGGTTTACCGAGAAGCACGTGTGTAAAATGGGTAGCATACTCTAGTAGTACTACGAGT
GCACGACGTGACTCCTACAGATTCCAAACTCTTGGCAAAATTAATATCGCGACATGTCATCATGTCCATGCCATTACCTT
AGCTGTATTGACAGGCCGGACCTGCTATTTGTGTCGGCCGTACGTGTTCTTGCGGTCCTCGTCGGGTGGGGTTTCGCTCT
CTGAATTTTCTGATTGGTTCCATCGATATTTTCTGATTGGTTCCATCGAAAGCGAAACCAGGACCGTACGTGGCGCCAAA
TTCAACCAGACCACCCATCCCTTCCCGGGGTCATGTCACATCCCTGTTGCTTCACGTTTTCTTACAAAATTACCCGCTCC
GTCCGTGAAGCAAATATAACTATGATATCCCTATCTGTCAGAGTAGTTTAAATTTAACTAAATTTATAATAAACAATACT
CGCTTTGGTCCTAAATCTAGACACATATATATATATATATATATAACACATACATCAAGTATTGTATAAATTCACA
AAATACCACTATATGAACGCCCTTAAATTTTAAATTAAAAAATTATCTAAGAAAACATAAGCAATAATTAACCCATGCCA
ATGCAAGTTGAATACTTGAATTGAAAAAAGTTGATTCCAGCTCAGGGAACCTATAACCATGGCTTCGCATGAGTTGGCGA
TTGCCTGAACAGGCCCATGCAGAGCAACTAACCATAGAATAGAACAATACGCGATGAAATTCACCGTACCCTGCAACGTA
ATGGATGTGTGATTAGTATCACCGGCACCTCATTTTTACCCGTCATCTCGTTGTACCTACATTTTCAGAAAACGGTGATC
ACGACAAAGAGCGTGGAGTTCATGCCATTCTTCCTGTCCTTCTTCCTCTTCCTCAACGGAGGCGTCTGGGCAACGTACGC
GGTGCTTGACCGCGACATCTTCCTCGGGGTAATGTTTAAAGCCTCTCTGTTCTTCTCGATCTTCTTCCCCAACCTCTGTC
TTTTCCGCTACCCATACTAAACAGAACCTCTCGATCGCTCTCTGCATGCAGATCCCCAATGGGATAGGCTTCGTGCTTGG
CACCATCCAGCTGATCGTCTACGCGATCTACATGAACAGCAAGGCCTCCCAATGCAGCAAAGAAACAGCGTCCTCGCCTC
TTCTGGCCTCCGACCGGGGAGAAGCATCTAGCCATGTCTGATGATGAGCTTCGATCAGTGCGCGCGCTGGAGTATAGCAT
AGAAGTCTCTTGCTGTCAAAAACTTCCAAGACCAACGGTACCTACCAGCATGCATGCATGCAAGAGGTTACCAATTTTTA
TTGTTTGAAAATTCATGTAAACTTGTGACCTCCATGGATTGTTTCTTTCTTTGGTATAAGCTTCGAAGATGTTAGATTGT
TAGCACGGTAGTTTTGCCAGAGAAGGGTGTTGTCAATATAATGAAGAAATGGTGAAAATCCATACATTTGATTATCGA
ZmSWEET15b [GRMZM5G872392]
>lcl|GRMZM5G872392 seq = gene; coord = 5: 164854921 . . . 164858109: -1
                                                                          SEQ ID NO: 5
CTCAGGAGCTAATGACTCACCTCTCCGTGCTCACCTCCTCTTCTTGAGGCTTGAGCTCTCTCTTCCTCTCTCCCCTCAGC
TCATCTCCACCGTCTCCCTATATATAGGATGCTCTGCCGGCTCCAAGGTTCCCAAGCGCCCAAGGCAGCGGAGAGAGCTA
GCTCCCTCCTCCTCCTCAGGTAGCGAGCGAGCGAGCTCCTCTGCCCCTCTGCACACCTGGCCTCCCCTTCTCCGCTGCAG
GACCGCCGTTGACGACTGCTCCACCAGTACTGCGCGCGCCCGCGCTGCCTACCCTTACCTAGCCAGAGCGCGGCGCGCGA
GAGGGAGAACGACCAGGAGGGGAGGAGATCGATCGATCGATCGATCGAGATAGATGGCTTTCCTCAACATGGAGCAGCAG
ACCTGGGCCTTCACCTTCGGTATCCTAGGTACATATATACTGTCAGTCTGTCACTCGTAGCTACTAATTAACCGCATCAA
CGGAGCCGCCCTGCCGTCTTCGTCCTCGTCAGTGTTTCTGCATTGTTTTCCTTCCTTGTCCCAAGTCCTTTGAGACGCAC
GCATACATGATACATGCATGGCATCATCGTCTCCCAAGTCCTAGGTACAGTTTCATCACCGCGCGCCTCTCTCAGATATG
TGTCGTCGTACAGGACAACACAACACGTCCTCGTCAATCTACTAGCTATATGCGCTAATAACCACCTCTTCCTTTCCGAG
CCACGGCACAGTATAGCCTGCCATCCGAACGAACGGAACCGCCCAAAACCCAACTTTTTTTGGGCCTAACTAATGCGGTG
```

```
GTTAGCCCAAACAAAGAAACCAGGGCAGTCATACATTTTACATGTAGTACCTGCTTGACGACGGGAACCAACACAACGGC

GCGCCGCGAGGAGAGTTTGTTCCATTTCCTCCGCCTGCAGGCTAGCTGCAGCTAATAACCCCGGCCGCCGGATGTTCTCC

TTCTCGCATGCTTTTTTTTGGGGGGTTCTTTCTCCGCCTCCTGCTCTTCGTCTGTTCTACCATCGTCGATCACACAGCA

ATTTGACTGACCGCGTCTGTCCTTCCGACCTTGCCGTTTTGCTTTGCAGGTAACATAATCTCGCTGATGGTGTTCCTTTC

GCCGCTGTAAGTAACTCTCTGCTTTAATTTATTTAACCTAGCCGTGAACTTTTCATATTTACGTTTACAGTATCCAGTAC

CATGCATAATATACTACCAATATGTTTCTATGTATATTCAGTAAAGGGAAGCGTCCAAAATATATACTGCCATCAGGTAT

GATGAGAACATATATATAAAGAACATGGCACGCACGCATGCGTATCTCACTGTTGAATGAATGACGTGCCATCATCGTCC

ATGCTCTTCTAGATCCTTTCCTTTAATTTATGCGTGGTTCTAGATCCCCCTATATATATATATATATATATATATATAT

ATATATATATACGTACACCTGAAGACAACATAGCTAGCTAGGAAATAAACTCGTTGGGAATTGAATTGTCGCATTAATAA

CGTCACTTTAATCAGTTGCGAGCCAGTACGTGTCACTGTTCGGTGGTTGCGTTGCACATGCTTTTAGTATGGAACAGCGC

ACGCAATCTAGTAATAATTAATCTAAAAAATCACACGGTAAAAAATATTCGTTCCCGCTGATCCCGCGCAGGCCGACGTT

CTACCGCGTGTACCGCAAGAAGTCGACGGAGGGGTTCCAGTCGACCCCGTACGTGGTGACGCTGTTCAGCTGCATGCTGT

GGATCTTCTACGCGCTGCTCAAGTCCGGCGCCGAGCTGCTGGTGACCATCAACGGCGTCGGGTGCGTGATCGAGGCGGCG

TACCTGGCCGCGTACCTGGTGTACGCGCCCAAGGCCGCCAGGGCGCTGACGGCCAAGATGCTGCTGGGGCTCAACGTCGG

CGTCTTTGGACTCGCCGCGCTCGCCACCATGGTGGTCTCCAGCGCCGGCCTCCGCGTGCGCGTGCTCGGCTGGATCTGCG

TCAGCGTCGCGCTCAGCGTATTCGCCGCGCCGCTCAGCATCATGGCACGTATCTAATTTAATCTCTCTCTCTCTCTCT

CTCTCTCTCTCTCTCTCTCTGAAGAGGGATGTGAATTGTTGGAACCGCCATTAATTCGCTGACTGCCCTATCTACA

TCTACTTTCCTGCAGCGGCAGGTGGTCCGGACCAAGAGCGTGGAGTTCATGCCCATCTCGCTCTCCTTCTTCCTGGTGCT

GAGCGCCGTGATCTGGTTCGCGTACGGCGCGCTGAAGAGGGACGTGTTCGTGGCGTTCCCCAACGTGCTGGGCTTCGTCT

TCGGCGTCGCGCAGATAGCGCTGTACATGGCGTACAGGAACAAGGAGCCCGCGGCGGTGACGGTGGAGGAGGCGAAGCTG

CCGGAGCACGCCAAGGAGGTGGTGGTGGCCGCGGCGGCGGCCGAGGCCAGGGCGAGCTGCGGTGCTGAGGTGCACCCCAT

CGACATCGACATCGAAGCTACGCCGACGCCGGTGGAGGAGGTGCACGAGCCGCAGGTGGTCGTGGTCGTCGACGTGGACG

TGGAGCCTGTCACCTGCGCCGGCGCCGCCGAGGCAGCTGCGGGAGCAGGGGCAGATGCGTCCGGCGTGGCCGACGGCGGC

GTCCCTGGACCCATGGCGCCGCCGGAGCAGCTGGCGATCAAGCCCGACATGGCCATTTCCGTGGAGGCGTAGGTTGGTTA

AAGTGTAATAGCAGAGTGAGTCGATATCGATCAGTAGTAGATTTGTCGAGTCAAGGAAGGGCCTGCTGCTGCTGCTACG

CGACAGCAGCGGCCAGATGTACTGCCTGCATGCATGCAGTCCCTCCCGTTGACTCGACCCGTAGAGAAGGGATGGGATGG

AAGTAGCCGGGTCCTTGGGCGAGTAGCGGCGCCTTGGCACCCACGGGCCAGCCGTACTGGCCTGTGTGATGAACCGGCGA

GAGAGATGAGATAATGTGCGAGCGAGAGAGGGTTGGTTGGGTTGTGGTAGTTGAAGAAGACGGCTAGCTAGCTGCTGCTG

CTGGGCTCTCTATCTGTCTCTAGATCTGTGTATGTCTGTGTAATCGAGGATTCCCTCACCTTGCATGCCGCCTCCCTTTT

GTGTCCTTCAGTCTGATGATTGTTTTCATTCCATCCATGCCGGCGTCGCAGTAATAAAATTTTTTGG
```

That which is claimed:

1. A method of identifying and/or selecting a maize plant or maize plant part having increased yield under non-drought conditions, increased yield stability under drought conditions, and/or increased drought tolerance, the method comprising the steps of:
   (a) detecting, in a maize plant or maize plant part, an allele of at least one marker locus that is associated with increased yield under non-drought conditions, increased yield stability under drought conditions, and/or increased drought tolerance in a plant, wherein said at least one marker locus is located within a chromosome interval on chromosome 5 defined by and including base pair (bp) position 164854921 to base pair (bp) position 164858109 (Gene Model ID No: GRMZM2G872392), wherein the chromosome interval comprises a haplotype comprising a C allele corresponding to position 164854921; an A allele corresponding to position 164855482; or a G allele at position 164858109;
   (b) selecting a maize plant or maize part on the basis of the presence of the at least one allele of a marker locus in (a);
   (c) crossing the plant of (b) with a maize plant not comprising said at least one allele of a marker locus;
   (d) collecting seed from the cross of (c); and
   (e) growing a progeny plant from the seed of (d), wherein said progeny plant comprises in its genome said marker locus that is associated with increased yield under non-drought conditions, increased yield stability under drought conditions, and/or increased drought tolerance in a plant.

2. The method of claim 1, wherein the plant part in which said at least one marker locus located within said chromosomal interval is detected is regenerated to produce a plant having increased yield under non-drought conditions, increased yield stability under drought conditions, and/or increased drought tolerance.

3. A method of producing an elite maize plant having increased yield under non-drought conditions, increased yield stability under drought conditions, and/or increased drought tolerance, the steps comprising:
- (a) crossing a first maize plant or maize germplasm with a second maize plant or maize germplasm, wherein said first maize plant or maize germplasm comprises within its genome a marker associated with increased yield under non-drought conditions, increased yield stability under drought conditions, and/or increased drought tolerance in a maize plant, wherein said marker is located within a chromosome interval on chromosome 5 defined by and including base pair (bp) position 164854921 to base pair (bp) position 164858109 (Gene Model ID No: GRMZM2G872392),wherein the chromosome interval comprises a haplotype consisting of a C allele corresponding to position 164854921; a A allele corresponding to position 164855482; or a G allele at position 164858109;
- (b) selecting a maize plant or maize part on the basis of the presence of said haplotype;
- (c) creating a progeny plant from (b) comprising said haplotype;
- (d) backcrossing to plant of (c) at least two generations; and
- (e) crossing the line of (d) to create an elite maize plant or maize germplasm comprising said haplotype of (b).

4. A method for producing a hybrid maize plant having increased yield under non-drought conditions, increased yield stability under drought conditions, and/or increased drought tolerance, the method comprising:
- (a) identifying a first maize plant comprising a chromosome interval on chromosome 5 defined by and including base pair (bp) position 164854921 to base pair (bp) position 164858109 (Gene Model ID No: GRMZM2G872392), wherein the chromosome interval comprises a haplotype consisting of a C allele corresponding to position 164854921; a A allele corresponding to position 164855482; or a G allele at position 164858109,
- (c) crossing the first maize plant a second maize plant not comprising said haplotype to produce an F1 generation; and
- (d) selecting one or more members of the F1 generation that comprises said haplotype whereby a hybrid maize plant having increased yield under non-drought conditions, increased yield stability under drought conditions, and/or increased drought tolerance is produced.

* * * * *